United States Patent [19]

Gullans et al.

[11] Patent Number: 5,182,299
[45] Date of Patent: Jan. 26, 1993

[54] TREATMENT OF OSMOTIC DISTURBANCE WITH ORGANIC OSMOLYTES

[75] Inventors: Steven R. Gullans, Natick; Charles W. Heilig, Needham, both of Mass.

[73] Assignee: Brigham and Women's Hospital, Boston, Mass.

[21] Appl. No.: 670,779

[22] Filed: Mar. 19, 1991

Related U.S. Application Data

[63] Continuation-in-part of Ser. No. 495,575, Mar. 19, 1990, abandoned.

[51] Int. Cl.$^5$ .................... A61K 31/35; A61K 31/34; A61K 31/70
[52] U.S. Cl. .................... 514/460; 514/473; 514/53; 514/54; 514/59; 514/870
[58] Field of Search .................... 514/23, 53, 54, 59, 514/870, 473, 460

[56] References Cited

U.S. PATENT DOCUMENTS

| | | | |
|---|---|---|---|
| 3,911,915 | 10/1975 | Seifter et al. | 604/4 |
| 4,271,144 | 6/1981 | Holly | 424/78 |
| 4,346,706 | 8/1982 | Leveen et al. | 604/28 |
| 4,663,166 | 5/1987 | Veech | 424/663 |
| 4,727,061 | 2/1988 | Kramer et al. | 514/18 |
| 4,874,742 | 10/1989 | Ecanow et al. | 514/2 |

OTHER PUBLICATIONS

Arakawa et al., *Biophysical Journal* 47:411–414 (1985).
Arieff et al., *The Journal of Clinical Investigation* 52:571–583 (1973).
Bagnasco et al., *The Journal of Biological Chemistry* 261(13):5872–5877 (1986).
Balaban et al., *Am J. Physiol* 245 (Cell Physiol. 14):C439–C444 (1983).
Balaban et al., *Kidney International* 31:562–564 (1987).
Beck et al., *Klin. Wochenschr.* 66:843–848 (1988).
Blumenfeld et al., *Kidney Int.* 33:255, Abstract 54 (1988).
Chambers et al., *J. Clin. Invest.* 79:731–737 (1987).
Chambers et al., *The Journal of Infectious Diseases* 152(6):1308–1316 (1985).

Corder et al., *The Journal of Histochemistry and Cytochemistry* 25(1):1–8 (1977).
Forster et al., *The Yale Journal of Biology and Medicine* 52:497–515 (1979).
Grantham, J. J., in *Disturbances in Body Fluid Osmolality* (Andreoli, T. E. et al., Eds.), Amer. Phiol. Soc., Bethesda, pp. 217–225 (1977).
Grossman et al., *Am. J. Physiol.* 256 (Renal Fluid Electrolyte Physiol. 25):F107–F112 (1989).
Gullans et al., International Symposium on Prevention, Treatment, and Diagnosis of Acute Renal Failure, Edmonton, Alberta, Canada (1988).
Gullans et al., *Kidney Int.* 33:434, Abstract 112 (1988).
Gullans et al., *J. Renal Physiol. Biochem.* 12:191–201 (1989).
Heilig et al., *Kidney Int.* 33:194, Abstract 66 (1988).
Lockwood, A. H., *Arch. Neurol.* 32:62–64 (1975).

(List continued on next page.)

*Primary Examiner*—Richard L. Raymond
*Assistant Examiner*—Gary E. Hollinden
*Attorney, Agent, or Firm*—Sterne, Kessler, Goldstein & Fox

[57] ABSTRACT

A method of treating an osmotic disturbance in an animal which comprises administering to an animal an effective amount of an organic osmolyte, wherein the organic osmolyte is a polyol. Specific polyols include myo-inositol and sorbitol. Also included are precursors of organic osmolytes including precursors of polyols. Other polyol precursors are selected from the group consisting of glucose, glucose polymers, and glycerol. Also included is a method for preventing an osmotic disturbance substantially associated with physical activity comprising enterally administering to a subject prior to, during, or both prior to and during the physical activity an effective amount of an organic osmolyte or a precursor of an organic osmolyte, wherein the organic osmolyte or precursor is a polyol.

14 Claims, 23 Drawing Sheets

OTHER PUBLICATIONS

Nakanishi et al., *Am. J. Physiol.* 255 (Cell Physiol. 24):C181–C191 (1988).

Nakanishi et al., *Proc. Natl. Acad. Sci. U.S.A.* 86:6002–6006 (1989).

Pierce, S. K., *Biol. Bull.* 163:405–419 (1982).

Prockop, L. D., *Arch Neurol* 25:126–140 (1971) 6006 (1989).

Robinson et al., *Comp. Biochem. Physiol.* 19:187–195 (1966).

Le Rudulier et al., *Science* 224:1064–1068 (1984).

Sambasivarao et al., *Biochimica et Biophysica Acta* 806:195–209 (1985).

Shek et al., *Journal of Medicinal Chemistry* 19(1):113 (1976).

Somero, G. N., *Am. J. Physiol.* 251:R197–R213 (1986).

Trachtman et al., *Pediatric Research* 23(1):35–39 (1988).

Veech, R. L., *The American Journal of Clinical Nutrition* 44:519–551 (1986).

Wirthensohn et al., *Pflugers Arch* 409:411–415 (1987).

Wirthensohn et al., *Biochemistry of Kidney Functions*, INSERM Symposium No. 21, F. Morel, ed., Elsevier Biomedical Press B.V., pp. 119–128 (1982).

Wirthensohn et al., *Am. J. Physiol.* 256:F128–F135 (1989).

Yancey et al., *Science* 217:1214–1222 (1982).

Lohr, J. W. et al. Life Sciences 43:271–6 (1988).

Hahn, R. G. et al. J. Urology 142:1102–5 (1989).

Hutton, J. C. et al. Aust. J. Biol, Sci. 28:109–114 (1975).

Pollock, A. S. American J. Physiology 239(3):F195–205 (1980).

FIG. 3A
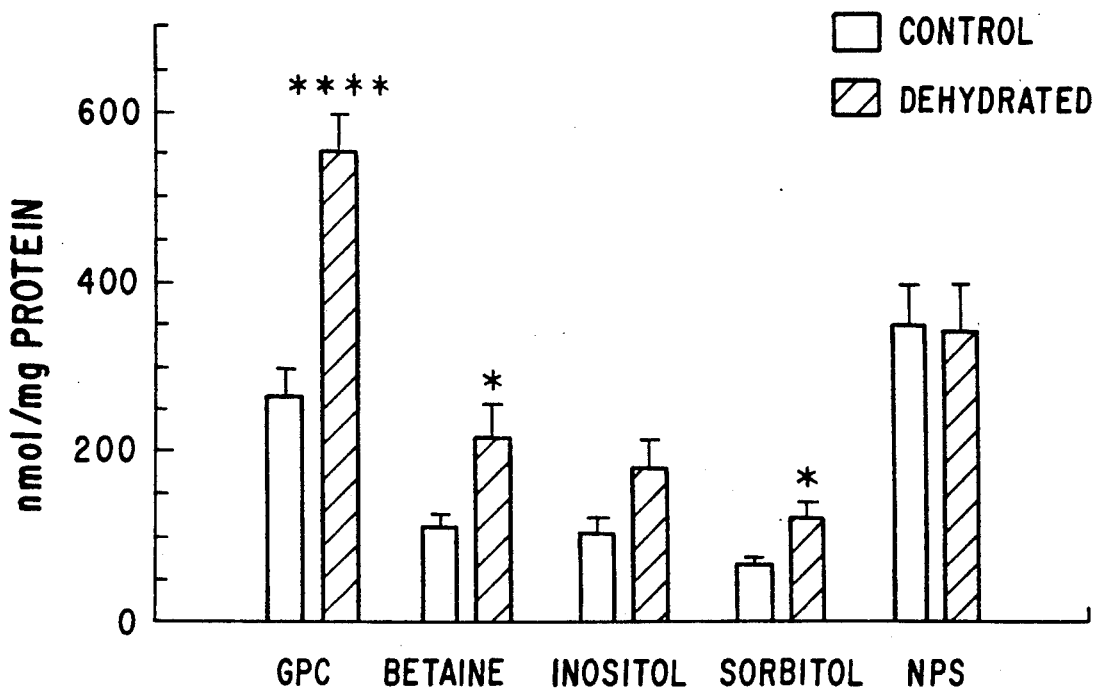
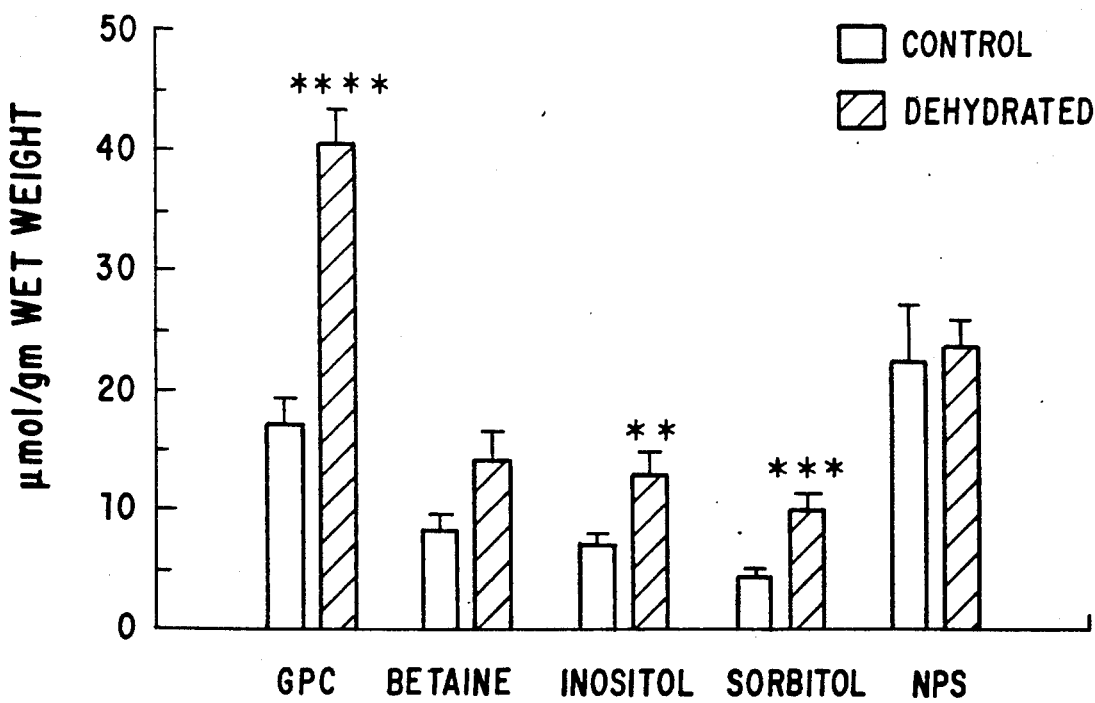
FIG. 3B

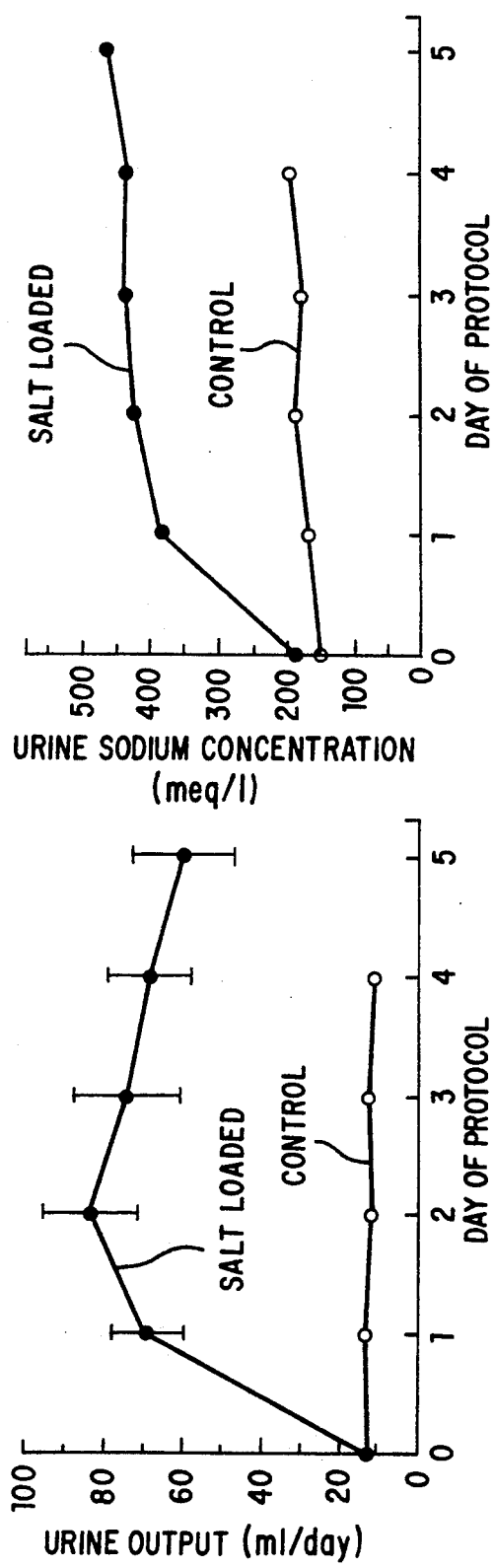
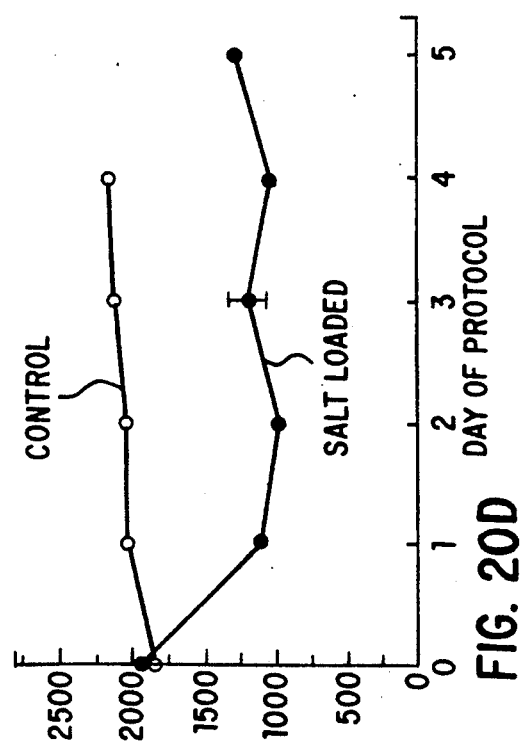
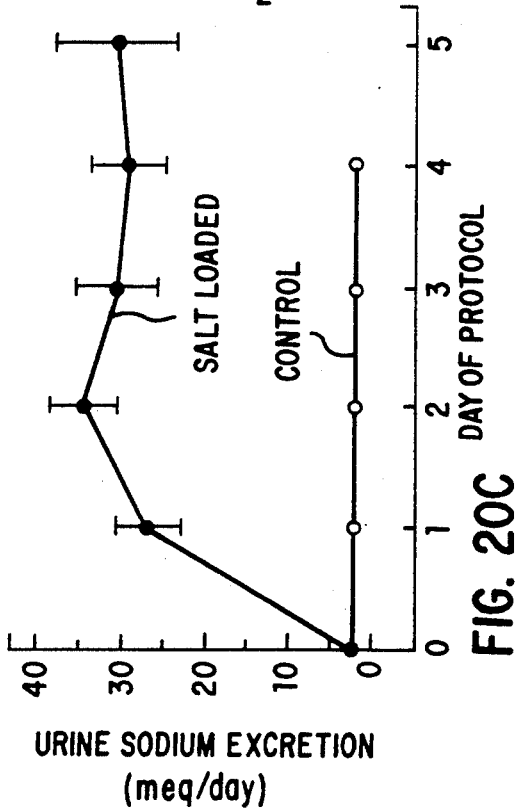
FIG. 20A
FIG. 20B
FIG. 20C
FIG. 20D

TREATMENT OF OSMOTIC DISTURBANCE WITH ORGANIC OSMOLYTES

This invention was funded by a research grant from the National Institutes of Health, 1RO1 DK36031, which provides to the United States Government certain rights in the invention.

CROSS REFERENCE TO RELATED APPLICATIONS

This application is a Continuation-in-Part of U.S. patent application Ser. No. 07/495,575, filed Mar. 19, 1990, now abandoned.

BACKGROUND OF THE INVENTION

1. Field of the Invention

The invention relates to the use of organic osmolytes in oral or parenteral fluids to treat osmotic disturbances such as those substantially associated with acute and chronic hypernatremia and hyponatremia.

2. Description of the Background Art

A. Organic Osmolytes

Study of osmoregulatory behavior in marine animals, plants, and bacteria demonstrated that organic solutes known as osmolytes accumulate intracellularly when the extracellular or environmental osmolality is significantly increased (Blundin, G. et al., *Bot. Mar.* 25:563-567 (1982); Pierce, S. K., *Biol. Bull. Woods Hole* 163:405-419 (1982); Somero, G. N., *Am. J. Physiol.* 251:R197-R213 (1986); Yancey, P. H. et al., *Science* 217:1214-1222 (1982)). High levels of inorganic salts and urea are toxic to numerous enzymatic and other cellular processes. Certain organic solutes such as trimethylamines counteract the toxic effects of urea, enabling cells to tolerate high concentrations of urea (Somero, G. N., supra: Yancey, P. H. et al., supra).

In the renal medulla, where osmolality and urea concentration can be very high during antidiuresis, the relative significance of the individual osmolytes has not been clearly delineated. During antidiuresis an intracellular osmotic gap exists in the renal inner medulla (IM) such that the concentration of electrolytes plus urea is lower in the cell than in the surrounding extracellular fluid (ECF) (Beck, F. et al., *Kidney Int.* 25:397-403 (1984); Bulger, R. E., *Kidney Int.* 31:556-561 (1987)). The magnitude of this gap is controversial, ranging from 100 to 650 mosmol/kg $H_2O$. Several investigations have identified organic solutes (osmolytes) as significant constituents of this gap. Over 30 years ago Ullrich (Ullrich, K. J., *Pfluegers Arch.* 262:551-561 (1956)) observed a large pool of glycerophosphorylcholine (GPC) in the dog IM, and others later discovered high myo-inositol levels in the dog IM (Cohen, M. A. H. et al., *Proc. Soc. Exp. Bio. Med.* 169.380-385 (1982)). More recently, with the use of nuclear magnetic resonance (NMR) spectroscopy, gas chromatography, and enzymatic analysis, trimethylamines and polyols were identified in the rabbit and rat renal IM (Bagnasco, S. et al., *J. Biol. Chem.* 261:5872-5877 (1986); Balaban, R. S, et al., *Kidney Int.* 31:562-564 (1987); Balaban, R. S. et al., *Am. J. Physiol.* 245:C439-C444 (1983); Corder, C. N. et al., *J. Histochem. Cytochem.* 25:1-8 (1977); Yancey, P. H. et al., supra). In particular, significant levels of GPC and glycine betaine (betaine) as well as myo-inositol and sorbitol were observed. Trimethylamines have also been implicated in human renal function since both glycine betaine and proline betaine were identified in urine (Chambers, S. T. et al., *J. Clin. Invest.* 79:731-737 human urine (Chambers, S. T. et al., *J. Clin. Invest.* 79:731-737 (1987)). Finally, several reports suggest that significant levels of amino acids are accumulated in the mammalian renal IM (Balaban, R. S. et al., 1983, supra: Law, R. O. et al., *J. Physiol. Lond.* 386:45-61 (1987); Robinson, R. R. et al., *Comp. Biochem. Physiol.* 19:187-195 (1966)).

Bagnasco and co-workers (supra) compared diuretic with antidiuretic rabbits and found that a 105% increase in urine osmolality was accompanied by an increase in IM urea (73%) and betaine (101%) content; however, sorbitol and GPC were not significantly elevated. Cohen et al., (supra) showed that acute (2-3 hour) water diuresis produced a 36% decrease in IM myo-inositol content. Amino acids, in comparison, either did not change (Robinson, R. R. et al., supra) or changed by only 28% (Law, R. O. et al., supra) during in vivo antidiuresis. This observation is in striking contrast to in vitro tissue slice studies which indicated that acute increases in ECF osmolality caused a dramatic (148%) and rapid (15-25 min) rise in cellular amino acids in IM tissue (Law, R. O. et al., supra). Interestingly, this increase was blocked by trimethylamine N-oxide, a prominent osmolyte in elasmobranchs.

B. Clinical Disorders of Osmoregulation

1. Hypoosmolar States

Hypoosmolality or hyponatremia is the most common disorder of body fluid and electrolyte balance encountered in the clinical practice of medicine (Anderson, R. J. et al., *Ann Intern. Med.* 102:164-168 (1985)), with incidence ranging from 15-22% in both acutely (Flear, C. T. G. et al., *Lancet* 2:26-81 (1981) and chronically (Kleinfeld, M. et al., *J. Am. Geriat. Soc.* 27:156-161 (1979) hospitalized patients. Hyponatremia is a major cause of morbidity, though its contribution to mortality is not yet settled.

In its severe form, hyponatremia is the most frequent cause of metabolic coma with or without seizures or other neurologic manifestations. In chronic hyponatremia, the patient or animal can be remarkably free of central nervous system (CNS) manifestations, with serum sodium concentrations between 110-115 mEq/liter. This observation is a sign of volume regulation in response to brain cell overhydration and interstitial fluid volume expansion.

The causes of hyponatremia are well known. In all cases, the hypoosmolar state results from either an absolute or relative excess of water in the body. It can occur with or without edema, and with or without salt depletion or reduced ECF volume. In all cases, water intake is excessive relative to the kidney's ability to excrete it. The morbidity, clinical presentation, and mortality rate of patients with hyponatremia are related to the age of the patient (the oldest and youngest are most affected), the acuteness of the decline in serum sodium, the severity of the hyponatremia, and the concomitant presence of certain medical conditions.

A. I. Arieff (*N.Eng. J. Med.* 314:1529-1534 (1986)) studied 15 women in whom hyponatremia occurred after elective surgery, leading to death in 4 and recovery of 8 in a persistent vegetative state. It was not certain whether hyponatremia itself was the direct cause of neurological damage. (See, also: Arieff, A. I. et al., *Medicine* 55:121-129 (1976); *Clin Endocrinol. Metab.*

13:269-294 (1984); Sterns, *Ann Int. Med.* 107:656-664 (1987).

The cellular transport processes responsible for volume regulation during hypotonicity in the brain are poorly understood. Volume regulation has been demonstrated in many cell types in response to hypotonicity of the ECF, however, and ion loss is similar to that of brain. Such losses could include a marked increase in potassium conductance and/or $K^+/Cl^-$ cotransport, or an inhibition of the $Na^+$-$K^+/2Cl^-$ cotransporter in response to volume expansion.

The correction of hyponatremia performed in too rapid a manner is thought to lead to neurological deficits due to brain myelinolysis in man, similar to the production of demyelinating lesions in animals by rapid correction of hyponatremia (Wright, D. G. et al., *Brain* 102:361-385 (1979); Sterns, R. H. et al., *N. Eng. J. Med.* 314:1535-1541 (1986); Kleinschmidt-Demasters, B. K. et al., *Science* 211:1068-1070 (1981); Laureno, R., *Ann Neurol.* 13:232-242 (1983); Ayus, J. C. et al., *Am. J. Physiol.* 248:F711-F719 (1985); and Illowsky, B. P. et al., *Brain* 110:855-867 (1987). However, it is not yet settled whether, and under what circumstances, hyponatremia and subsequent changes in plasma osmolality cause cellular and tissue damage and death (Ayus et al., *Am J. Med.* 78:897-902 (1985); Narins, R. G., *N. Eng. J. Med.* 314:1573-575 (1986)).

Much is known about cellular adaptation to hypoosmolar conditions in vitro (Grantham, J. J., in *Disturbances in Body Fluid Osmolality* (Andreoli, T. E. et al., Eds.), Amer. Physiol. Soc., Bethesda, 1977, pp 217-225; Hoffmann, E. K., in *Transport of Ions and Water in Animals.* (Gupta, BL et al., Eds.), Academic Press, London, 1977, pp 285-332). However, much remains to be learned about such adaptive changes and their consequences for mammals in vivo (Grantham, J. J. et al., *Circ. Res.* 54:483-491 (1984).

Useful animal models have been developed in which chronic severe hyponatremia in rats can be maintained for prolonged periods by subcutaneous (SC) infusions of the antidiuretic vasopressin analogue, 1-deamino-(3-D-arg) vasopressin (DDAVP) (Verbalis J. G. et al., *Kidney. Int.* 34:351-360 (1988). This allows the animals to be maintained for prolonged periods without a need for excess fluid administration, and in the absence of tissue catabolism, morbidity and mortality. Analysis of brain water and electrolyte contents has revealed normalization of brain water content, demonstrating the ability of brain tissue in vivo to volume regulate completely in response to hyponatremia of sufficient duration.

In a similar model involving treatment of rats with dextrose in water and vasopressin, Ayus, J. C. et al. (*Am. J. Physiol.* 257:F18-F22 (1989)) found that (1) spontaneous correction of severe symptomatic hyponatremia (serum sodium <120 mEq/l) resulted in 68% mortality as compared with 15% mortality in rats with asymptomatic mild hyponatremia (serum sodium between 120 and 130 mEq/l); (2) rapid correction of severe hyponatremia by hypertonic saline at a rate of change of absolute serum levels of <25 mEq/l in the first 24 hr. improved survival to 100%; and (3) rapid correction of severe hyponatremia of >25 mEq/l in the first 24 hr. resulted in histological brain damage and 88% mortality. It was concluded that correction of hyponatremia can be safe if the rate of change of serum sodium is kept between 14 and 25 mEq/l during the first 24 hr.

Sterns, R. H. et al. (*Kidney Int.* 35:69-75 (1989) demonstrated that rats adapted quickly to hyponatremia and survived with extremely low plasma sodium levels for prolonged periods. Slow correction (0.3 mEq/l/hr) permitted 100% survival. Rapid correction was well tolerated when hyponatremia was of brief duration. However, in animals that had already adapted to the osmotic disturbance, more rapid correction by treating with IM NaCl, or by withdrawal of DDAVP, caused brain dehydration leading to demyelinating brain lesions and over 40% mortality.

2. Hyperosmolar States

Hypernatremia results from water loss in excess of isotonic proportions of sodium chloride or sodium bicarbonate, or from an increase of one of these salts without a proportionate gain in the amount of water. Thus, total-body water can be normal, reduced, or elevated, but in all cases water is lost (to varying degrees) from every cell in the body. Cellular dehydration, of course, is secondary to the movement of water along its osmotic gradient because the permeability of body cells to sodium from the basolateral or circulatory side of the cell is quite low. When the rise in extracellular osmolality is acute, the fractional loss of water from cells examined is quite uniform. Later, however, various cells or organs deviate from the water loss predicted by the assumption that the cells or organs behave as perfect osmometers.

Arieff and colleagues infused hypertonic glucose rapidly into rabbits so as to elevate their plasma glucose to 60 mM (1100 mg/dl) in 1 hour (Arieff, A. I. et al., *J. Clin. Invest.* 52:571-583 (1973)). This level was then maintained for 4 to 6 hours. At 2 hours, the fractional losses of water from brain and skeletal muscle were equal, slightly more than 10%. By 4 hours, however, brain water content had returned to normal, whereas that of muscle remained depressed. This remarkable recovery of the water content of the brain to normal despite sustained and marked hyperosmolality of the plasma is an example of complete "volume regulatory increase." Such regulation of cell volume is observed to varying degrees in many areas of the body, but nowhere is it more complete than in the brain. In the Arieff et al. study (supra), skeletal muscle cells at 4 hours showed no volume regulatory increase.

In contrast to systemic tissues, the unique characteristics of the blood-brain barrier (BBB) and blood-cerebrospinal fluid (CSF) barrier allow for maximal maintenance of brain volume despite the hyperosmolality of the blood. The "tight" epithelium-like properties of the capillary endothelium of the brain, together with the intimate relationship on both a hydrostatic and compositional basis between the brain ECF and the CSF (Cserr, H. F., *Ann. N.Y. Acad. Sci.* 529:9-20 (1988)), allow for both the intracellular and the ECF volume to minimize deviations from normal. The brain cells regain normal water content with an increased solute content after the acute hyperosmolar stress has caused the loss of ECF and cellular water, despite the sustained ECF hyperosmolality.

All animals studies of acute hypernatremic states have demonstrated varying degrees of volume regulatory increase in the brain. The more acute and severe the hypernatremic or hyperosmolar state (induced by hypertonic saline, urea, or glucose), the more severe is the initial dehydration and contraction of the brain, and the resulting neurologic damage. If the initial hypernatremia and hyperosmolality are less severe, the majority of animals survive despite a hyperosmolar state sustained for many hours or even for days. After this period, the volume regulatory increase is maximal. The cells have gained sodium, chloride, and potassium as well as nonelectrolyte solutes (including certain amino acids), and brain volume has returned to normal (Katzman, R. et al., *Brain Electrolytes and Fluid Metabolism.* Baltimore, Williams & Wilkins (1973); Arieff, A. I., in *Fluid, Electrolyte and Acid-Base Disorders.* (Arieff, A. I. et al., Eds.), New York, Churchill-Livingstone, p. 969 (1987); Kleeman, C. R., *Hosp. Pract., pp.* 59-73 (May 1979); Arieff, A. I. et al., in *Disturbances in Body Fluid Osmolality.* (Andreoli, T. E. et al., Eds.), Bethesda, *Am. Physiol. Soc.,* pp. 227-250 (1977); Lockwood, A. H., Arch. *Neurol* 32:62-64 (1975); Holiday, M. A. et al., *J. Clin. Invest.* 47.1916-1928 (1968); Culpepper, R. M. et al., in *Clinical Disorders of Membrane Transoort Processes,* (Andreoli, T. E. et al., eds.), New York, Plenum, p. 173 (1986); Sotos, J. F. et al., *Pediatrics* 26:925-937 (1960)).

Studies of "volume regulatory increase" and "volume regulatory decrease" in other cells and tissues suggest that dehydration of the cells in response to hyperosmolar stress leads to activation of the coupled $Na^+/K^+/2Cl^-$ co-transport system and/or the chloride/bicarbonate exchanger and the sodium/hydrogen antiporter in the plasma membrane (Sotos, J. F. et al., supra). The parallel activation leads to a gain in cellular sodium and chloride in exchange for hydrogen and bicarbonate respectively, and a probable decrease in potassium conductance out of the cell. The net effect is a cellular gain in sodium, potassium, and chloride, a rise in intracellular osmolality, and a return of cell volume toward normal. It is probable that these cellular mechanisms are responsible for part of the "volume regulatory increase" occurring in brain cells. However, in numerous experiments carried out by Arieff and associates, the gain in osmolality in brain cells after administration of hypertonic sodium chloride and hypertonic glucose could not be explained by the osmotic equivalent of the gained electrolytes (see Arieff, A. I., 1987, supra).

The term "idiogenic osmoles," was adopted to define the undetermined solutes (Arieff, A. I. et al., 1973, supra), and was first used with respect to systemic tissues (McDowell, M. E. et al., *Am. J. Physiol.* 180:545-558 (1955)) or brain (Sotos, J. F. et al., supra). The relative contribution of electrolyte uptake or nonelectrolyte "idiogenic" osmole accumulation to the total increment in cell osmolality differs depending on the nature of the solute causing the hyperosmolar state (Culpepper, R. M. et al., supra). The acute achievement of osmotic equilibrium is almost solely due to cellular water loss. Subsequently, electrolyte gain and idiogenic osmole accumulation account for the solute gain and return of brain water to normal. About 50% to 60% of the osmoles responsible for volume regulation during chronic hypernatremia were found to comprise amino acids (Arieff, A. I. et al., 1977, supra: Lockwood, A. H., *Arch. Neurol.* 32:62-64 (1975)). During hyperglycemia, about 50% of the volume regulatory increase was found to consist of electrolytes, a small amount of glucose, and idiogenic osmoles (Arieff, A. I. et al., 1973, 1977, supra). The exact nature of all these osmoles was not determined, though they were not likely to be amino acids. The increment of idiogenic osmoles appeared to be the consequence of hyperglycemia and not hyperosmolality, because a comparable increase in osmolality with glycerol, sucrose, or mannitol did not generate idiogenic osmoles and did not cause a volume regulatory increase. The lack of volume regulation in response to glycerol, sucrose, and mannitol accounts for their usefulness in reducing brain volume in patients with cerebral edema (Culpepper, R. M. et al., supra).

In contrast to the amino acids that accumulate during hypernatremic states, the "idiogenic" osmoles of hyperglycemia disappeared rapidly as the plasma glucose fell (Arieff, A. I. et al., 1973, 1977, supra). Thus, rapid reduction in plasma glucose in hyperglycemic hyperosmolar coma leads to rapid and progressive improvement in the comatose state whereas comparably rapid reduction in serum osmolality to normal in hypernatremic states can precipitate convulsions.

More recently, it was shown that chronic hypernatremia resulted in generation of idiogenic osmoles which, in addition to electrolytes, accounted for cellular osmolality. In rats made hypernatremic by NaCl injection and water restriction, myo-inositol increased in brain and kidney and sorbitol increased in the kidney. Water content was unchanged. The authors concluded that polyols play a significant role in brain and kidney cellular osmoregulation (Lohr, J. W. et al., *Life Sci.* 43:271-276 (1988). Nakanishi, T. et al. (*Am. J. Physiol.* 255:C181-C191 (1988)) surveyed several renal-derived cell lines for their ability to survive in vitro under high concentrations of NaCl and urea, and for the accumulation of organic osmolytes. The same osmolytes which are found in renal IM were accumulated by several of the cell lines growing in vitro. For example, cells of the MDCK cell line, which proliferated in hyperosmotic medium, contained higher levels of myo-inositol, GPC, and betaine than they did in iso-osmotic medium. MDCK cells accumulated myo-inositol in response to hyperosmolality via a high affinity myo-inositol transporter, the level of which increased in response to high salt (Nakanishi, T. et al. (*Proc. Natl. Acad. Sci. USA* 86:6002-6 (1989)).

If the initial acute hypernatremia insult is severe, a subject can die without evidence of volume regulation. A partial explanation for this comes from the demonstration that the tight junctions of the endothelial cells that restrict intercellular diffusion of ions, proteins, and water-soluble nonelectrolytes, can be opened by osmotically induced shrinkage of the endothelial cells of the BBB (Rapaport, S. I. et al., *Ann. N.Y. Acad. Sci.* 481:250-267 (1986)). The more water-soluble the solute and the higher its reflection coefficient, the more it is able to "open" the BBB when in contact with the endothelium at hypertonic concentrations (for example, molar). This "opening" of the BBB would leave the brain tissue unprotected.

Examination of the brains of humans and animals following severe acute hyperosmolar salt loads revealed normal or shrunken brains, severely engorged vessels, capillary rupture and petechial hemorrhages, and larger parenchymal and subarachnoid bleeding. This damage usually was associated with plasma osmolalities of 350 to 450 mosm/liter (Fineberg, L., *Pediatrics* 23:40-48 (1958); Fineberg, L. et al., *Pediatrics* 23:46-53 (1959)). The mortality rate in patients with hyperosmolality of this severity can exceed 50% (Arieff, A. I. (1987), supra). In humans and animals, the more chronic the development of hypernatremia and the less extreme the hypertonicity (serum sodium less than 160 mEq/liter), the less symptomatic the subject and the lower the mortality rate. .

In the treatment of human hypernatremia, the rate of return of serum sodium to normal should be a function of the severity and the rapidity of its development. In a patient who developed hypernatremia over 4 hours, for example, it is probable that little volume regulation took place. Thus, the serum sodium probably could be returned to normal over, at most, a 12 to 24 hour period without fear of adverse CNS reactions. On the other hand, if the duration of the hypernatremic state is unknown, especially when serum sodium is above 160 mEq/liter, it is suggested that correction should be extended over 2 to 4 days. Arieff (Arieff, A. I. (1987), supra) suggested that correction take place over at least 48 hours, or at a rate of decrease of serum osmolality of 2 mosm/kg/hour.

The longer the duration of the hypernatremic state, the more likely that volume regulation will be complete; that is, the brain cell content of solutes is increased and brain volume is normal. Too rapid a correction of hypernatremia by free water administration at this time will result in overexpansion of the cell volume and possibly cerebral edema. Time is required for the volume regulatory effects on the brain to dissipate. Slow correction should be the password, e.g., a rate of reduction of serum osmolality and serum sodium of about 1 mosm/kg and 0.5 mEq/liter per hour, respectively.

Current treatment of osmotic disturbances, such as those discussed above is confined to the infusion of salt solutions, such as sodium chloride, in an attempt to correct serum sodium levels or serum osmolality. The solutes present in these solutions have the disadvantage of adversely affecting cells. These salt solutions do not contain organic osmolytes, which are known to be non-perturbing and/or "counteracting" solutes, and which, in contrast to electrolytes such as NaCl, are generally considered non-toxic (Yancey, P. H. et al., supra).

Parenteral nutrition solutions, on the other hand, have been designed to meet nutritional needs. Although these fluids do contain some osmolytes, especially amino acids, they are not formulated to treat osmotic disturbances. The concentrations of organic osmolytes in these solutions is not sufficient for their function in the correction of osmotic disturbances. Thus, the use of solutions containing organic osmolytes to treat osmotic disturbances is not known in the art.

BRIEF SUMMARY OF THE INVENTION

The novelty of this invention lies in the use of organic osmolyte compounds to treat osmotic disturbances. Currently, NaCl solution is used in such situations. In general, exogenous fluids given intravenously and dialysis fluids are associated with many untoward side effects. There have been few major advances in the improvement of such fluids in recent years. The inventors, in their investigation of the concentration of organic osmolytes in various tissues, especially kidney and brain, under hyper- or hypoosmotic conditions, have made the discovery that many of these osmolytes are useful alone, in combination, or as additives to existing solutions, in the treatment of osmotic disturbances.

This invention is directed to a method to treat an osmotic disturbance in an animal comprising providing to the animal an effective concentration of an organic osmolyte compound.

The invention is also directed to a method to treat an osmotic disturbance in an animal comprising providing to the animal an effective concentration of a precursor of an organic osmolyte compound.

The organic osmolyte compounds useful in this invention include, but are not limited to, three major classes of compounds: polyols (polyhydric alcohols), methylamines, and amino acids. The polyols considered useful in the practice of this invention include, but are not limited to, myo-inositol, and sorbitol. The methylamines of the invention include, but are not limited to, choline, betaine, phosphorylcholine, glycerophosphorylcholine, creatine, and creatine phosphate. The amino acids of the invention include, but are not limited to, glycine, alanine, glutamine, glutamate, aspartate, proline and taurine.

The osmolyte precursors of this invention include, but are not limited to, glucose, glycerol, choline, phosphatidylcholine, and inorganic phosphates, which are direct precursors of polyols and methylamines, and to proteins, peptides, and polyamino acids which are precursors of amino acid osmolytes.

This invention comprises selected organic osmolytes or their precursors in combinations and concentrations calculated to provide cells with the appropriate milieu for intact osmoregulation. The osmolytes of this invention are added as supplements to fluids administered enterally or parenterally. Since these compounds have been shown by the inventors and by others to have intracellular osmoprotective effects, especially in kidneys and brain, their administration protects subjects from cellular dehydration which is especially important in the treatment of hyponatremia and acute hypernatremia.

Osmolyte concentrations in the fluids of the invention are in the range of about 0.01 to 4000 mM when used to supplement saline or in other standard solutions. Preferably, the osmolyte concentration is between about 0.1 and 1500 mM. A solution comprised entirely of one or more organic osmolytes may contain concentrations as high as 4 M. It is understood that the concentration of one or more osmolytes in a solution of the invention will vary depending upon the other constituents of the solution, and the particular purpose for which the solution is formulated.

The invention is directed to the treatment of osmotic disturbances substantially associated with acute hyponatremia, chronic hyponatremia, central pontine myelinolysis associated with hyponatremia, diabetic ketoacidosis, acute hypernatremia, hyperglycemic hyperosmolar coma, chronic uremia, chronic hypernatremia, including accidental salt loading in high sodium dialysis or baby formula, alcoholism-related dehydration, diabetes insipidus, diabetes mellitus, AIDS, or dehydration from other causes.

This invention is also directed to treatment of osmotic disturbances associated with renal dialysis comprising addition to a dialysis fluid of an effective concentration of an organic osmolyte.

2A: $^1$H-NMR spectrum of renal inner medulla (IM) from a dehydrated rat.

2B: An expanded view of A, highlighting region (2.9-4.5 ppm) containing glycerophosphorylcholine (GPC), betaine, and myoinositol.

2C: $^1$H-NMR spectrum of a standard sample that contained only GPC (27 μmol), betaine (16 μmol), and myo-inositol (14 μmol).

These spectra are sums of 64 transients each and are referenced to sodium 3-trimethylsilylproprionate-2,2,3,3-d$_4$ (TSP). Base line "noise" in 2B and 2C differs because it was scaled differently to compensate for higher osmolyte contents in the standard.

FIG. 3A & 3B Osmolyte contents of renal IM from control and dehydrated kidneys. Osmolytes are quantitated. 3A: per protein, and 3B: per wet weight. Ninhydrin-positive substances (NPS) indicate amino acid content. *$p<0.05$, $p<0.02$, *$p<0.002$, ****$p<0.001$. GPC, glycerophosphorylcholine.

Figure 4:
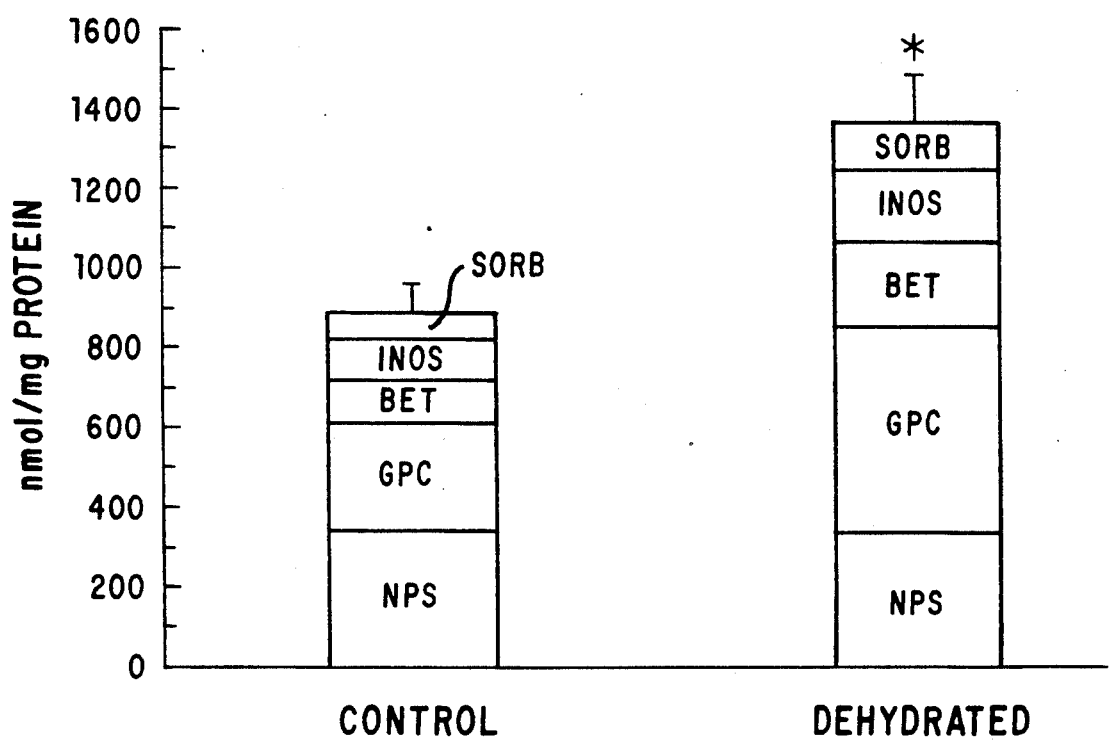

FIG. 4 Total and individual osmolyte contents of renal inner medullas from control (n=9) and dehydrated (n=13) rats. Bet, betaine; GPC, glycerophosphorylcholine; Inos, myo-inositol; NPS, ninhydrin-positive substances; Sorb, sorbitol. *$p<0.01$.

Figure 5:
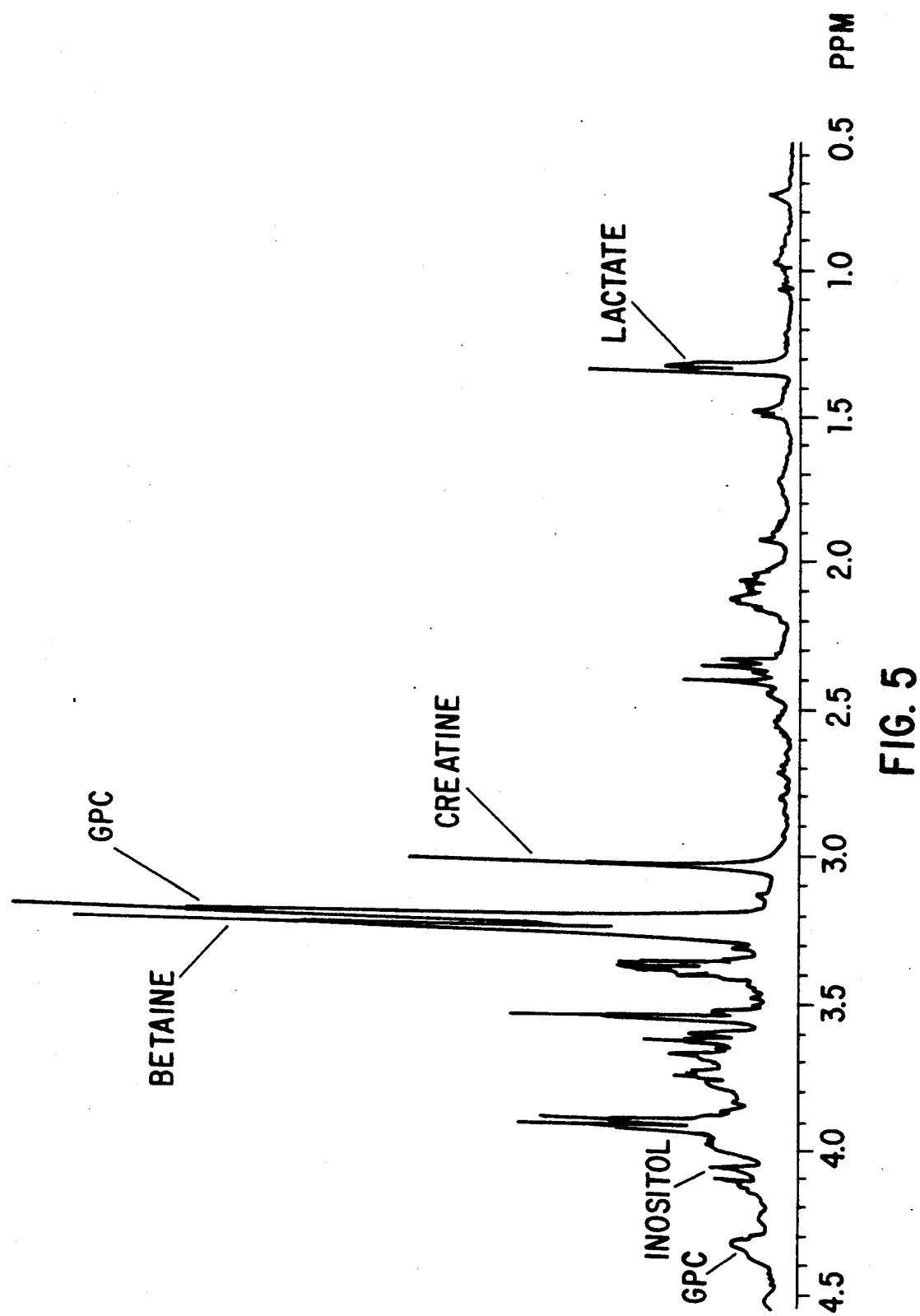

FIG. 5. $^1$H.NMR spectrum of a renal cortex from a dehydrated rat. Spectrum was sum of 64 transients and was referenced to sodium 3-trimethylsilylproprionate-2,2,3,3-d$_4$ (TSP). For clarity only peaks identified as osmolytes have been labeled. GPC, glycerophosphorylcholine.

Figure 6A:
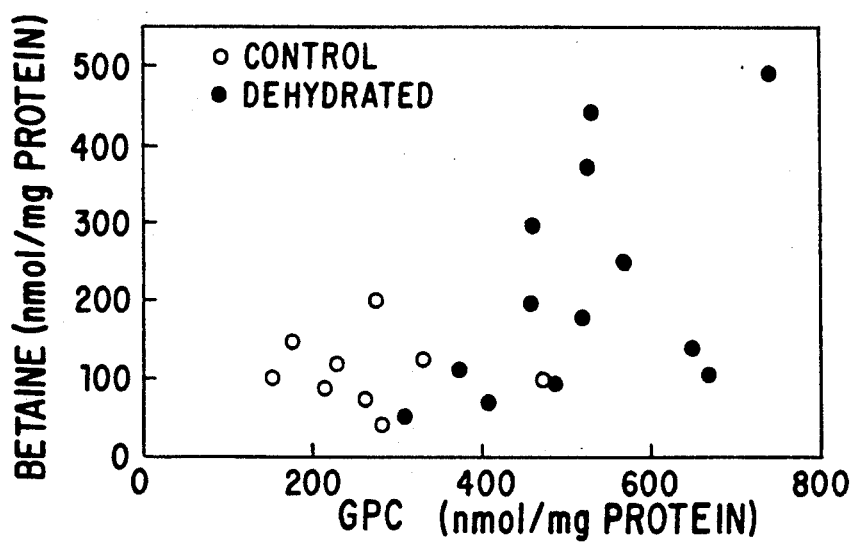
Figure 6B:
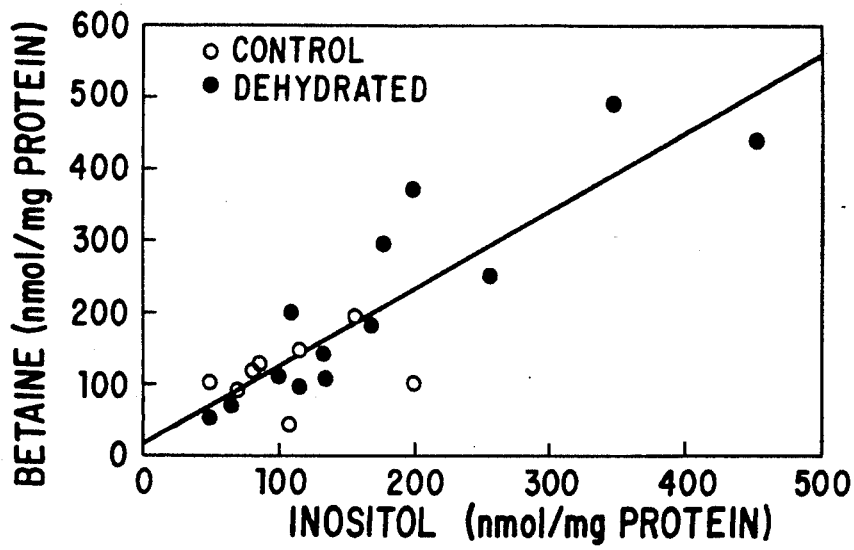
Figure 6C:
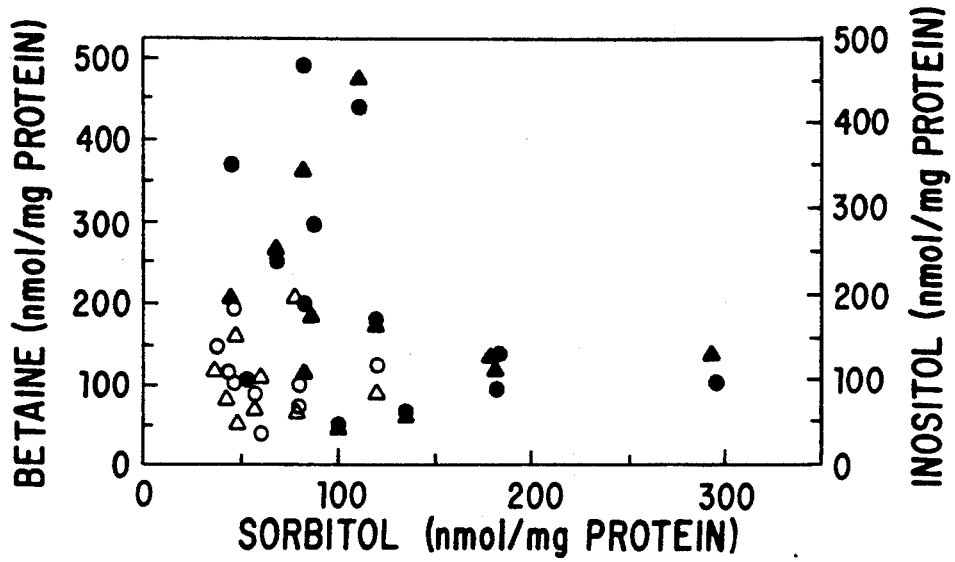

FIG. 6A, 6B & 6C Correlations among osmolytes in renal IM. Each point represents the osmolyte content measured in a single extract. Each extract was prepared from inner medullas of 2 or 4 kidneys obtained from 1 or 2 rats, respectively.

6A: Correlation between betaine and GPC.

6B: Strong linear correlation (r=0.87) between betaine and myoinositol, which is described by the equation, [betaine]=1.1×[myo-inositol]+11. Intercept of this line is not different from zero.

6C: Betaine levels from control (open circles) and dehydrated (closed circles) rats, respectively; myo-inositol content of control (open triangles) and dehydrated (closed triangles) rats, respectively.

Figure 7:
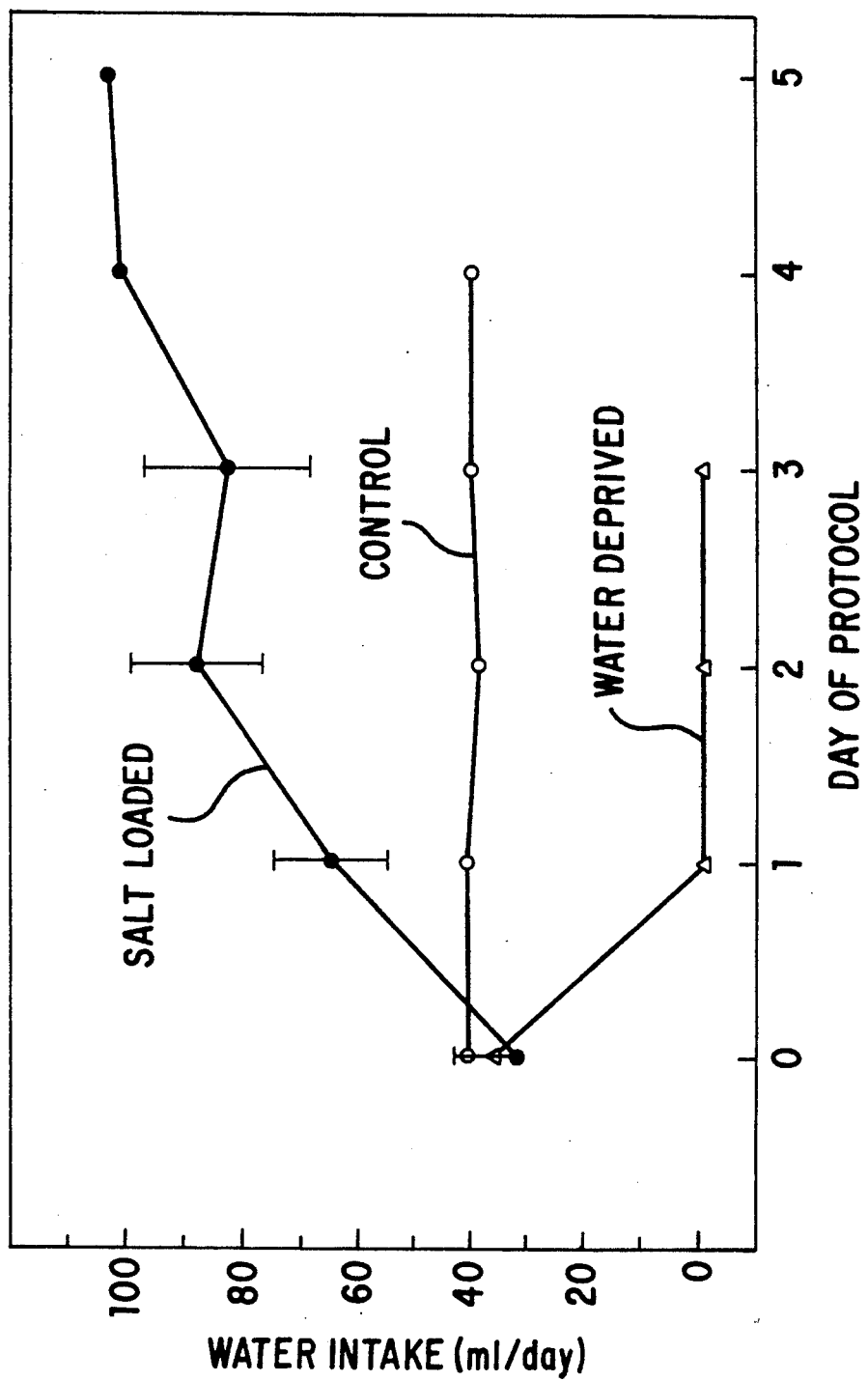

FIG. 7. Water intakes were measured daily in subgroups of rats in each of three experimental protocols: Control (n=4), salt-loaded (n=5), and water-deprived (n=4). Salt-loaded rats drank significantly more water (i.e., 320 mM NaCl) than control rats (tap water) on every day after day 1 ($p<0.01$). They rapidly achieved a stable intake of 80-100 ml/day on days 2-5. Water-deprived rats had their water bottles removed for the duration of the study. When not visible, error bars were contained within the data point.

Figure 8:
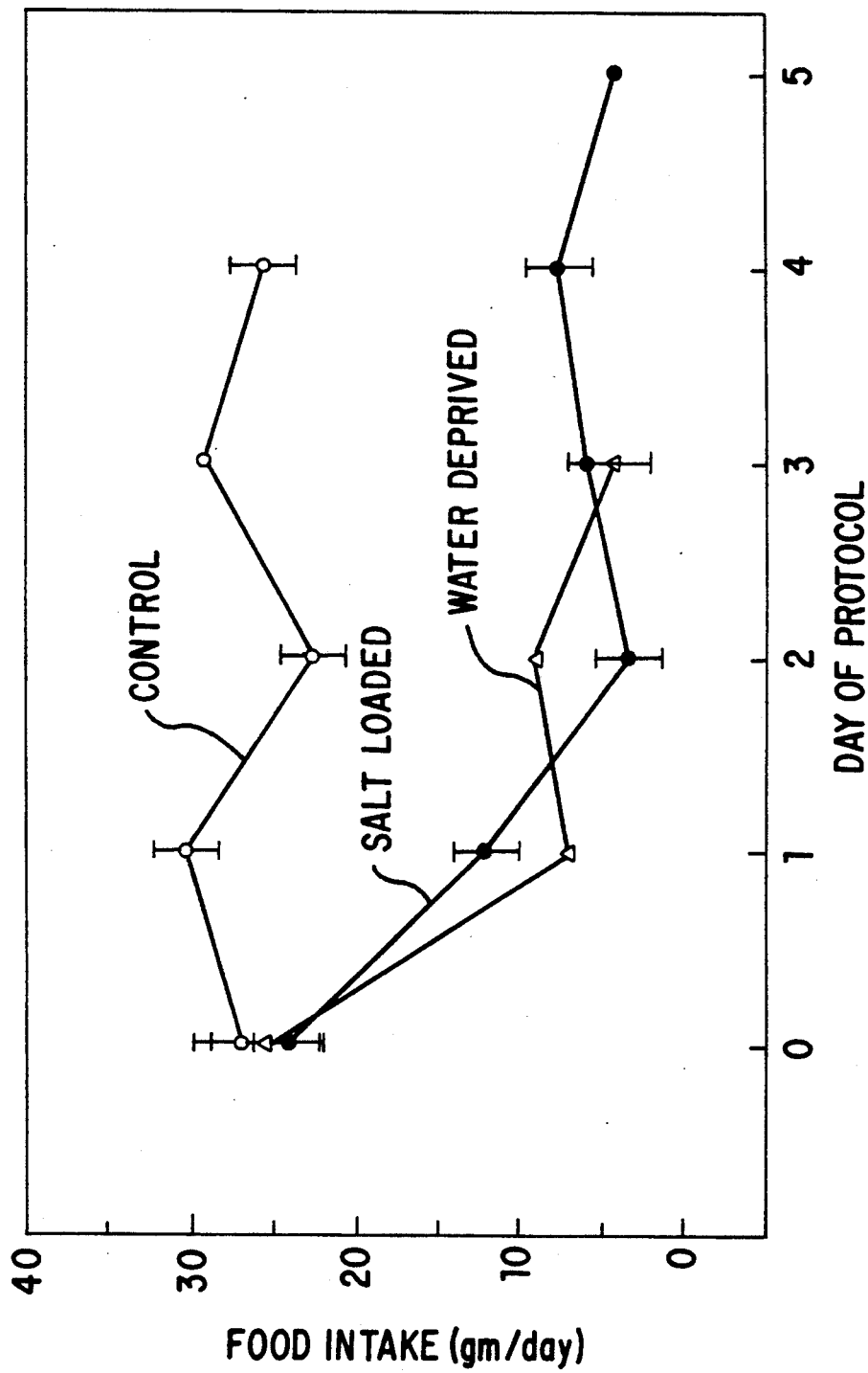

FIG. 8. Food intakes were measured daily in subgroups of rats from each of the three experimental protocols. Both salt-loaded and water-deprived rats ate significantly less food than controls after day 0 ($p<0.001$). At the end of their respective protocols, salt-loaded and water-deprived rats consumed approximately 81% less food than the control rats. When not visible, error bars were contained within the data point.

Figure 9:
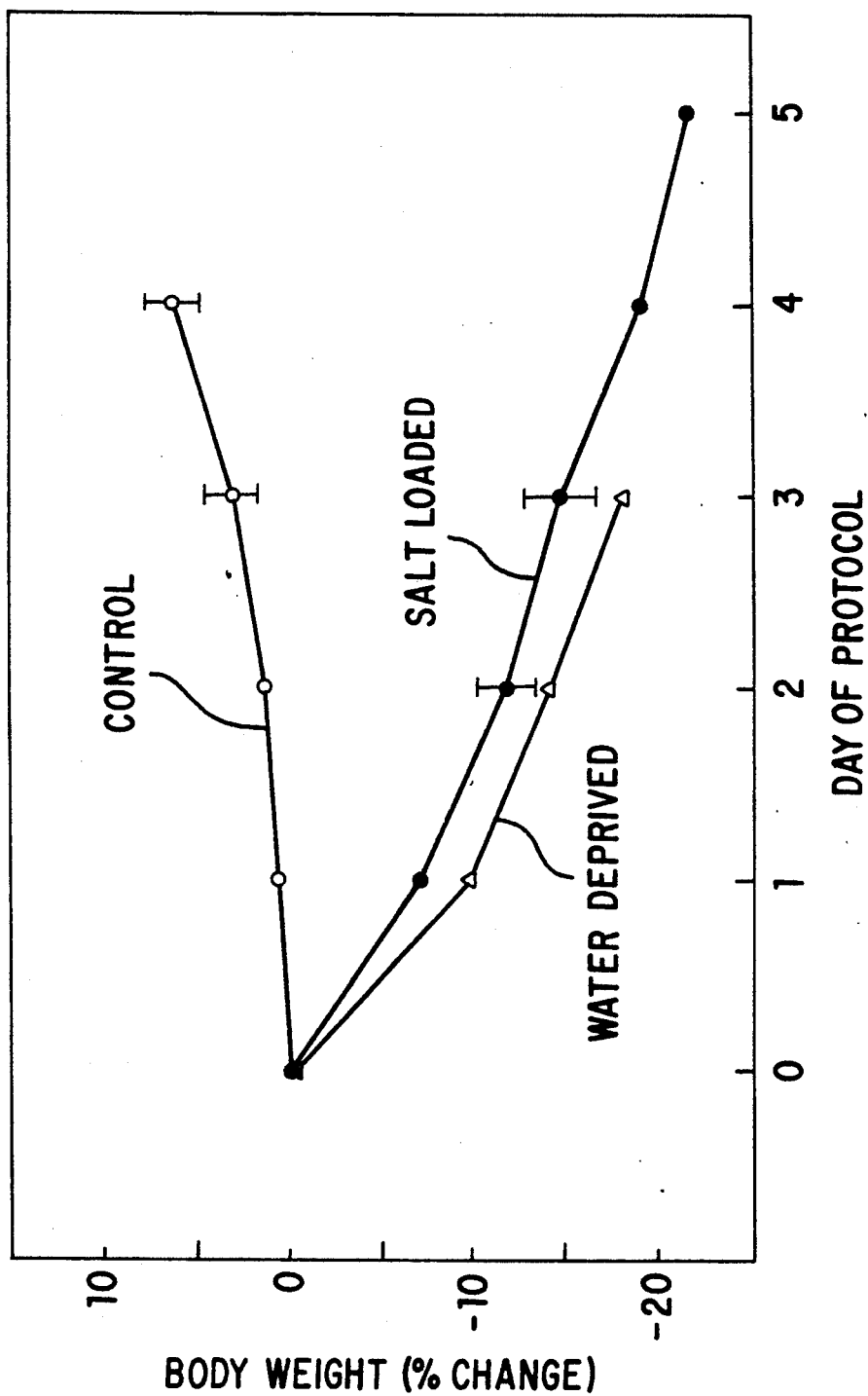

FIG. 9. Cumulative percent changes in daily body weight are depicted for subgroups of rats in each of the three protocols. Body weights of control rats increased 6% during the protocol ($p<0.05$), whereas salt-loaded and water-deprived rats exhibited significant descreases on days 1-5 ($p<0.05$). Percent change in body weight for salt-loaded and water-deprived rats were similar throughout their respective protocols. When not visible, error bars were contained within the data point.

Figure 10:
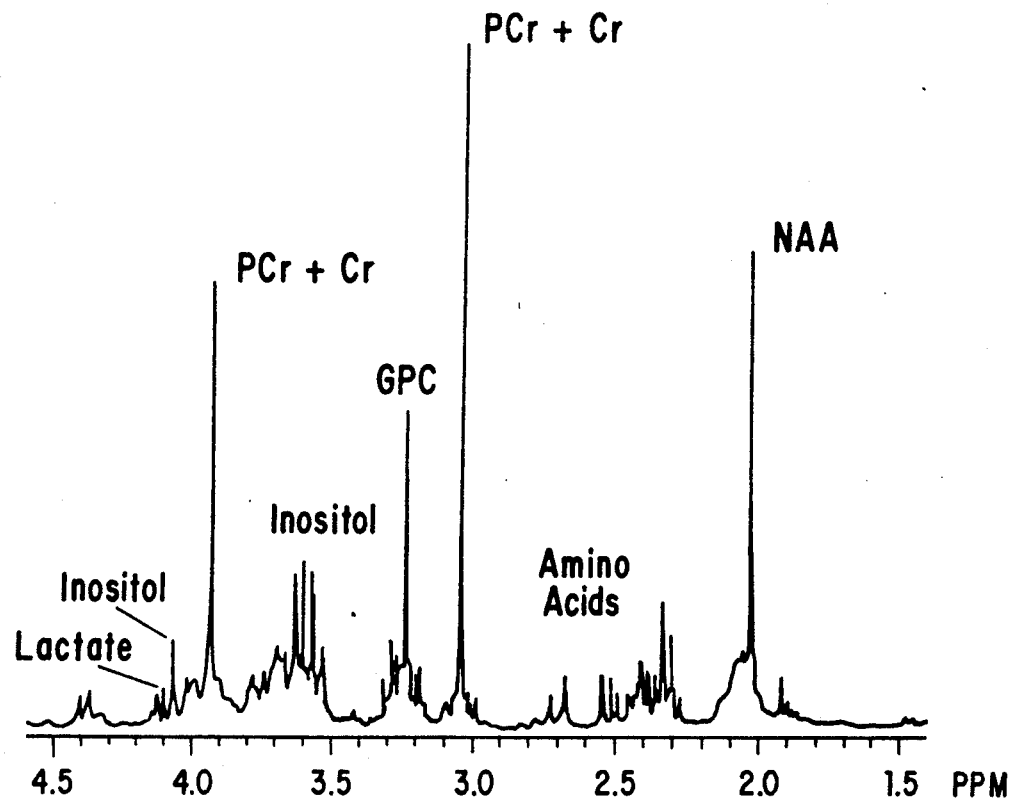

FIG. 10. A typical $^1$H NMR spectrum of a PCA extract of brain from a salt-loaded rat. The portion of the spectrum which included the compounds of interest (amino acids, methylamines, and polyols) is depicted at 1.5-4.5 ppm. Characteristic and prominent peaks (resonances) for phosphocreatine+creatine (PCr+Cr) and NAA are seen at 3.04 and 2.02 ppm respectively. Also labeled are peaks representing GPC, amino acids, myo-inositol and lactate.

Figure 11:
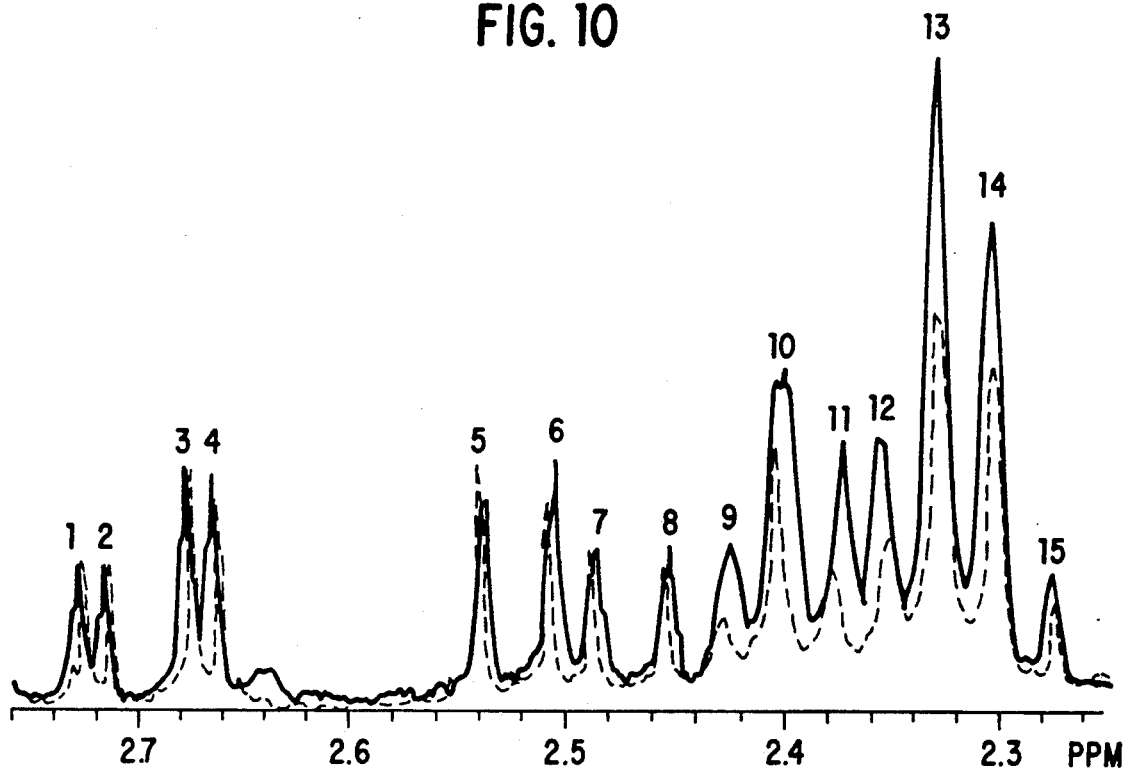

FIG. 11. Representative $^1$H NMR spectra of PCA extracts of brain for control (dashed line) and salt-loaded (solid line) rats. This is an expanded view of the region 2.25 to 2.76 ppm which contains multiple amino acid peaks. Spectra of water-deprived rats (not shown) were comparable to spectra of control rats. Peaks 1-8 represent NAA. Peaks 9, 10 and represent glutamine, and peaks 12, 13 and 14 represent glutamate. As shown, both glutamine and glutamate were elevated in brain of salt-loaded rats vs. controls. Peak 15 represents GABA which was unchanged.

Figure 12:
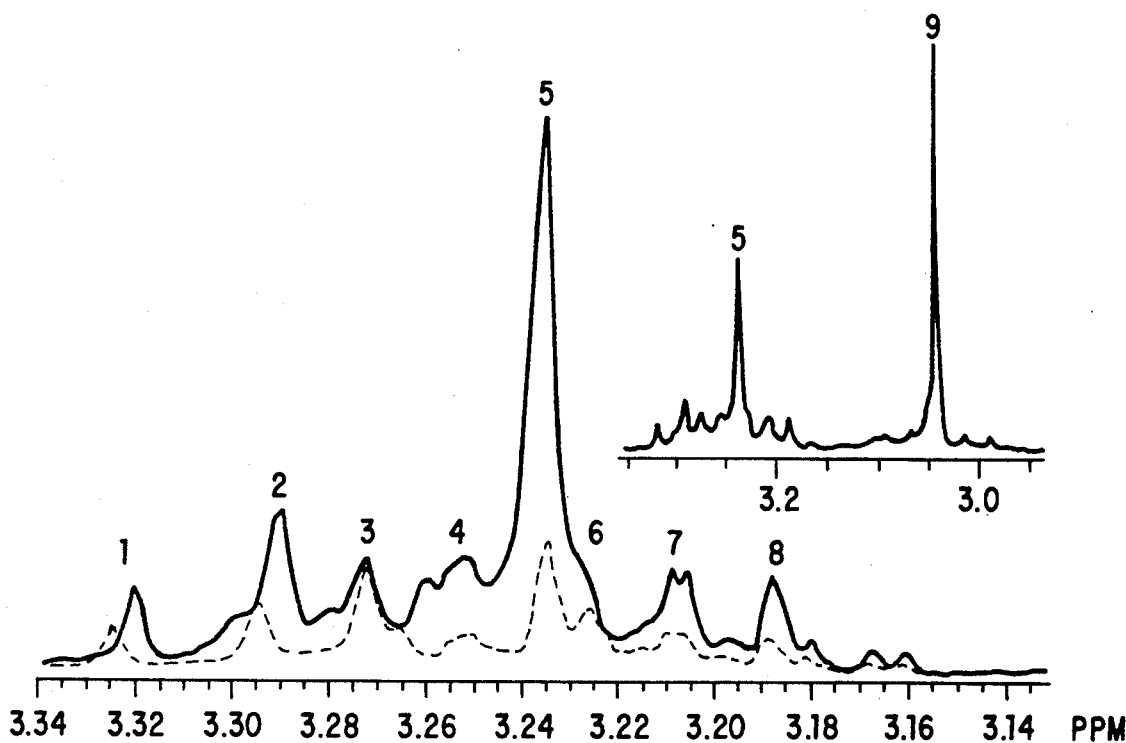

FIG. 12. Representative $^1$H NMR spectra from brain of control (dashed line) and salt-loaded (solid line) rats. The inset is from a salt-loaded rat indicating the relative abundance of GPC (peak 5) and PCr+Cr (peak 9). The expanded region (3.14 to 3.34 ppm) contains peaks representing myo-inositol and methyl protons of methylamines. Slight shifts in peak positions are seen due to differences in ionic strength of individual extracts. Spectra from brain of water-deprived rats were comparable to spectra from control rats. Peaks 1, 2 and 4 represent myo-inositol which was elevated in the brain of salt-loaded rats. Betaine (peak 3), GPC (peak 5), PCholine (peak 6) and choline (peak 7) are also detected. Peak 8 is unidentified. Three methylamines, PCr+Cr, GPC and choline were significantly elevated in the brain of salt-loaded rats compared to controls.

Figure 13:
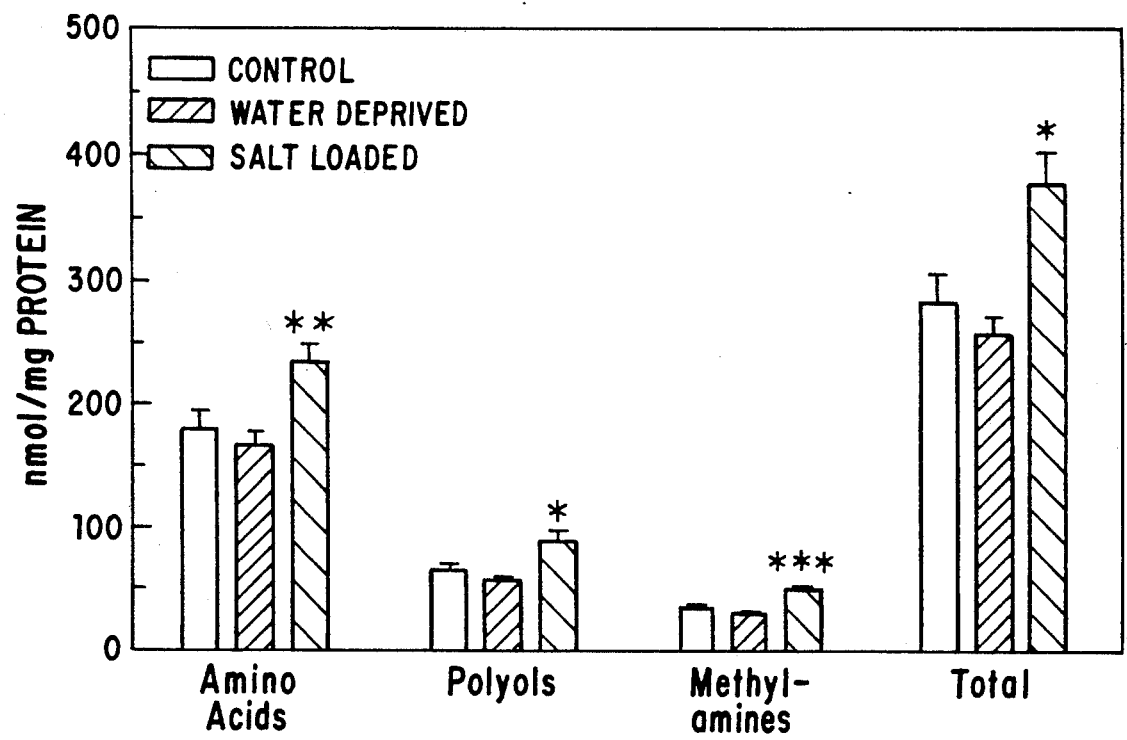

FIG. 13. Total brain amino acids, methylamines, polyols, and total solutes are depicted for each of the three groups of rats. All of the totals were elevated in salt-loaded rats compared to controls. There was no elevation of any of the organic solutes in the brain of water-deprived rats. *$p<0.05$, $p<0.02$, *$p<0.005$.

Figure 14:
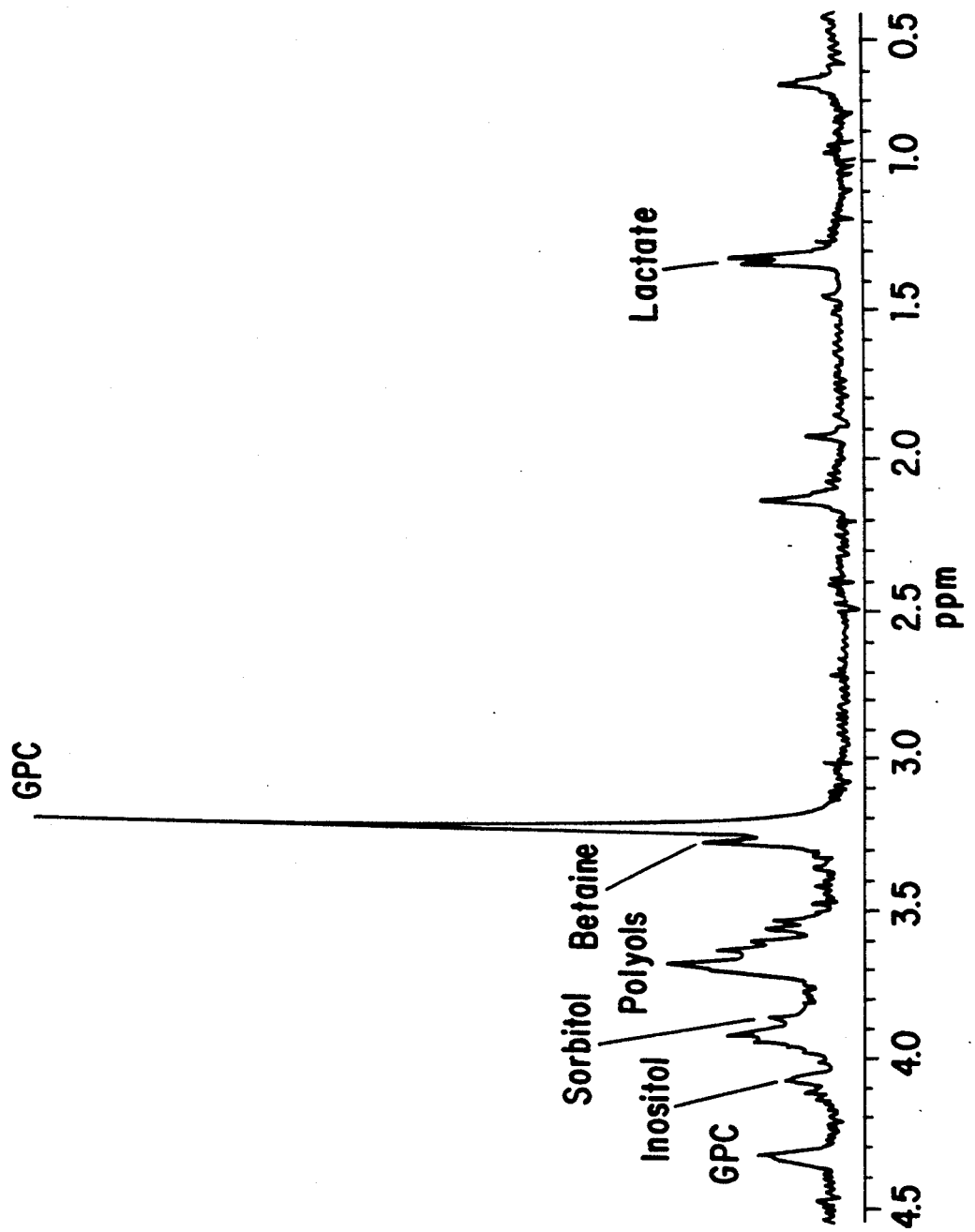

FIG. 14. Typical $^1$H NMR spectrum of a rat renal inner medulla extract (about 50 mg wet weight). Characteristic peaks include protons resonances from GPC, betaine, myo-inositol, and sorbitol. The spectrum is the sum of 128 transients and is referenced to TSP.

Figure 15A:
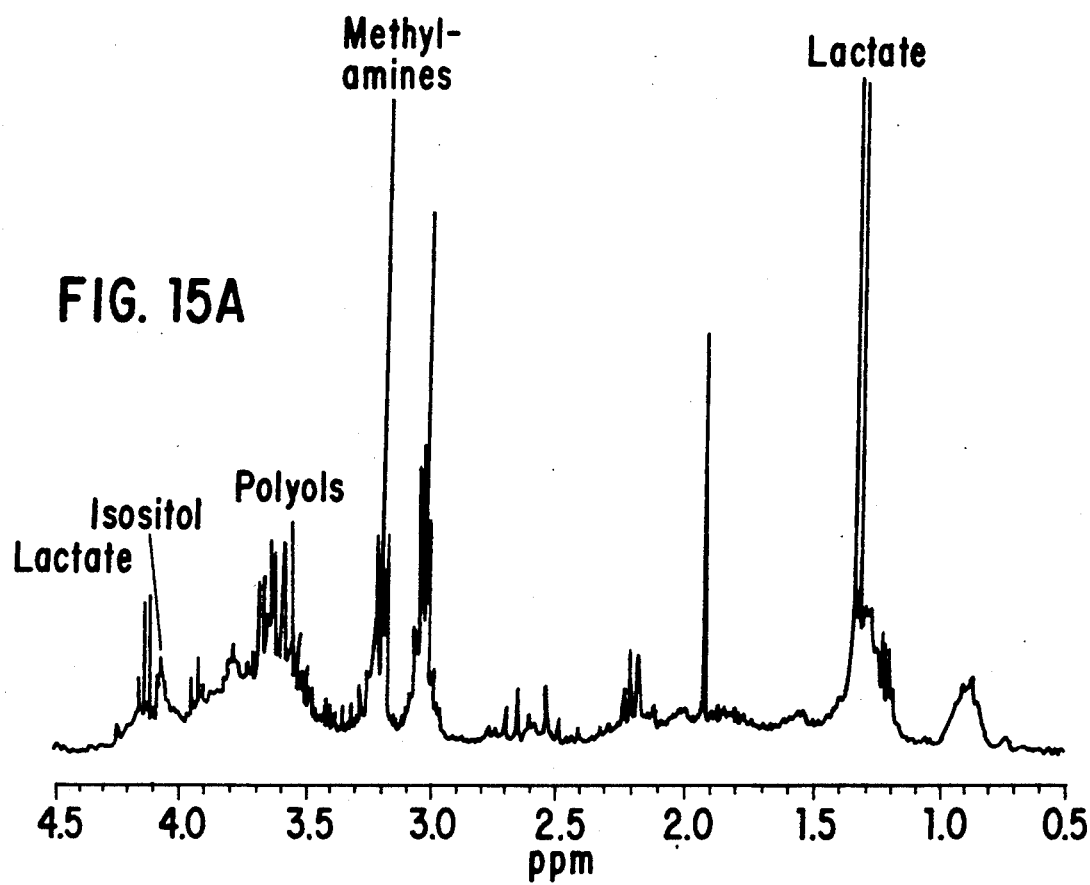
Figure 15B:
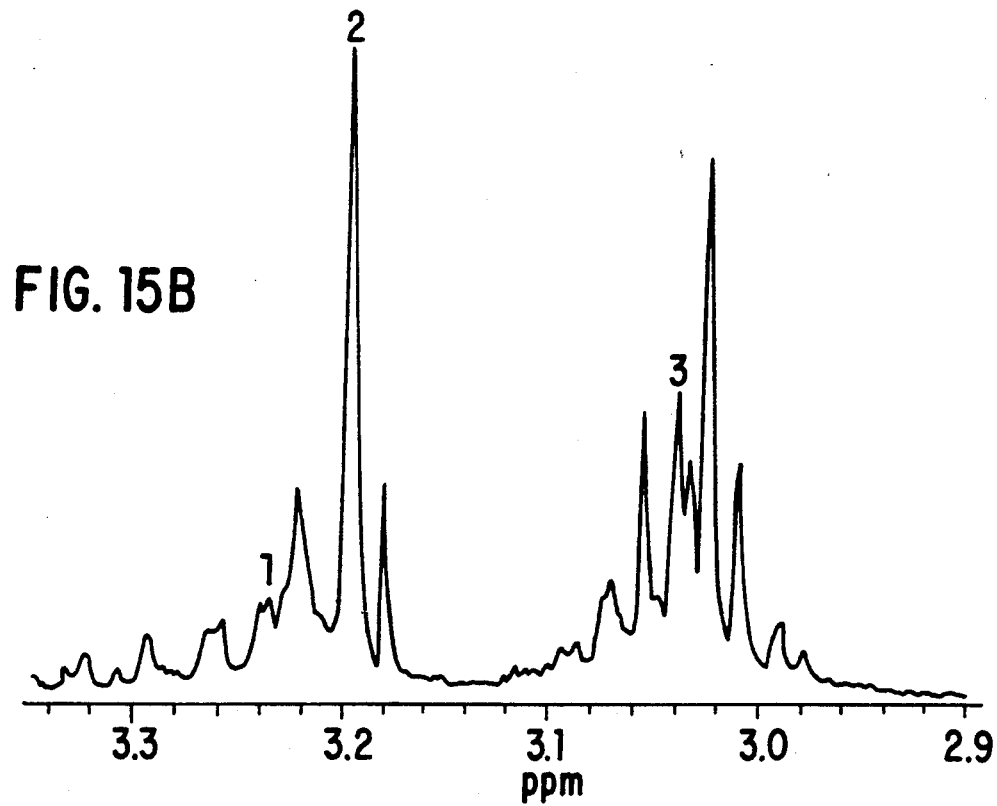

FIG. 15A & 15B. (15A) $^1$H NMR spectrum of rat urinary bladder extract. The spectrum is the sum of 64 transients and is referenced to TSP. (15B) An expanded view of FIG. 15a highlighting the region (2.9-3.35 ppm) containing methylamines. Tentative peak assignments indicate the presence of GPC (peak 1), choline (peak 2), and PCr+Cr (peak 3). These spectra are the sum of 64 transients and are referenced to TSP.

Figure 16:
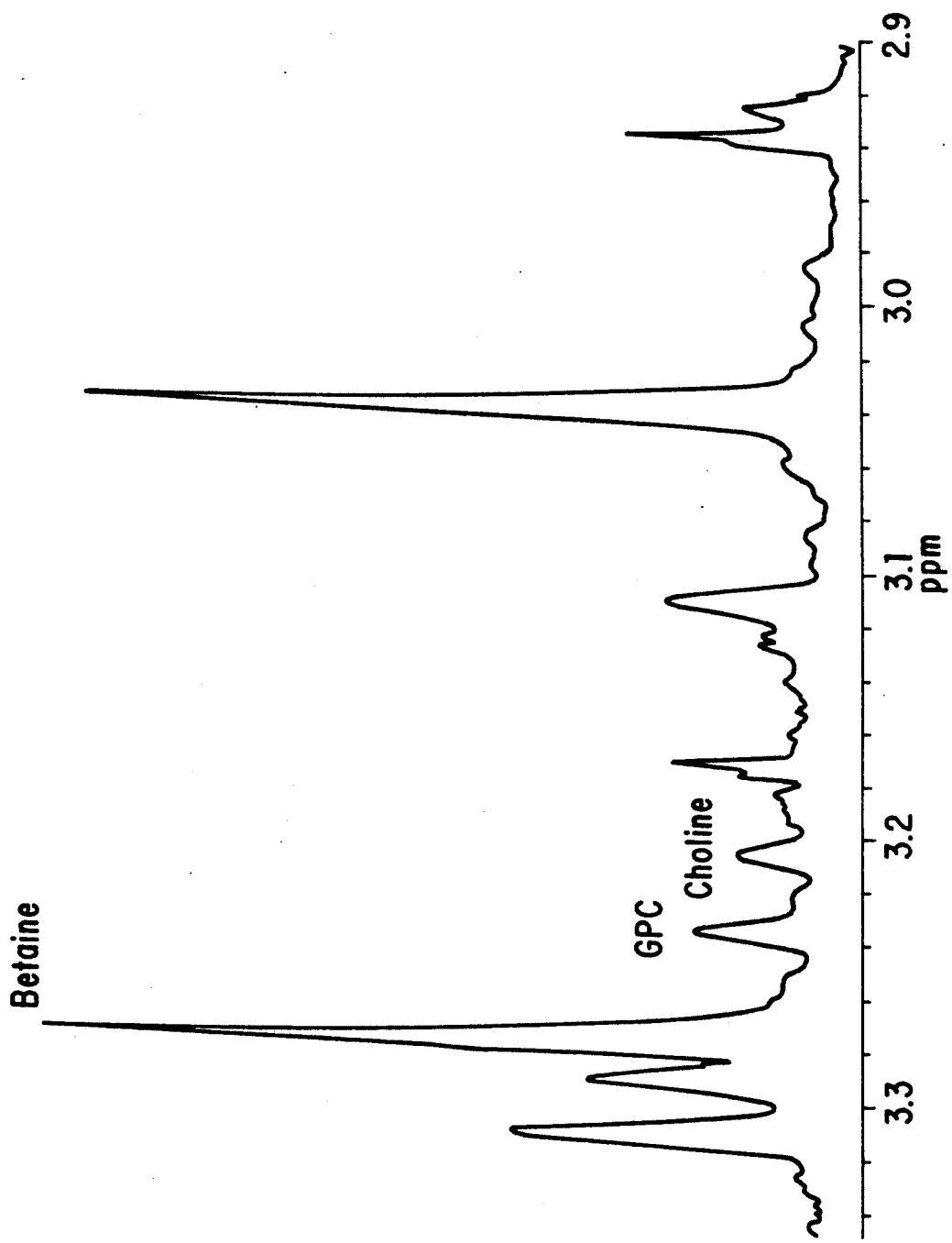

FIG. 16. Typical $^1$H NMR spectrum of rat urine extract. Only the region known to contain methylamines is shown. Betaine was the most abundant organic solute in this spectrum whereas GPC and choline were significantly less abundant. The two peaks to the left of betaine (i.e. downfield) were not myo-inositol because companion peaks were not evident elsewhere in the spectrum. A small quantity of myoinositol could nonetheless lie within these peaks. This spectrum is the sum of 64 transients and is referenced to TSP.

Figure 17:
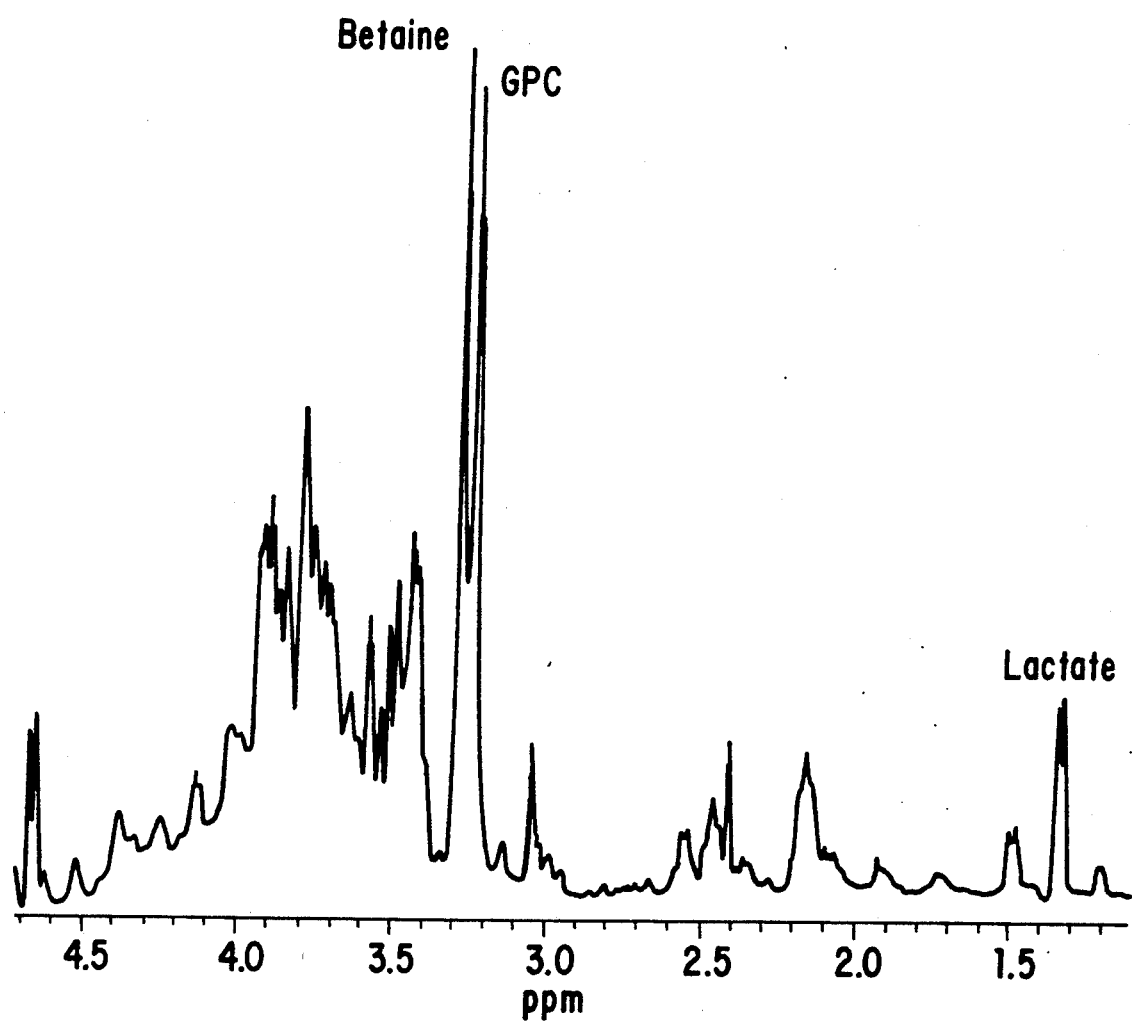

FIG. 17. Typical $^1$H NMR spectrum of rat liver extract (8.2 g wet weight). Betaine and GPC are clearly identified. This spectrum is the sum of 64 transients and is referenced to TSP.

Figure 18:
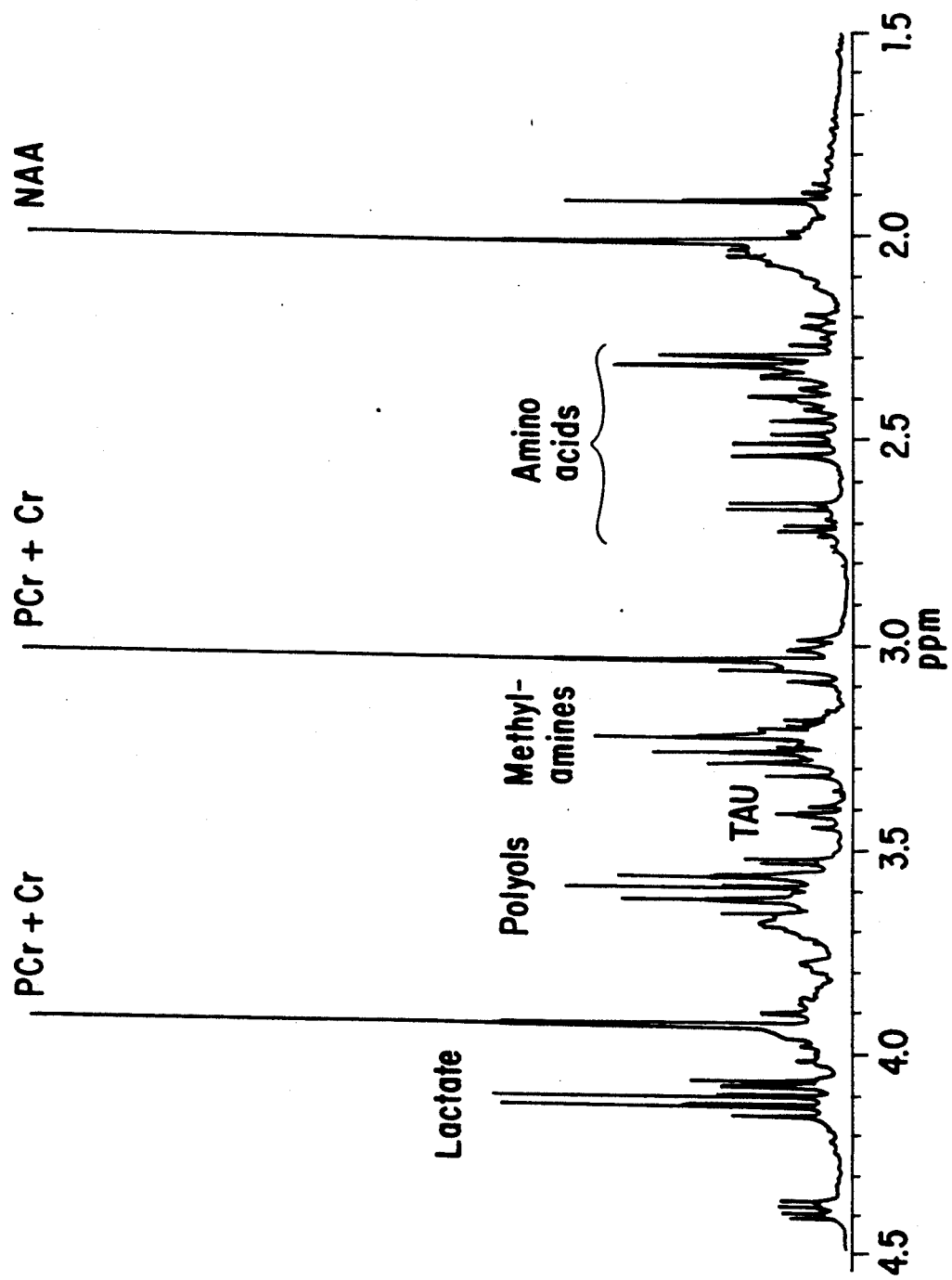

FIG. 18. Typical $^1$H NMR spectrum of rat brain extract (1 g wet weight). Characteristic peaks include proton resonances from N-acetylaspartate (NAA), PCr+Cr, and lactate. In addition, regions known to contain methylamines, polyols, and amino acids are also shown. Taurine (TAU) is also indicated. This spectrum is the sum of 64 transients and is referenced to TSP.

Figure 19:
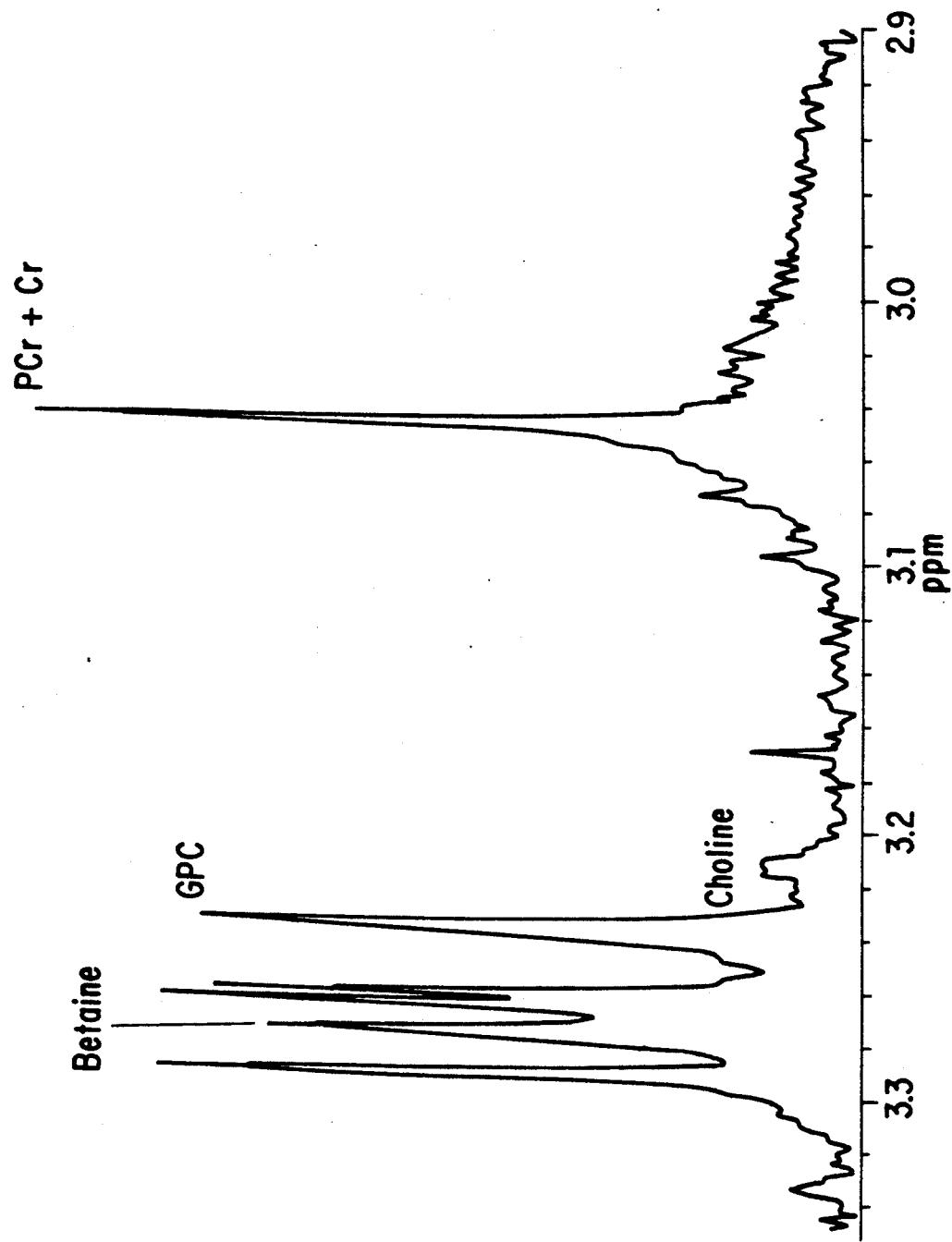

FIG. 19. An expanded view (2.9-3.35 ppm) of a typical $^1$H NMR spectrum of a rat plasma extract. Several methylamines can be observed including betaine, GPC, choline, and PCr+Cr. This spectrum was the sum of 64 transients and is referenced to TSP.

FIGS. 20A-D. Time course of urine excretion parameters in control and salt-loaded rats. Urine volume (20A), sodium concentration (20B), sodium excretion (20C), and osmolality (20D) for subgroups of rats (5 salt-loaded, 4 control) were monitored throughout the study. There were no significant differences in any of these parameters on day 0. Salt-loaded rats had significantly higher urine output, urine sodium concentration, and urine sodium excretion ($p<0.001$) and significantly lower urine osmolality than controls ($p<0.001$) on each subsequent day.

Figure 21:
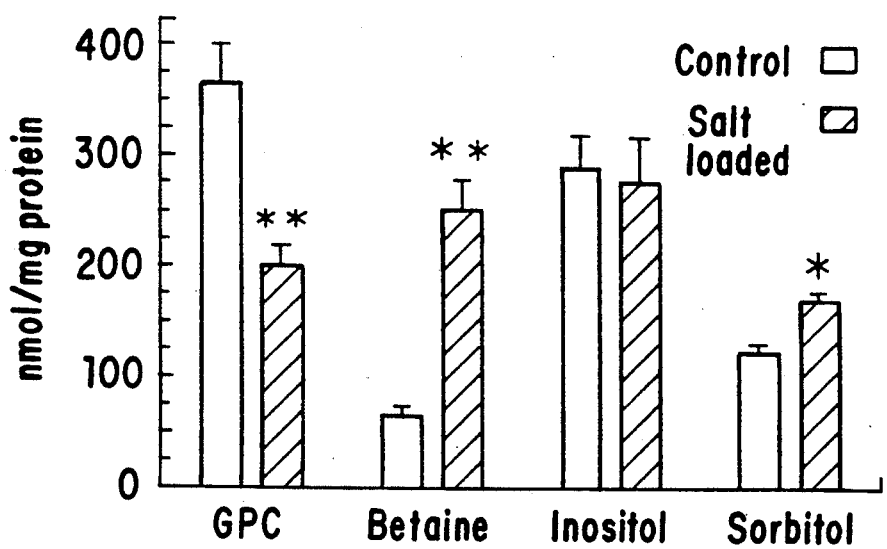

FIG. 21. Renal IM contents of each of 4 major osmolytes in 4 control and 11 salt-loaded rats. Significant changes were observed with salt loading for GPC, betaine, and sorbitol ($p<0.001$).

Figure 22:
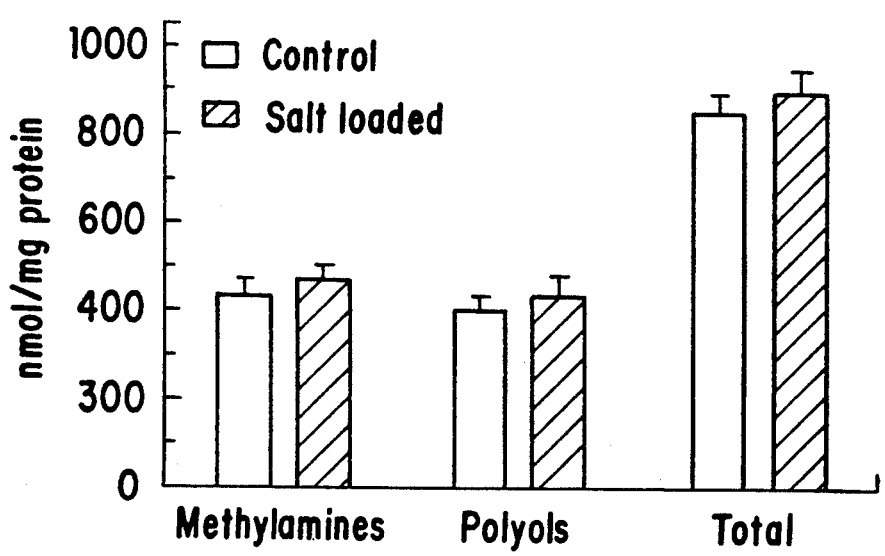

FIG. 22. Total renal IM methylamine, polyol, and osmolyte (sum of GPC+betaine+myo-inositol+sorbitol) contents are depicted for 8 control and 11 salt-loaded rats. No significant differences in totals were observed with salt loading.

Figure 23:
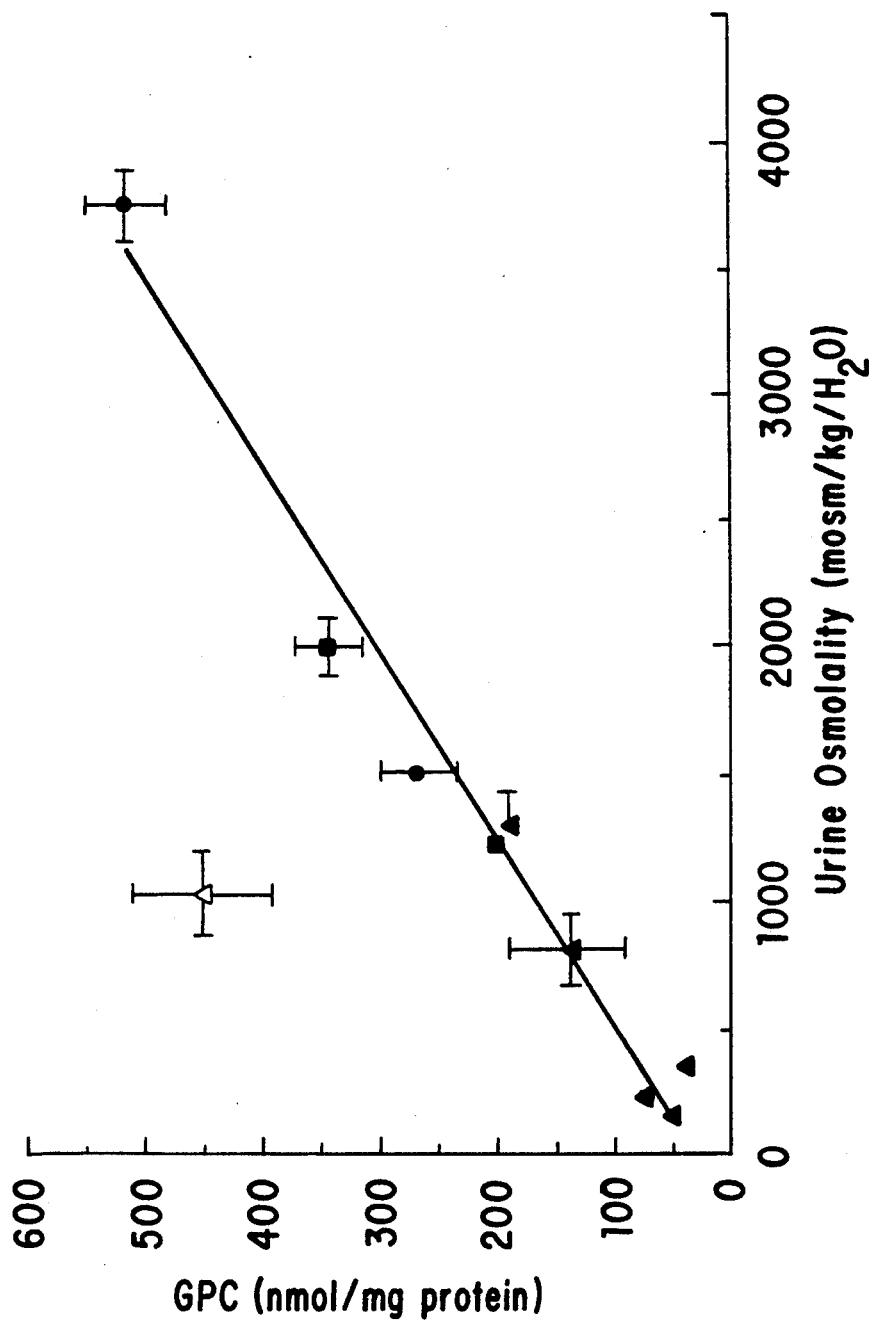

FIG. 23. Significant correlation between urine osmolality and renal IM GPC content from 3 different studies. Triangles, Brattleboro rats; Circles, Wistar-Kyoto rats (Example I); Squares, observations from this study (Example IV). Regression analysis indicated a strong correlation ($r=0.987$, $p<0.001$) with a slope of 0.137 nmol GPC.mg protein$^{-1}$.mosmol$^{-1}$, and an intercept of 33 nmol GPC/mg protein, which not significantly different from origin. The open triangle off the line was excluded from the regression analysis as it was outside 95% confidence interval of regression line.

Figure 24:
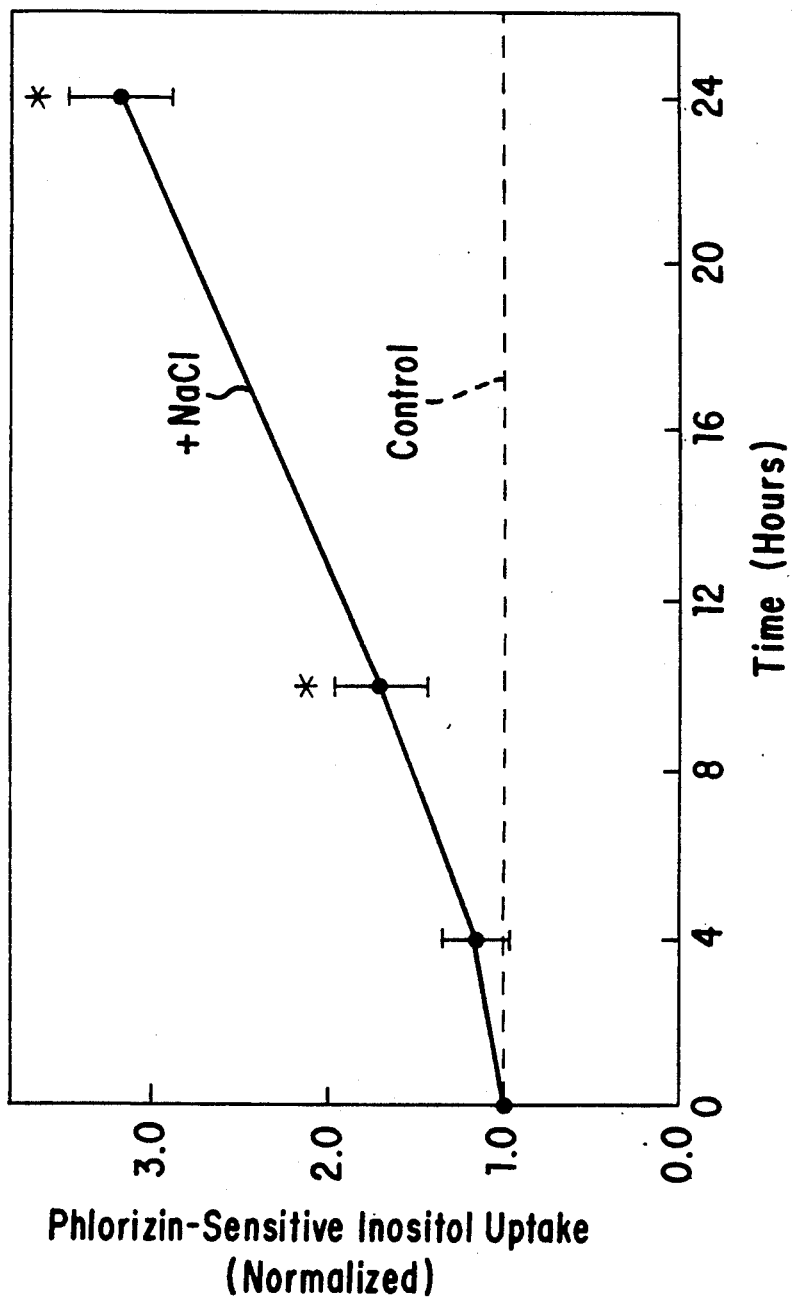

FIG. 24. Myo-inositol accumulation by rat C6 glioma cells in vitro under hyperosmolar conditions (See Example V).

Figure 25:
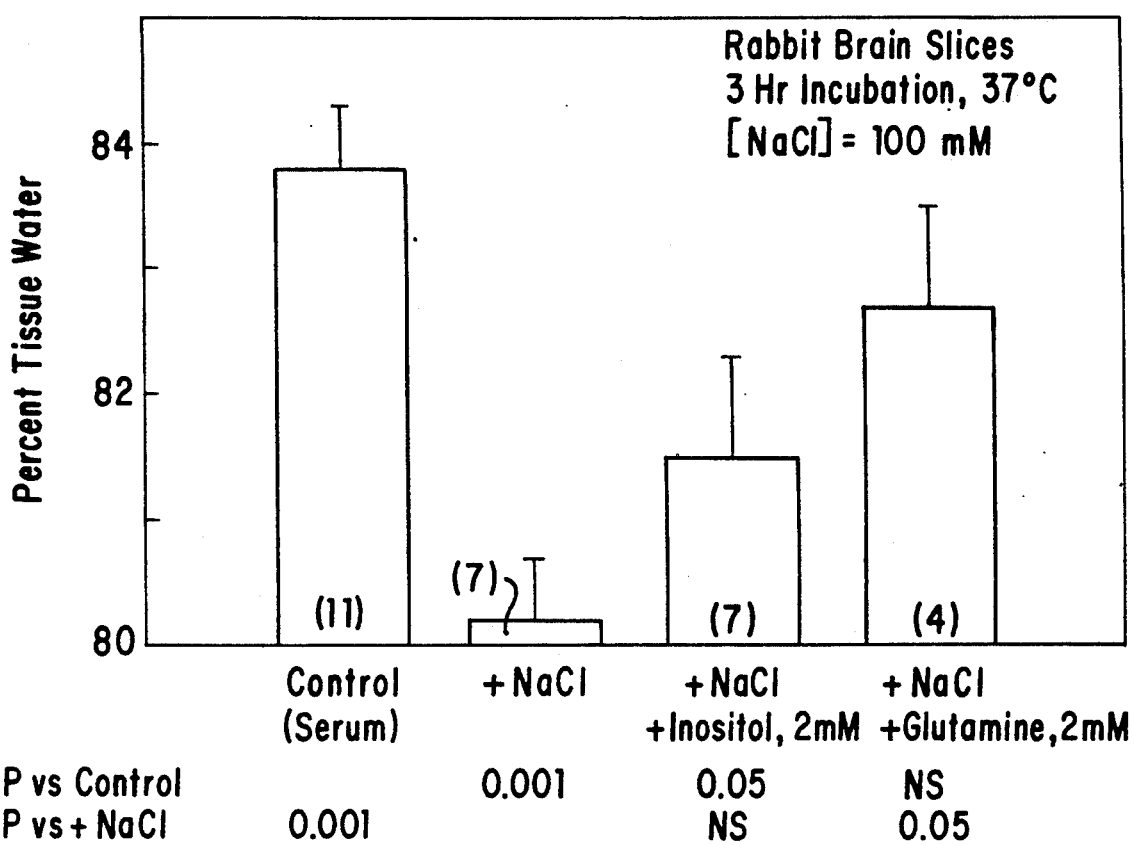
Figure 26A:
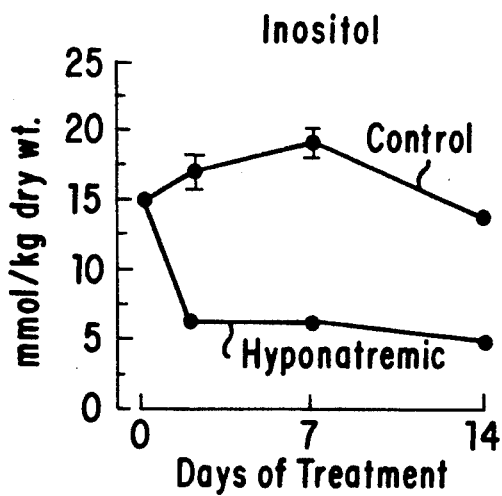
Figure 26B:
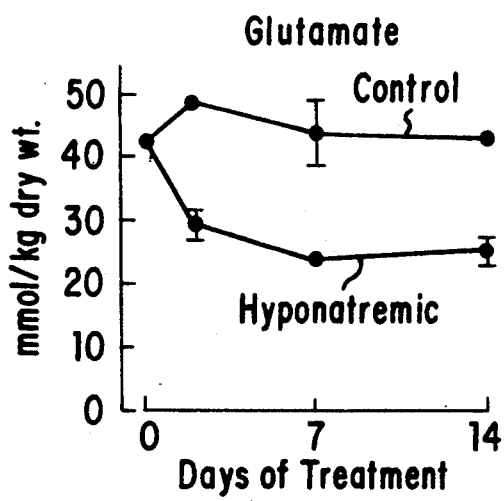
Figure 26C:
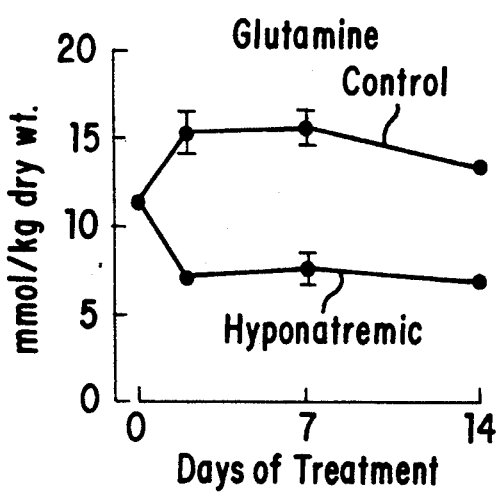
Figure 26D:
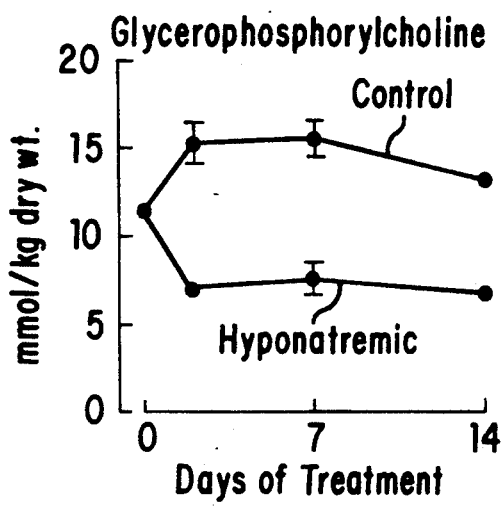
Figure 26E:
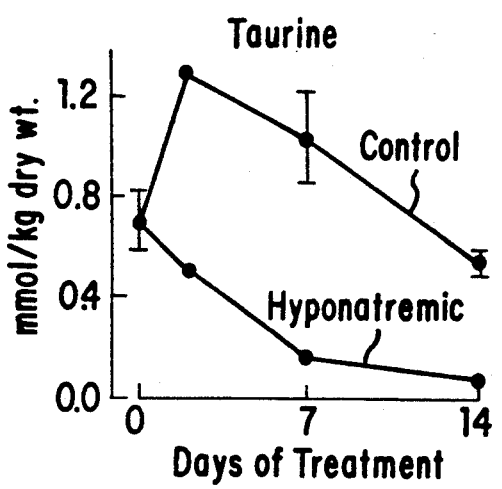
Figure 26F:
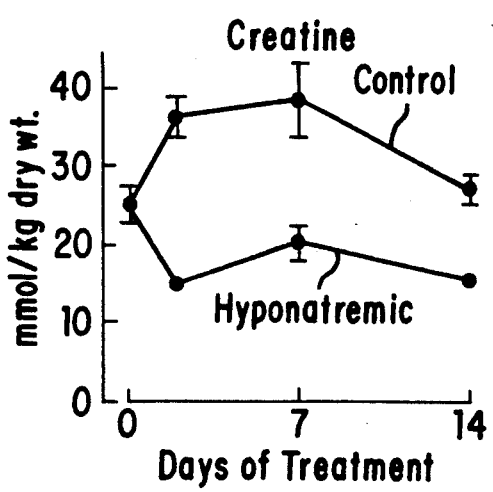

FIG. 25. Restoration of brain tissue water content toward control levels under hypernatremic (+NaCl) conditions with exogenous myoinositol and L-glutamine (See Example VI).

FIG. 26. Reduction in brain osmolytes under hyponatremic conditions. (See Example VII).

DESCRIPTION OF THE PREFERRED EMBODIMENTS

The term "osmolyte" as used herein, refers to a compound which is a solute in body fluids, can circulate in an animal, can enter cells in response to changes in the osmotic milieu, and can protect the cell from damage due to excessive loss or uptake of water. An organic osmolyte is an osmolyte which is an organic compound.

The organic osmolyte compounds useful in this invention include, but are not limited to, three major classes of compounds: polyols (polyhydric alcohols), methylamines, and amino acids. The polyols considered useful in the practice of this invention include, but are not limited to, myo-inositol, and sorbitol. The methylamines of the invention include, but are not limited to, choline, betaine, phosphorylcholine, glycerophosphorylcholine, lyso-glycerophosphorylcholine, creatine, and creatine phosphate. The amino acids of the invention include, but are not limited to, glycine, alanine, glutamine, glutamate, aspartate, proline and taurine.

The term "osmolyte precursor" as used herein refers to a compound which is converted into an osmolyte by a metabolic step, either catabolic or anabolic. The osmolyte precursors of this invention include, but are not limited to, glucose, glucose polymers, glycerol, choline, phosphatidylcholine, lyso-phosphatidylcholine and inorganic phosphates, which are precursors of polyols and methylamines. Precursors of amino acid osmolytes within the scope of this invention include proteins, peptides, and polyamino acids, which are hydrolyzed to yield osmolyte amino acids, and metabolic precursors which can be converted into osmolyte amino acids by a metabolic step such as transamination. For example, a preferred precursor of the amino acid glutamine is poly-L-glutamine, and a preferred precursor of glutamate is poly-L-glutamic acid.

Also intended within the scope of this invention are chemically modified osmolytes or osmolyte precursors. Such chemical modifications involve linking to the osmolyte (or precursor) an additional chemical group which facilitates transport across the blood brain barrier or gastrointestinal tract, or inhibits degradation of the osmolyte molecule. Such chemical modifications have been utilized with drugs or prodrugs and are known in the art. (See, for example U.S. Pat. Nos. 4,479,932 and 4,540,564; Shek, E. et al., J. Med. Chem. 19:113-117 (1976); Bodor, N. et al., J. Pharm. Sci. 67:1045-1050 (1978); Bodor, N. et al., J. Med. Chem. 26:313-318 (1983); Bodor, N. et al., J. Pharm. Sci. 75:29-35 (1986);

Osmolytes can be used in a number of disease states which involve an osmotic disturbance. The term "osmotic disturbance" as used herein refers to a condition wherein plasma osmolality is outside the range of about 280-290 mosm/kg H$_2$O, or wherein plasma osmolality is not outside this range, but the plasma sodium concentration is outside the range of about 135-145 mEq/liter. In the case of an osmotic disturbance as used herein, osmotic constituents of the extracellular fluids cause swelling or shrinkage of cells.

Disease states which involve osmotic disturbances include, but are not limited to, acute hyponatremia, chronic hyponatremia, central pontine myelinolysis associated with hyponatremia, diabetic ketoacidosis, acute hypernatremia, hyperglycemic hyperosmolar coma, chronic hypernatremia, such as that associated with accidental salt loading in high sodium dialysis or feeding with high sodium baby formula. Osmotic disturbances are also associated with alcoholism (wherein alcoholic individuals are at risk for demyelination), diabetes mellitus, diabetes insipidus, and Acquired Immunodeficiency Syndrome (AIDS).

The invention is also directed to uremia, such as chronic uremia, wherein intracellular osmolytes may be depleted. Restoration of intracellular osmolytes to desired levels is achieved through the administration of an osmolyte (or osmolyte precursor) of this invention, either enterally or parenterally. In a preferred embodiment, a patient with chronic uremia undergoing dialysis is provided with an effective concentration of the osmolyte or osmolyte precursor in the dialysis fluid.

Osmotic disturbances included within the scope of this invention also include those substantially associated with particular medical or surgical treatments. Acute hyperosmolar conditions occur with the use of dehydrating agents, such as, for example, mannitol (in association with neurosurgery) or glycerol (as a treatment for cerebral edema). Hyponatremia can also occur with the use of hypoosmolar glycine solution to flush the bladder, as in transurethral prostate surgery. Dialysis disequilibrium syndrome occurs when uremic patients are dialyzed too rapidly leading to a rapid decrease in plasma urea, and resultant brain swelling.

Also intended within the scope of the invention is acute hyponatremia which occurs in association with physical activity or exercise which is accompanied by loss of fluids and salts through, for example, perspiration. Therefore, in one embodiment of this invention, a fluid supplemented with an osmolyte or osmolyte precursor of this invention is administered enterally to a subject prior to, or during the course of, the physical activity or exercise, e.g., as in a marathon race. Such "osmo-loading" protects cells, especially in the brain, from damage due to transient acute hypernatremia, and is intended to reduce fatigue and other symptoms known to be associated with prolonged physical activity or exercise.

The term "substantially associated with," as applied to the osmotic disturbances or symptoms for which the methods of the invention are effective, means those disturbances wherein the metabolic or osmotic demand for regulation of serum sodium or of intra- or extracellular osmolytes occurs during or after the event or disease precipitating the osmotic disturbance and is related thereto.

By the term "treating" is intended preventing, ameliorating, or curing a symptom or set of symptoms constituting, or substantially associated with, an osmotic disturbance.

The term "enteral" is intended to indicate a method of administration of osmolytes to that portion of the alimentary canal from the stomach to the anus.

The term "parenteral" denotes method of administration of osmolytes to that region outside of the digestive tract.

Examples of parenteral routes of administration include, but are not limited to, subcutaneous (SC), intramuscular (IM), intravenous (IV) or intraperitoneal (IP) injection or infusion, and nasopharyngeal, mucosal or transdermal absorption. In most cases, the osmolyte or precursor is administered IV. In IV administration, the therapeutically effective amount of the osmolyte or osmolytes, in liquid form, is directly administered from a reservoir from which tubing connects to a needle which is placed into a large vein of the recipient.

These IV fluids are sterile solutions composed of simple chemicals such as, for example, sugars, amino acids, and electrolytes, which can be easily assimilated.

Regardless of which route of administration is utilized, the osmolyte can be administered either singly or as a supplement. When used as a supplement to known solutions, the osmolyte can be mixed with an existing enteral or parenteral solution (or diet) prior to administration to the recipient. It is also possible to administer the osmolyte without mixing it directly with the other components of a diet as, for example, in IV infusion wherein the osmolyte is not directly added to the main IV bottle, but instead is added to a common reservoir using a "piggy-back" bottle.

This invention is also directed to osmolyte supplementation of formulas used in "total parenteral nutrition" (TPN) wherein patients derive their entire dietary requirements from the formula administered IV. TPN formulas do not normally contain the organic osmolytes of this invention or contain them or their precursors in concentrations too low for them to be effective in osmoregulation as is intended in this invention. Amino acids, some of which can also function as osmolytes, are added present in current TPN formulas for their nutritional value. There was no recognition in the art prior to the present inventors' discovery that such compounds in parenteral solutions could serve an osmoregulatory function. For this reason, the concentrations of glutamine, glycine or myo-inositol present in current parenteral formulas is too low for these compounds to exert an osmoprotective role via their action as organic osmolytes.

The therapeutically effective dose ranges for the administration of osmolytes are those large enough to prevent clinically significant brain shrinkage or swelling capable of altering neurologic function (by criteria which are well known in the art) or increasing the risk of hemorrhage or structural damage. For example, the dose should be capable of preventing demyelination.

It will be readily apparent to one of skill that the dosage of osmolyte or osmolyte precursor administered will be dependent upon the age, health, and weight of the recipient, the nature of any concurrent treatment, the frequency of treatment, and the nature of the effect desired.

The rate of administration for an osmolyte when administered IV is greater than or equal to about 1 $\mu$mole/kg body weight/day. Such administration rates could be 1 $\mu$mole/kg/day to 3 moles/kg/day preferably 2 $\mu$moles/kg/day to 240 mmoles/kg/day, and more preferably 200 $\mu$moles/kg/day to 120 mmoles/kg/day.

For enteral administration, the osmolyte is administered at a rate greater than or equal to about 5 $\mu$moles per kilogram of body weight per day. Such administration rates could be 25 $\mu$mole/kg/day to 15 mole/kg/day, preferably 10 $\mu$moles/kg/day to 1 mole/kg/day, and more preferably 1 mmole/kg/day to 600 mmole/kg/day.

According to the method of the invention, an osmolyte may be administered by simply modifying existing enteral or parenteral dietary formulas or infusion solutions to contain the proper concentration of the osmolyte. The $Na^+$ concentration in the osmolytetration supplemented fluid also comprises the invention, and is about 75–154 mEq/L, and the osmolarity of the fluid is about 150–300 mosm/L. In one embodiment directed to the treatment of acute hyponatremia as an emergency measure, such as during surgery, a high concentration of $Na^+$, such as about 513 mEq/L (osmolality of about 1 osm/L) is used.

In one embodiment, the osmolyte would remain in a dry form such as, for example, a sterile lyophilized powder which is aseptically hydrated at the time of administration and mixed at the proper concentration with the other components of the dietary composition.

Alternatively, the osmolyte could be premixed with the other components of a dry formula which is aseptically rehydrated at time of administration, or stored as a frozen concentrate which is thawed and mixed at the proper concentration at time of use.

The use of the osmolyte by the method according to the invention is ideally suited for the preparation of compositions. These compositions may comprise the osmolyte or combination of osmolytes, either alone or in combination with other chemicals. These other chemicals can be pharmaceutically acceptable carriers, as well as other active substances present in a dietary composition, such as, for example, free amino acids, protein hydrolysates, or oils.

Preparations for parenteral administration include sterile aqueous or non-aqueous solutions, suspensions, and emulsions. Carriers or occlusive dressings can be used to increase skin permeability and enhance cutaneous absorption.

Other pharmaceutically acceptable carriers comprise excipients and auxiliaries which facilitate processing of the active compounds into preparations which can be used pharmaceutically. Examples of excipients are water, saline, Ringer's solution, dextrose solution and Hank's balanced salt solution. The formulation may also contain minor amounts of additives such as substances that maintain isotonicity, physiological pH, and stability. Other formulations, known in the art, can be found in *Remington's Pharmaceutical Sciences* (latest edition), Mack Publishing Company, Easton, PA, which is hereby incorporated by reference.

Preparations which can be administered orally such as tablets, and capsules, and also preparations which can be administered rectally, such as suppositories, as well as suitable solutions for administration by injection or orally, contain from about 0.01 to 99 percent, preferably from about 20 to 75 percent of active compound(s), together with the excipient.

Other suitable excipients are, in particular, fillers such as saccharides and/or calcium phosphates, as well as binders such as starches, methyl cellulose, hydroxypropylmethylcellulose, sodium carboxymethylcellulose, and/or polyvinyl pyrrolidone. If desired, disintegrating agents may be added such as the above-mentioned starches, carboxymethyl-starch, cross-linked polyvinyl pyrrolidone, agar, alginic acid or a salt thereof, such as sodium alginate. Auxiliaries are, above all, flow-regulating agents and lubricants, for example, silica, talc, stearic acid or salts thereof, and/or polyethylene glycol. In order to produce coatings resistant to gastric juices, solutions of suitable cellulose preparations such as acetylcellulose phthalate or hydroxypropymethyl-cellulose phthalate are used. Dye stuffs or pigments may be added for identification or in order to characterize combinations of active compound doses.

Other pharmaceutical preparations which can be used orally include push-fit capsules made of gelatin, as well as soft, sealed capsules made of gelatin and a plasticizer. The push-fit capsules can contain the osmolyte in the form of granules which are mixed with fillers, and, optionally, stabilizers. In soft capsules, the active compounds are preferably dissolved or suspended in suitable liquids, such as fatty oils or liquid paraffin. In addition, stabilizers may be added.

Possible pharmaceutical preparations which can be used rectally include, for example, suppositories which consist of a combination of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the osmolytes in water-soluble form, for example, water-soluble salts. Aqueous injection suspensions may contain substances which increase the viscosity of the suspension, including, for example, sodium carboxymethyl cellulose. Optionally, the suspension may also contain stabilizers.

The invention also relates to a medicament or pharmaceutical composition comprising the components of the invention, the medicament being used for treating osmotic disturbances.

The preferred animal subject of the present invention is a mammal. By the term "mammal" is meant an individual belonging to the class Mammalia. The invention is particularly useful in the treatment of human subjects.

EXAMPLE I

Accumulation of Major Organic Osmolytes In Rat Renal Inner Medulla (IM) in Dehydration The purpose of this study was to evaluate the significance of organic osmolytes in the renal IM and cortex of normal and dehydrated rats. In addition to considering whether there are significant changes in the osmolytes during antidiuresis, we examined the stoichiometric interrelationships that exist between the various osmolytes. The results indicate that dehydration for 3 days is accompanied by a significant rise in the osmolyte content of the IM. However, the individual osmolytes increased to different extents from rat to rat, suggesting complex regulation.

A. METHODS

Wistar-Kyoto rats (Charles River, Wilmington, MA), weighing 110-300 g, were fed ad libitum (Purina rodent laboratory chow 5001). Rats were housed individually in metabolic cages for at least 1 wk before the experiment. Control animals were given free access to water, whereas dehydrated rats were deprived of water for 72 h. On the day of the experiment, the morning urine was collected under mineral oil for 2-4 h for a measurement of urine osmolality. Blood was collected into heparinized (300 U) 15-ml centrifuge tubes, centrifuged at 1,000 $\times$g, and the plasma was frozen for later analyses.

The kidneys were rapidly excised after sacrifice, and the inner medulla (25-50 mg/kidney) and superficial cortex ($\sim$600 mg/kidney) were dissected and minced in 1 and 3 ml, respectively, of ice cold 6% perchloric acid (PCA). The tissue from either 2 or 4 kidneys were pooled for each sample. After determining wet weight, the tissue was finely minced with scissors and homogenized by hand using a Dounce glass homogenized (Wheaton). The acid homogenate was kept ice-cold for -2 h and then centrifuged at 1,000 $\times$g for 10 min. The pellet was saved for analysis of protein, and the supernatant was neutralized (pH 7.0-7.4) with 2M KOH. The samples were centrifuged once more (1,000 $\times$g for 10 min to remove the $KClO_4$ precipitate, and the supernantant was frozen ($-40.C$). Each sample was run through an ion-exchange column (Chelex 100, Bio Rad) to remove paramagnetic ions such as $Cr^{2+}$ and $Mn^{2+}$ that would diminish resolution. The column was prepared by hydrating the resin in distilled water, packing 5 ml of slurry in a 10-ml syringe containing a glass-wool plug, and washing with 5 ml of water. The sample was loaded on the column, chased with 10 ml of water, and the eluant was titrated with HCl to pH 7.0-7.4. Each column was used for only three samples and then was either discarded or regenerated using 5 ml HCl (1N), 5 ml NaOH (1N), and 10 ml of water. The samples were subsequently frozen, lyophilized (Labconco Freeze Dryer 8) for 24-48 h, and reconstituted in 3 ml of $D_2O$. Each sample was then centrifuged (1,000 ×g for 10 min) and filtered through a 0.45-μm filter (Millipore) that was rinsed with an additional 0.5 ml of $D_2O$. The sample was lyophilized again and then frozen pending analysis.

To consider whether significant metabolite degradation occurred during dissection, extracts of minced whole kidneys were prepared as above and compared with extracts of whole kidneys that were rapidly frozen in liquid nitrogen. Each sample contained both kidneys from a single rat. The frozen kidneys were fragmented on a bed of dry ice using a hammer and a steel plate. The tissue fragments were then placed in ice-cold PCA (6%). These acid extracts were then centrifuged, neutralized, filtered, and lyophilized as described above.

NMR soectroscopy—Lyophilized samples were reconstituted in 3 ml of $D_2O$ containing 5 mM sodium 3-trimethylsilylpropionate-2,2,3,3-$d_4$ (TSP), a chemical shift and content standard, and placed in a 12 mm NMR tube (Wilmad, NJ). The $D_2O$ was used to attenuate the large portion signal from water and thereby allow better resolution and quantitation of the osmolyte peaks. NMR spectra were obtained using a Nicolet NT360 WB NMR spectrometer tuned to 360.09 MHz for protons. The $D_2O$ signal was used for shimming. Either 64 or 128 transients were collected into 4K or 8K data blocks using a 90° tip angle, a spectral width of ±3,000 Hz, and a 12 s delay time. Because all protons of interest had spin-lattice relaxation times (TI), of $\leq 2.2$ s, fully relaxed spectra were obtained. The free induction decay data were filtered for optimum resolution by apodization with a double exponential function, zero filled, and Fourier transformed. The integral of each peak was analyzed relative to the TSP peak to quantitate the amount of each metabolite in the sample.

In general, the predominant osmolytes were quantitated from the integral of a specific peak for each. GPC was quantitated by integrating the peak at 4.32 ppm. Because choline (3.20 and 4.07 ppm) was not significant in any sample, myo-inositol was quantitated by integrating the peak at 4.06 ppm. Betaine was quantitated by integrating the prominent trimethylamine peak at 3.27 ppm. However, to correct for a small contribution of myo-inositol to this signal (~15%), the myo-inositol measured at 4.06 ppm was subtracted from the integrated peak of 3.27 to yield the actual betaine content. When evident, sorbitol was most apparent from a peak at 3.85 ppm. To confirm the identity of the osmolyte species, solutions of known composition were prepared and peak assignments were made for each compound. Consequently, each osmolyte could be identified in a sample by observing peak positions, relative intensifies of companion peaks, or by spiking samples with known compounds. In addition, to assess whether osmolyte degradation, transformation, or dissipation occurred during the extraction and reconstitution procedures, solutions of known composition were analyzed before and after the extraction and reconstitution procedure. The results indicated that >95% of the osmolyte contents were recovered.

Biochemical assays and other measurements. IM urea content was measured fluorometrically in the PCA extracts according to Roman, R. J. et al., *Anal. Biochem.* 98:136-141 (1979)). The urease (US Biochemical, type III) was dissolved in a sodium phosphate buffer (0.2 M, pH 7.4) and dialyzed (Spectrapor, 3,500 MW cutoff) for 24 h in 1l of the same phosphate buffer. IM amino acids content was estimated spectrophotometrically by assaying NPS according to Lee, V. P. et al., *Anal. Biochem.* 14:71-77 (1966)). The assay was performed on the PCA extracts with glycine as standard. The NPS assay did not detect betaine, GPC, myo-inositol, or sorbitol. Very high concentrations of urea were detectable as NPS but the cross-reactivity (~0.1%) was not sufficient to significantly affect the results. In addition, the NPS assay is known to detect the 20 principal amino acids as well as a variety of other primary amines including ethanolamine, phosphorylethanolamine and taurine. IM sorbitol content was measured in the PCA extracts using sorbitol dehydrogenase and measuring the resultant production of NADH (Bergmeyer, H. U. et al., *Methods of Enzymatic Analysis.* Academic Press, New York, 1974, p. 1323-1330). This assay can detect other polyols such as xylitol; however, it does not detect myo-inositol, betaine, or GPC. Urine and plasma osmolality were determined by either freezing-point depression (Advanced Instruments, Needham, MA) or vapor pressure (Wescor 5100C, Logan, UT). Arginine vasopressin (AVP) levels were assayed in plasma extracts (Glick, S. M. et al., *Methods in Hormone Radioimmunoassay,* New York: Academic, 1979, p. 341-351) using a commercial polyclonal antibody (Arnel Pharmaceuticals) at a final dilution of 1:75,000, a cold vasopressin standard (Bachem), and 8-arginine $^{125}$I-labeled vasopressin (New England Nuclear) (Majzoub, J. A. et al., *Am. J. Physiol.* 252:E637-E642 (1987)).

Protein content of IM tissue was measured with the Lowry assay by first dissolving the PCA precipitate in 0.1 N NaOH-5% deoxycholate and using bovine serum albumin as the standard (Lowry, O.H. et al., *J. Biol. Chem.* 193:265-275 (1951)). Percent tissue water was determined in renal cortical tissue according to [(wet wt−dry wt)/wet wt]×100. Wet weight was measured using pretared glass vials and fresh tissue. Dry weight was measured after the tissue had been dried for at least 24 h in an oven at 100° C.

Materials. $D_2O$ (99.8%) was obtained from either Sigma or Aldrich. Betaine, GPC, myo-inositol, sorbitol, choline, chloride, sorbitol dehydrogenase, and NAD were obtained from Sigma.

Statistics. Each datum represents a pooled sample of either two or four kidneys. The data were calculated per wet weight and per protein content. Comparisons between control and dehydrated groups were made using the unpaired Student's t test. Values are expressed as means ±SE for n samples. Linear correlations were determined by least-squares regression analysis of individual data points.

B. RESULTS

Water deprivation for 3 days produced dramatic changes in body weight, urine, and plasma. The dehydrated animals lost 20.3±0.8% (n=25) of their body weight and experienced a 2.5-fold increase in urine osmolality from a control value of 1,503±68 (n=19) to 3,748±142 (n=18) mosmol/kg (p<0.001). Plasma osmolality rose from a control value of 289±2 (n=20) to 311±2 (n=25) mosmol/kg (p<0.001), and this was associated with a 10-fold rise in plasma AVP levels from 0.57±0.08 (n=16) to 6.7±0.9 (n=16) pg/ml plasma (p<0.001).

Figure 1:
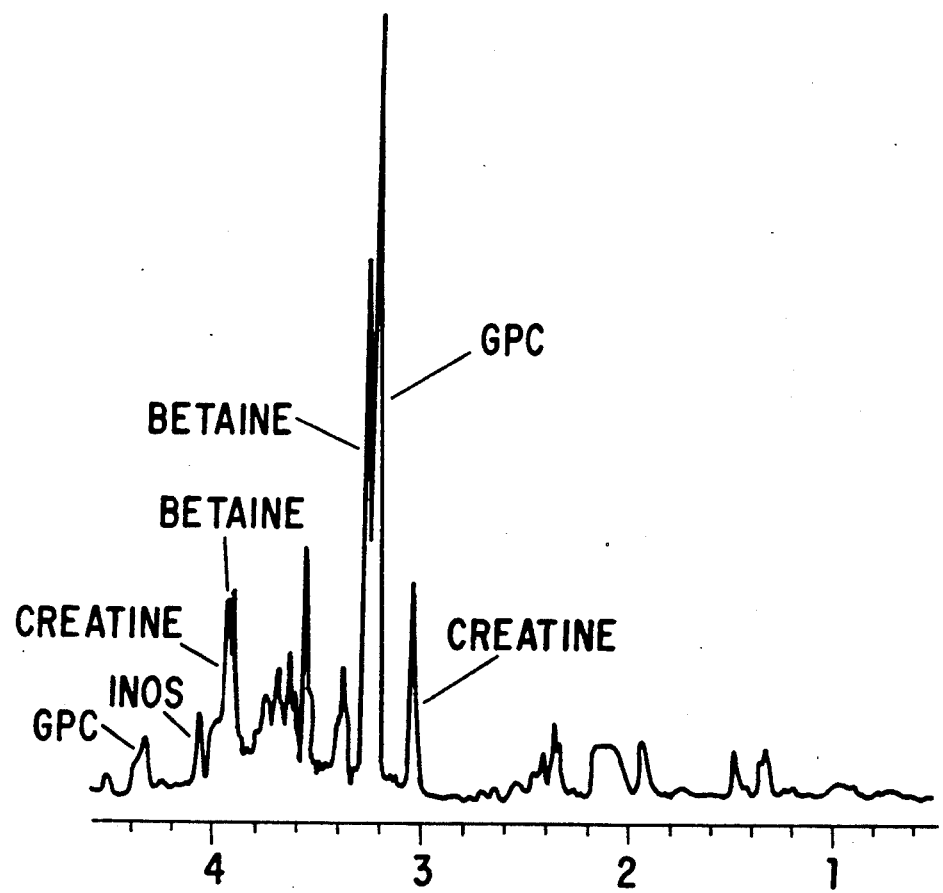
FIG. 1. $^1$H-NMR spectrum of a whole rat kidney. Two kidneys were frozen in liquid nitrogen and then subjected to a perchloric acid extraction procedure. Spectrum is sum of 64 transients and is referenced to sodium 3-trimethylsilylproprionate-2,2,3,3d$_4$ (TSP). Only osmolytes and creatine are labeled. Other peaks represent numerous organic compounds present in kidney. GPC, glycerophosphorylcholine; inos, myo-inositol.

Whole kidney - FIG. 1 is a typical $^1$H-NMR spectrum of a whole kidney extract from a control rat. The most prominent peaks have been identified as GPC, betaine, and creatine, Although many peaks are evident, only the characteristic osmolyte peaks have been labeled. When extracts of rapidly frozen kidneys (n=4) were compared with nonfrozen kidneys (n=4) the spectra were identical. Furthermore, quantitation of several peaks (in μmol/g wet wt) showed that there was no significant difference between these preparation methods in the amounts of betaine (2.8±0.6 vs. 3.1±0.5), GPC (6.4±0.4 vs. 6.3±0.6), creatine (1.4±0.1 vs. 1.4±0.1), or myo-inositol (3.3±0.3 vs. 3.2±0.3). Therefore the time required to dissect the IM and the cortex did not appear to alter significantly the osmolyte composition of the extracts.

Figure 2A:
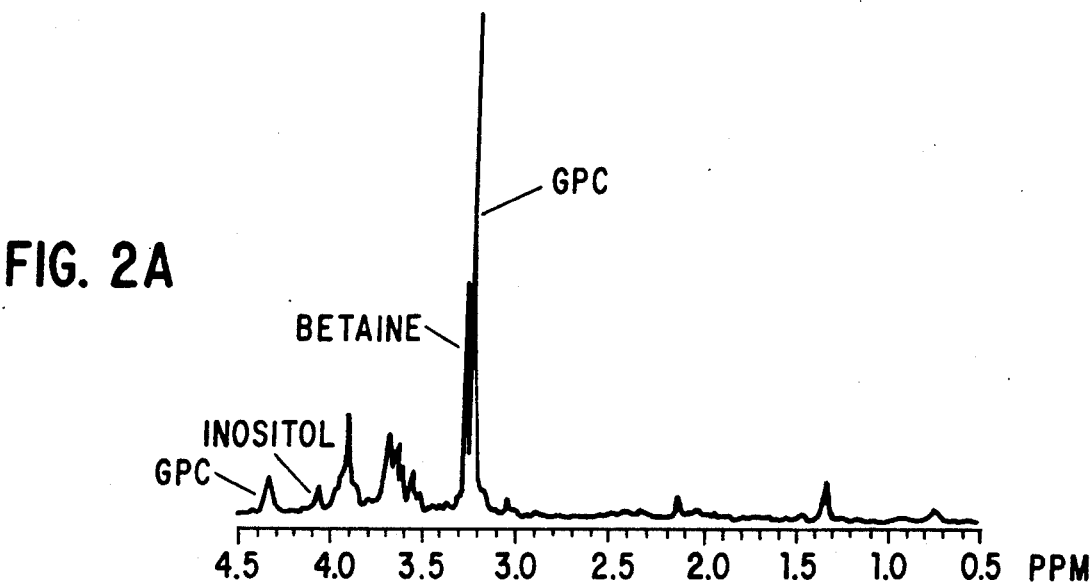
FIGS. 2A, 2B & 2C
Figure 2B:
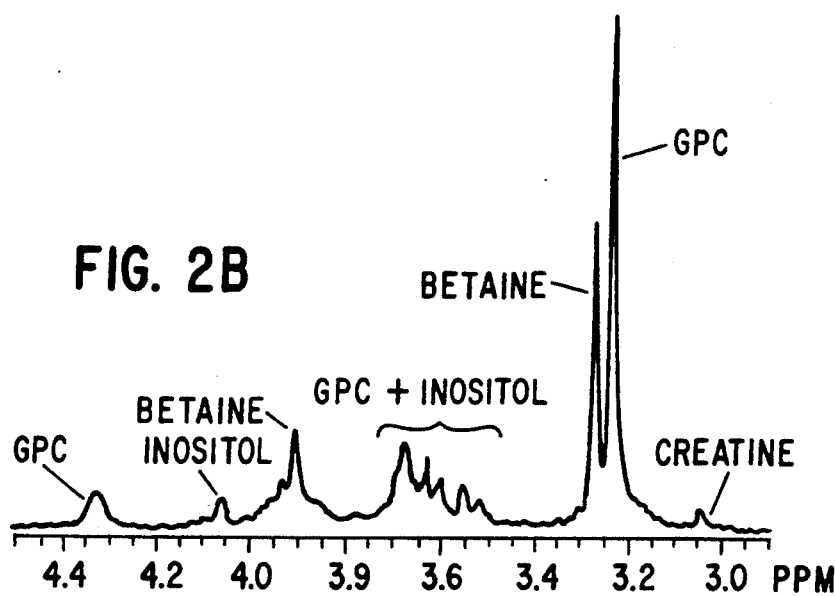

Inner medulla—FIG. 2A is a typical NMR spectrum of a renal IM that shows characteristic osmolyte peaks was well as several smaller peaks to the right (upfield) of the osmolytes. The smaller peaks in the range 2.0–2.5 ppm represent primarily amino acids. In addition, lactate (1.3 ppm) and creatine (3.04 ppm) are evident but they were present in smaller quantities than the trimethylamines and polyols. To focus on the principal osmolytes of the IM, FIG. 2B shows an expanded view of FIG. 2A from 2.9 to 4.4 ppm. The two most prominent peaks (~3.2 ppm) represent trimethylamine peaks of betaine (3.27 ppm) and GPC (3.22 ppm). Companion methyl and methylene protons of betaine (3.90 ppm) and GPC (4.32, 3.91, 3.67, and 3.63 ppm) are also evident. A unique myo-inositol peak is visible at 4.06 ppm with several other myo-inositol peaks also apparent (3.61 and 3.65 ppm). Although sorbitol was evident in some samples, there is none clearly apparent in this spectrum (e.g., 3.85 ppm). Because NH3 protons can freely exchange with the deuterium in $D_2O$ there is no signal from urea, although it was present in the sample.

Figure 2C:
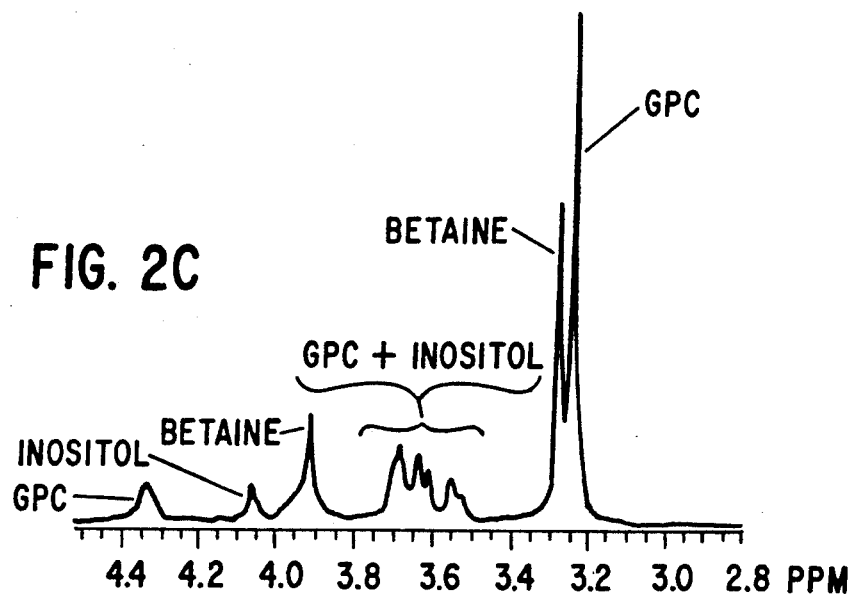

To evaluate whether we had indeed accounted for the major proton-containing solutes that exist in the IM, we prepared a solution containing only GPC (27 μmol), betaine (16 μmol), myo-inositol (14 μmol, and TSP (15 μmol) in $D_2O$. As shown in FIG. 2C, a spectrum of this known solution looks virtually identical to the IM spectrum (FIG. 2B). This apparent identity, coupled with previous gas chromatography measurements of renal IM (Bagnasco, S. et al., supra) suggests that these compounds are the major organic osmolytes of the rat renal IM.

Quantitation of the IM organic osmolytes in the NMR spectrum indicated that there was a general increase in solute content in dehydrated rats. Because dehydration is associated with a 20% loss of body weight, these organic solutes were quantitated per protein content to assess content changes. IM urea content increased from 2,036±230 (n=9) to 4,405±501 (n=13) nmol/mg protein (p<0.001) with dehydration. In addition, as shown in FIG. 3A, dehydration significantly increased GPC (in nmol/mg protein) from 265±32 (n=9) to 517±34 (n=13) (p<0.001 and betaine from 110±15 (n=9) to 214±40 (n=13) (p<0.05), whereas myo-inositol was not significantly elevated [103±16 (n=9) to 178±32 (n=13) (p<0.10)]. When normalized per gram wet weight (FIG. 3B), GPC increased by 137% from 17.1 ±2.2 (n=12) to 40.5±2.8 (n=16) μmol/g (p<0.001), and myo-inositol significantly increased by 87% from 6.8±1.0 (n=12) to 40.5±2.8 (n=16) μmol/g (p<0.02) but betaine was not significantly changed from 8.1±1.4 (n=9) to 14.0±2.4 (n=16) μmol/g. IM urea also increased significantly from 123 17 (n=12) to 363 35 (n=16) μmol/g (p<0.001). These data indicate that a net increase in the IM contents (i.e., per protein) of betaine and GPC occurred during hydration, whereas the apparent concentrations (i.e., per wet wt) of GPC and myoinositol increased with dehydration.

Several reports indicate that significant levels of sorbitol exists in the rabbit and rat IM (Bagnasco, S. et al., supra: Corder, C. N. et al., supra). However, NMR analysis of our samples generally detected little or no sorbitol. Because NMR analysis was unable to quantitatively resolve sorbitol levels of ≦0.5 μmoles, a spectrophotometric assay was used that confirmed that each IM contained between 0.1 and 0.7 μmoles of sorbitol. In fact, the spectrophotometric measurements correlated with out NMR analysis; sorbitol was evident only in spectra of samples that contained the higher quantities. Dehydration caused a 105% increased in IM sorbitol (FIG. 3A) from a control value of 64±9 (n=9) to 119 t 18 (n=13) nmol/mg protein (p<0.05). On a tissue weight basis (FIG. 3B), sorbitol content increased by 131% from 4.2±0.5 (n=12) to 9.7±1.3 (n=16) (p<0.002).

Analysis of NPS indicated that the renal IM contained significant levels of amino acids; however, IM NPS did not significantly change during dehydration (FIG. 3A and 3B). The control rats contained 344±44 (n=9) nmol/mg protein or 22.0±4.6 (n=12) μmol/g wet wt, and the dehydrated animals contained 337±54 (n=13) nmol/mg protein or 23.2±2.2 (n=16) μmol/g wet wt.

FIG. 4 provides a comparison of the total nonurea organic osmolyte pools in the IM of control and dehydrated rats. The data show that there was a 54% elevation of total osmolytes in dehydration from 885±77 (n=9) to 1,365±127 (n=13) nmol/mg (p<0.01). If one evaluates only the non-NPS osmolytes, however, there was a 90% increase from 541±52 to 1,027±92 nmol/mg protein (p<0.0001). Based on wet weight, the total osmolytes increased significantly from 58.5±8.5 (n=12) to 100.1±7.0 (n=16) μmol/g (p<0.002) and non-NPS osmolytes increased by 113% from 36.1±4.4 (n=12) to 76.9±6.0 (n=16) μmol/g (p<0.001). FIG. 4 also compares relative osmolyte contents. Although NPS did not change, it represented a substantial fraction of the total osmolyte pool in both the control (39%) and dehydrated (25%) states. Furthermore, in both groups the trimethylamines were more abundant than the polyols, and these two classes of compounds were increased in dehydration. Total trimethylamines (GPC+betaine) significantly increased in dehydration from 375±34 (n=9) to 731±64 (n=13) nmol/mg protein (p<0.001) or, per weight, from 25.1±3.2 (n=12) to 54.5 4.1 (n=16) μmol/g (p<0.001). Total polyols (inositol+sorbitol) increased in dehydration from 167±18 (n=9) to 297±33 (n=13) nmol/mg protein (p<0.01, or per wet weight, from 11.0 N 1.2 (n=12) to 22.4 (n=16) μmol/g (p<0.001).

Renal cortex - To address whether the increase in osmolytes was localized to the renal IM, we evaluated the osmolyte content of the renal cortex. FIG. 5 is a typical spectrum of a cortex, which is strikingly more complex than the IM spectrum. Similar to the IM however, there are two strong trimethylamine peaks that represent betaine and GPC. In addition, myo-inositol (e.g., 4.06 ppm) is also visible. In comparison to the IM, the osmolyte contents of the cortex were relatively low. In control rats, cortical betaine and GPC averaged 2.1±0.4 (n=8) and 2.7±0.2 (n=8) μmol/g wet wt, respectively, and dehydration did not significantly alter betaine [2.0±0.2 (n=9)] or GPC [3.3 0.3 (n=9)]. Furthermore, because cortical tissue water in control [79.6±0.8% (n=5)]and dehydrated [78.7± 0.4% (n=7)] rats was no different, these data indicate that betaine and GPC content clearly did not increase in dehydration. In contrast, dehydration was associated with a significant rise in myo-inositol from 1.2±0.2 (n=8) to 2.1±0.2 (n=9) μmol/g wet wt ($p<0.002$). Urea, sorbitol, and NPS were not measured in the cortex.

C. DISCUSSION

The role of organic osmolytes in the mammalian kidney has been poorly understood. Using NMR spectroscopy and biochemical assays, we confirmed the presence of high levels of trimethylamines (GPC and betaine), polyols (inositol and sorbitol), and amino acids (NPS) in the rat renal IM. To investigate the role of these osmolytes in antidiuresis, their quantities were assayed in the IM and cortex of kidneys from control and dehydrated animals. Three days of dehydration caused a 10-fold increase in plasma AVP and approximately doubled urine osmolality and IM urea content. Concurrently, the IM experienced a 54% increase in nonurea organic osmolyte content and a 90% increase in the nonurea, non-NPS (i.e., trimethylamines and polyols) osmolyte contents. The individual pools of total trimethylamine and total polyols increased by 95 and 78%, respectively, in dehydration. When individual osmolytes were quantitated per tissue protein content, dehydration caused significant increases in GPC (106%), betaine (95%), and sorbitol (130%) but not myo-inositol (73%) or NPS (−2%). When evaluated per tissue weight, dehydration significantly elevated all the osmolytes except betaine and NPS. Overall, the magnitude of the trimethylamine and polyol changes were comparable to the changes in urine osmolality and IM urea; all were increased about two-fold. Therefore these osmolytes were accumulated in antidiuresis as one would predict if they serve an osmoprotective function in the adaptation of the IM to a hypertonic environment.

IM osmolyte contents reported in this study are consistent with those observed by other investigators. In the present study, GPC was 553 nmol/mg protein or 40.5 μmol/g wet wt with 3 days of dehydration. Wirthensohn and co-workers (Wirthensohn, G. et al., *Pfluegers Arch.* 409:411-415 (987)) used a biochemical assay and measured rat IM GPC levels of 451.8 nmol/mg protein or 33.4 μmol/g wet wt in rats deprived of water for 16 h. Compared with our control GPC level of 17 μmol/g wet wt in rabbit IM, whereas Ullrich (supra) measured 125 μmol/g wet wt of GPC in the dog IM. In rat IM, sorbitol was measured as 0.34 (Corder, C. N. et al., supra) compared with 4.2 μmol/g wet wt in the present study, whereas rabbit contained 10 μmol/g wet wt (Bagnasco, S. et al., supra). Myo-inositol was detected at comparable levels in rabbit (10 μmol/g wet wt) ((Bagnasco, S. et al., supra) and dog (15 μmol/g wet wt (Cohen, M. A. H. et al., supra) as that observed by us in rat (6.8 μmol/g wet wt). At least 25 amino acids have been identified in the renal IM, and the total amino acid content ranges from 25 to 39 μmol/g wet wt in several species, including rat (Law, R. O. et al., supra); Robinson, R. R. et al., supra). Our NPS levels were comparable (22 μmol/g wet wt) with no particular amino acid appearing dominant in the NMR spectrum. Because we did not quantitate specific amino acids, it is conceivable that there were selected changes in the relative abundance of particular amino acids but this was not expressed as a significant increment in the total pool content.

Yancey and co-workers (Somero, G. N., supra); Yancey, P. H. et al., supra) showed that trimethylamines counteract the toxic effects of urea on numerous enzymatic processes. They established that a 2:1 concentration ratio of urea to trimethylamines was the optimal stoichiometric relationship for maintaining normal activity of many cellular enzymes. Therefore we calculated the urea-to-trimethylamine ratio in the IM. Under control conditions the ratio was 5.0±0.4 (n=13), and it was significantly elevated to 6.8±0.6 (n=16) ($p<0.05$) in the dehydrated animals. Urea, however, is presumed to be equally distributed throughout the intracellular and extracellular compartments of the IM, whereas GPC (Wirthensohn, G. et al., supra) and the other osmolytes are thought to be localized intracellularly. Assuming that the intracellular volume is 40% of the total tissue volume (Pfaller, W., In: *Advances in Anatomy. Embryology, and Cell Biology.* Hild, W. et al., Eds. Springer-Verlag, Berlin, vol. 70, chap. 5, p. 21), then these urea-to-trimethylamine ratios would reflect intracellular ratios of 2.0 and 2.7, values in the range of 2.0 described by Yancey and coworkers. The reason for the increase in the ratio with dehydration is unknown but could reflect a real change or a change in the relative volumes of the intracellular and extracellular compartments.

Renal cortex is known to contain both GPC-hydrolyzing enzyme activity (Wirthensohn, G. et al., supra) as well as choline dehydrogenase for conversion of choline to betaine (Wirthensohn, G. et. al., In: *Biochemistry of Kidney Function.* F. Morel, ed., Elsevier, New York, 1981). Our data show that the renal cortex also contained significant quantities of betaine, GPC, and myo-inositol (FIG. 5); however, only myo-inositol was significantly elevated by dehydration.

NMR spectroscopy proved to be a highly sensitive method for detecting several classes of organic osmolytes (>0.5 μmol). In addition, traditional biochemical assays were used to reliably quantitate the levels of sorbitol, amino acids, and urea for the following reasons. Sorbitol was present in amounts not generally detected in our NMR spectra. Amino acids were evident in our NMR spectra; however, the quantities of individual amino acids could not be reliably quantitated using NMR so they were measured collectively as NPS. Urea was undetectable by $^1$H-NMR spectroscopy because its protons are exchanged completely with deuterium (i.e., $-NH_2$ converted to $-ND_2$). Several other small peaks were present in the NMR spectrum, including lactate and phosphocreatine/creatine. However, the quantity of these organic osmolytes, was considerably less than that of the triethylamines, polyols, and NPS and thus did not appear to constitute a significant osmolyte pool. In addition to developing procedures for quantitating the major organic osmolytes, we demonstrated that each of these compounds is stable during the tissue harvesting and extraction procedures (see METHODS). Although it is possible that alternative extraction and/or detection methods might uncover additional osmolytes, our results, together with the data reported by others, offer no evidence that the rat IM contains significant quantities of other organic solutes.

To assess whether the IM osmolytes were uniformly increased in response to dehydration, the individual osmolytes were compared in each sample. FIG. 6A is a plot of betaine vs. GPC showing that these parameters are not directly correlated. With dehydration there was a generalized increase in GPC, whereas betaine showed significant scatter with some rats exhibiting control levels of betaine despite elevated GPC. Similar results were observed when myo-inositol and sorbitol were compared with GPC. Because urine osmolality, plasma osmolality, plasma antidiuretic hormone, and IM urea content were always elevated to similar levels in the dehydrated animals, these data suggest that additional modulators must exist to account for the animal-to-animal variations observed in the responses of betaine, myoinositol, and sorbitol. FIG. 6B provides some additional insight, indicating that there was a strong linear correlation ($r=0.87$) between betaine and myo-inositol in the IM. The regression line indicates that the IM accumulated 1.1 betaine per myo-inositol with an intercept not different from zero. The highest values were observed only in dehydrated individuals, although there was significant overlap between the control and dehydrated groups. This linear correlation suggests that these osmolytes are either regulated by the same effector(s) or that one of these osmolytes modulates the other. Finally, FIG. 6C is a composite comparing both betaine and myoinositol with sorbitol, indicating that here were no direct correlations. Interestingly, the control values are all tightly clustered, whereas the dehydrated samples tended to show an increase either in betaine and myo-inositol or in sorbitol but not concomitantly in all three. This mutually exclusive modulation of myo-inositol and betaine vs. sorbitol suggests multifactorial regulation of the osmolytes.

E. CONCLUSION

The rat renal IM contains high concentrations of trimethylamines and polyols that increase during antidiuresis (dehydration). The relative increases in total trimethylamines and total polyols were comparable to the changes in urine osmolality, suggesting that they were accumulated in response to the hypertonic environment.

EXAMPLE II

Amino Acids, Polyols, and Methylamines in Rat Brain: Response to Induced Hypernatremia

A. INTRODUCTION

Most studies have focused on the role of amino acids as a component of the idiogenic osmoles in brain. Specific amino acids shown to accumulate with hypernatremia in salt loading include glutamate, glutamine, aspartate, γ-aminobutyric acid (GABA), alanine, glycine, serine, ornithine, and taurine. However, the relative importance of any particular amino acid has varied somewhat in the different models of hypernatremia. In the brain there have been no studies of the methylamines. The polyols, myo-inositol and sorbitol, were shown to accumulate within 4 hours of hyperglycemia (Prockop, L. D., *Arch. Neurol* 25:126-140 (1971)), and work in hypernatremic rats showed an elevated myo-inositol concentration (Lohr et al., supra).

The purpose of the present study was to identify and quantify the organic solutes which accumulate in the brain in response to chronic salt loading or water deprivation, two different models known to cause hypernatremia. These two models were chosen because 5 days of salt loading is a well-known stimulus for accumulation of idiogenic osmoles in the brain, and 3 days of water deprivation is known to promote accumulation of methylamines and polyols in renal IM. Since previous studies have not attempted to identify all classes of organic compounds which could constitute idiogenic osmoles in a single model, we employed $^1$H NMR spectroscopy as an established technique for identification of multiple classes of organic compounds in brain and kidney. This approach was used successfully to identify organic osmolytes in the renal IM (see Example I). Our results indicated that three classes of compounds, amino acids, methylamines and polyols accumulate in the brain of salt loaded rats. Furthermore, the major compounds which accumulated were myo-inositol, glutamine, glutamate, phosphocreatine+creatine (PCr+Cr), glycerophosphorylcholine (GPC) and choline, in decreasing order of abundance. In contrast, no organic solutes were found to accumulate in water deprived rats.

B. METHODS

Animals Male Sprague-Dawley rats (250-350 g) were obtained from Charles River Breeding Co. and assigned to control ($n=8$), salt-loaded ($n=9$), and water-deprived ($n=4$) groups. All rats, housed individually in metabolic cages, were allowed free access to tap water and standard rodent chow (Purina Chow #5001) during one week of equilibration prior to the experimental regimens. The experimental periods were 4 days for control rats, 5 days for salt-loaded rats, and 3 days for water-deprived rats. During the experiment, all rats were allowed free access to food. In addition, control rats were allowed free access to tap water, salt-loaded rats were allowed free access to NaCl drinking water, and water-deprived rats had their water bottles removed. Chronic salt-loading was achieved by a combination of NaCl (320 mM) in the drinking water and daily gavage with 6 ml of 10% NaCl. This salt-loading protocol was found in our pilot studies to produce a sustained elevation of $P_{Na}$ (>155 meq/l). Body weights, water intake, and food intake were monitored daily. At the end of each protocol, rats were sacrificed by decapitation under light ether anesthesia.

Plasma sodium concentration was measured in plasma collected from the tail at the very beginning of each protocol and in plasma collected in trunk blood at the time of sacrifice. Sodium was measured in plasma by flame photometry (Instrumentation Laboratories Instruments).

Brain extracts: Following decapitation, each brain was rapidly removed from the cranium with a spatula and immediately freeze-clamped in liquid nitrogen. This entire procedure was performed in 5-10 seconds. The samples were pulverized in liquid nitrogen, and transferred to vials containing 3 ml of ice-cold 6% PCA. Each sample was left in the ice-cold PCA for 2 hours, centrifuged ($1000\times g$) for 10 minutes, and the supernatant was decanted and neutralized (pH 7.0-7.4) with 1.0 M KOH. The PCA precipitates were saved for analysis of protein content. The neutralized extracts were then passed through a 5 ml volume chelex column (Chelex 100-200, Bio-Rad) to remove paramagnetic ions which are known to diminish NMR signal resolution. The filtrates were frozen at −40° C. and subsequently lyophilized to dryness (48 hours). The lyophilisates were then reconstituted in 4 ml of D$_2$O (99.8%, Sigma Chemical Co.) and the residual potassium perchlorate precipitates were removed by centrifugation (1000×g for 10 minutes) and subsequent filtration using a 0.45 μm syringe (Millipore). The syringe and filter were rinsed with two 0.5 ml washes of D$_2$O. These extracts were frozen again, lyophilized (24 hrs), and then stored in the freezer (−40° C.) until they were analyzed. This extraction procedure preserves organic solutes in studies of the kidney (Example I).

$^1$H NMR Spectroscopy: The extracts were prepared as described in Example I. $^1$H NMR spectra were recorded as described in Example I. Individual organic components were identified in the spectra using three criteria: (i) comparison of peak positions and relative peak intensities to those observed following addition of known compounds to the samples (i.e., "doping"); (ii) comparison of the relative peak intensities of companion peaks associated with each compound; and (iii) observation of peaks at characteristic resonance frequencies as determined with pure compounds. Many of the peak assignments were also available from previously reported assignments in the brain and our assignments generally verified those assignments. In addition, the contents of organic compounds were comparable to previously published results in the literature. Once a compound was identified, one or two peaks which exhibited no significant overlap with other resonances in the spectrum were integrated to measure the content of that compound in the sample. Contents of organic compounds were verified by adding known quantities of a compound to a sample and observing the change in signal intensity and/or by comparison of the NMR measurement to a biochemical assay (e.g., myo-inositol and sorbitol). The individual peaks integrated to quantitate the methylamines, polyols, and amino acids are listed in Tables 1, 2, and 3. The lower limit of the NMR measurements was approximately 10 nmoles per sample or about 0.1 nmol/mg protein (each sample contained approximately 100 mg protein) as determined from quantification of the betaine peak at 3.27 ppm. Some other organic compounds which may have been more abundant than 0.1 nmol/mg (e.g., glycine) were not measurable in the spectra because they did not produce a high intensity peak such as that seen with the trimethylamines with 9 resonating protons of three adjacent methyl groups. This large peak of trimethylamines allows for lower contents of these compounds to be detected and quantitated compared to some more abundant compounds which lack the trimethyl moiety and the associated high intensity peak. As will be discussed below, some compounds were detected (e.g., taurine) in the spectra which could not be quantitated.

Biochemical Assays: myo-Inositol was measured spectrophotometrically by measuring the reduction of NAD$^+$ in the presence of myoinositol dehydrogenase as described previously (Weissbach, A., In: *Methods of Enzymatic Analysis* 3:1333–1336 (1974)). Sorbitol was measured spectrophotometrically as measuring the reduction of NAD$^+$ in the presence of sorbitol dehydrogenase. The protein content was measured as in Example I.

Chemicals: All chemicals were analytical grade and were obtained from standard commercial sources. D$_2$O (99.8%) was obtained from either Sigma or Aldrich Chemical Co. TSP was obtained from Aldrich. Methylamines, polyols, and amino acids used to prepare standards were obtained from Sigma Chemical Co. myo-Inositol dehydrogenase, sorbitol dehydrogenase, and NAD$^+$ were also purchased form Sigma Chemical Co.

Statistics: All values represent the mean±SEM for n animals in each group. Comparison of contents of individual compounds to those in the control group were made by one-way analysis of variance (ANOVA, STAT PAK) followed by the unpaired Student's t test when the F statistic was found to reach significance ($p<0.05$). The paired t test was used to determine significant differences on consecutive days for body weight, water intake, and food intake.

C. RESULTS

Animals: FIG. 7 indicates the daily water intake for each group of rats throughout the experiment. In the 24 hrs. preceding the start of the experimental regimens (Day 0), the three groups of rats drank comparable amounts of water, about 38 ml/day, and the control rats maintained this water intake level throughout the protocol. In contrast, salt-loaded rats rapidly increased their fluid intake and achieved a stable intake of 80 to 100 ml/day on days 2 to 5. On day 4 the water intake of salt-loaded rats (101±3 ml/day) was 146% higher, and on day 5 (103±2 ml/day) 151% higher than controls on day 4 ($p<0.001$). Fluid intake of water-deprived rats was maintained at 0 ml/day on days 1 through 3 of the protocol.

FIG. 8 indicates the daily food intake of the 3 groups of rats throughout their respective protocols. Prior to initiating the experimental regimens (Day 0), all 3 groups consumed approximately 26 gm of food per day. As seen with water intake, the food intake of the control group was relatively constant throughout the experiment. In contrast, both the salt-loaded and water-deprived groups of rats displayed significant and parallel decreases in their food intakes such that on day 2 and thereafter both groups consumed comparable amounts ranging from 5 to 10 g/day. On the final day of the respective protocols, the food intakes of the salt-loaded (4.7 g/day) and water-deprived (5.0 g/day) groups were significantly less than the control group (26 g/day) ($p<0.001$). Food intake of salt-loaded rats on day 4 (9.6 g) was also significantly less than controls on day 4 ($p<0.001$).

A plot of the cumulative percent changes in daily body weights for the three groups is shown in FIG. 9. Over the course of the experiment, the control group demonstrated a 6% gain in body weight ($p<0.05$). In contrast, both the salt-loaded and water-deprived groups exhibited significant and parallel decreases in body weight. The salt-loaded animals lost 22% of their body weight in 5 days ($p<0.001$). The water-deprived rats lost 18% of their body weight in 3 days ($p<0.001$).

Plasma On day 0, all three groups had similar $P_{Na}$ values with control rats at 143±1 meq/l, salt-loaded rats at 144±3 meq/l, and water-deprived rats at 140±2 meq/l. At the end of the study the control rats exhibited no significant change in $P_{Na}$ at 141±3 meq/l. In comparison, the $P_{Na}$ of both the salt-loaded (165±5 meq/l) and the water-deprived (151±2 meq/l) groups were significantly greater than the control group ($p<0.005$). In addition, the $P_{Na}$ of salt-loaded rats was significantly higher than that of water-deprived rats ($p<0.05$). Consequently, compared to the control group, three days of water deprivation produced a $P_{Na}$ 7% higher, and five days of hypertonic salt loading produced a $P_{Na}$ 17% higher.

Organic Compounds: A typical $^1H$ NMR spectrum of a brain extract from a salt-loaded rat is shown in FIG. 10. Only a portion of the entire spectrum is shown (from −1.5 ppm to −4.5 ppm) since this is where the methylamines, polyols, and amino acids are located. This spectrum is qualitatively similar to previously published spectra of brain and shows characteristic large resonances for total phosphocreatine and creatine (PCr+Cr) and N-acetyl aspartate (NAA), two compounds known to be relatively abundant in brain. Also evident in this spectrum are regions which contain peaks representing methylamines including GPC, amino acids, and myo-inositol resonances.

Amino acids: Characteristic proton resonances for NNA, glutamine, glutamate, GABA, aspartate, alanine, glycine, taurine, and serine were identified in the extracts; however, the relative contributions of individual amino acids to the total pool of amino acids differed markedly. The most abundant amino acids were identified in the region of 2.0 to 2.8 ppm, and these included NAA, glutamate, glutamine, and GABA. FIG. 11 compares scaled spectra of the "amino acid region" of $^1H$ NMR spectra (i.e., 2.2 to 2.8 ppm) obtained from a control (dashed line) and a salt-loaded (solid line) rat. These spectra contain characteristic peaks for NAA (peaks 1-8), glutamine (peaks 9-11), glutamate (peaks 12-14) and GABA (peak 15). In addition, these spectra indicate that compared to control, the brain of the salt-loaded animal contained more glutamate and glutamine, but equivalent amounts of NAA and GABA.

Table 1 summarizes the brain contents of these four amino acids in the three groups of rats. Glutamate, the most abundant amino acid, was 27% higher in the salt-loaded animals (101 nmol/mg) than in the controls (79.6 nmol/mg). The water-deprived animals (68.1 nmol/mg) showed no significant change in glutamate content compared to controls. Glutamine content in salt-loaded rats (58.1 nmol/mg) was also significantly greater than in controls (35.3 nmol/mg), but was unchanged in water-deprived rats (35.9 nmol/mg). Unlike glutamate and glutamine, neither NAA nor GABA was significantly changed in salt-loaded or water-deprived groups compared to the control group.

TABLE 1

Brain Contents of Major Amino Acids in Control, Salt-Loaded, and Water-Deprived (−H₂O) Rats

| Amino Acid | Brain Contents (nmol/mg protein) | | |
|---|---|---|---|
| | Control | Salt-Loaded | −H₂O |
| Glutamate | 79.6 ± 6.1 | 101.0 ± 6.9[1] | 68.1 ± 4.3 |
| Glutamine | 35.3 ± 3.2 | 58.1 ± 4.7[2] | 35.9 ± 7.6 |
| NAA | 50.9 ± 3.7 | 60.0 ± 5.5 | 48.0 ± 2.4 |
| GABA | 13.5 ± 1.9 | 15.2 ± 2.2 | 16.8 ± 1.0 |
| Total Amino Acids | 180 ± 15 | 235 ± 13[1] | 167 ± 11 |

Contents of individual amino acids in perchloric acid extracts of brain were measured with $^1H$ NMR spectroscopy. Abbreviations: NAA for N-acetyl aspartate, and GABA for γ-aminobutyric acid. [1]$p < 0.02$, [2]$p < 0.002$.

Several other less abundant amino acids were identified in other portions of the spectrum including alanine (FIG. 10, e.g., 1.46/1.48 ppm), aspartate (FIG. 10, e.g., 2.78 ppm), glycine (FIG. 10, e.g., 3.35 ppm), taurine (FIG. 10, e.g., triplet at 3.41, 3.43 and 3.45 ppm), and serine (3.99 ppm). The contents of these amino acids appeared to be low when compared to other peaks in the spectrum and they frequently overlapped with neighboring peaks; therefore, they could not be quantified in many of the samples. The apparent low contents of these amino acids in all three groups of rats suggested they were unlikely to play a significant role in brain osmoregulation in this study. This analysis of the amino acids indicated, in agreement with previous observations, that glutamate, glutamine, NAA, and GABA are among the most abundant amino acids in the brain. Calculation of the total brain content of these four amino acids indicated that salt-loaded rats contained 31% more of these amino acids than control rats. However, this elevation reflected selective increases in glutamate and glutamine only.

Methylamines: The inset in FIG. 12 shows that PCr+Cr (peak 9) and GPC (peak 5) are the two most abundant methylamines in the brain. The expanded view of that portion of the NMR spectrum (3.14 ppm to 3.34 ppm) indicates several additional methylamines were present. For comparison, representative brain spectra from both a control (dashed line) and a salt-loaded (solid line) rat are shown; the spectra from water-deprived rats were comparable to the control rat spectrum. Identifiable in these spectra are betaine (peak 3), glycerophosphorylcholine or GPC (peak 5), phosphorylcholine or PCholine (peak 6), and choline (peak 7). The only form of betaine detected was glycine betaine (betaine). Although proline betaine has been found in human urine, this form of betaine has not been detected in our studies of rat brain and renal IM. Three methylamines, PCr+Cr, GPC and choline, were significantly elevated in salt-loaded rats compared to controls.

A quantitative comparison of the methylamine contents in the brain of experimental and control rats is given in Table 2. In all three groups, PCr+Cr and GPC were the most abundant methylamines, constituting approximately 72-84% of the total pool. In addition, the brain content of PCr+Cr in salt-loaded rats (26.1±1.4 nmol/mg) was 32% higher than in control rats (19.8±1.5 nmol/mg). GPC was also significantly higher in salt-loaded rats (13.1±1.0 nmol/mg) as compared to control rats (7.5±0.7 nmol/mg). Neither PCr+Cr nor GPC was significantly changed with 3 days of water deprivation. Though less abundant, choline was elevated 114% in the salt-loaded group (4.7 nmol/mg) Brain choline content of water-deprived rats (1.5±0.3 nmol/mg) was similar to controls (2.2 nmol/mg). PCholine content was 4 nmol/mg in controls, and was unchanged in the two experimental groups. Betaine was relatively scarce (2.4 nmol/mg in controls) and failed to accumulate in either salt-loaded or water-deprived rats. Total methylamines (i.e., PCr+Cr+PCholine+choline+betaine) in the salt-loaded animals (52.1±2.3 nmol/mg) were 45% higher than in control rats (36.0±3.3 nmol/mg protein). Total brain methylamine contents of the control and water-deprived rats were not significantly different. Therefore, in salt loading, there was a significant increase in the total methylamine content of the brain, and PCr+Cr, GPC and choline were largely responsible for this change. Three days of water deprivation produced no significant change in methylamine contents.

TABLE 2

Brain Contents of Major Methylamines in Control, Salt-Loaded, and Water-Deprived (−H₂O) Rats

| Methylamine | Brain Contents (nmol/mg protein) | | |
|---|---|---|---|
| | Control | Salt-Loaded | −H₂O |
| PCr + Cr | 19.7 ± 1.5 | 26.1 ± 1.4[1] | 18.6 ± 1.0 |

TABLE 2-continued

Brain Contents of Major Methylamines in Control, Salt-Loaded, and Water-Deprived ($-H_2O$) Rats

| Methylamine | Brain Contents (nmol/mg protein) | | |
|---|---|---|---|
| | Control | Salt-Loaded | $-H_2O$ |
| GPC | 7.5 ± 0.7 | 13.1 ± 1.0[3] | 8.0 ± 0.1 |
| Choline | 2.2 ± 0.3 | 4.7 ± 0.6[2] | 1.5 ± 0.3 |
| PCholine | 4.0 ± 1.0 | 5.0 ± 1.0 | 3.0 ± 1.0 |
| Betaine | 2.4 ± 0.5 | 3.4 ± 0.8 | 0.7 ± 0.2 |
| Total Methylamines | 36.0 ± 3.3 | 52.1 ± 2.3[1] | 31.7 ± 1.4 |

Contents of individual methylamines were measured with $^1H$ NMR spectroscopy. Abbreviations: PCr + Cr for phosphocreatine plus creatine. GPC for glycerophosphorylcholine, PCholine for phosphorylcholine. [1]$p < 0.005$, [2]$p < 0.002$, [3]$p < 0.001$.

Polyols: Two polyols, myo-inositol and sorbitol, are known to exist in the brain and are also known to accumulate in the renal IM. $^1H$ NMR spectra indicated the presence of significant quantities of myo-inositol but not sorbitol in the three groups of rats. FIG. 12 contains three peaks (1, 2 and 4) attributable to myo-inositol which appear larger in the salt-loaded rat compared to the control. Other proton resonances from myo-inositol were also clearly identified including seven peaks clustered in the region 3.5 to 3.7 ppm (FIG. 10) as well as a triplet at 4.06 ppm. Sorbitol was now visible in $^1H$ NMR spectra from any of the brain extracts (e.g., 3.85 ppm, 3.67 ppm, or 3.65 ppm).

In addition to $^1H$ NMR spectroscopy, biochemical assays were used to quantify myo-inositol and sorbitol contents and these assays confirmed the $^1H$ NMR analysis. The mean content of myo-inositol assayed in the brain extracts from the three groups was 101±4% of that measured by NMR spectroscopy. Furthermore, though present, brain sorbitol content (about 0.4 nmol/mg protein) was below the level detectable by NMR spectroscopy. The polyol contents of the three groups are listed in Table 3. Myo-inositol was greater than 100-fold more abundant than sorbitol in the brain of control animals (65.7 vs. 0.40 nmol/mg protein). Moreover, myo-inositol was 36% higher in salt-loaded rats (89.5 nmol/mg). Brain myo-inositol with 3 days of water deprivation (57.8 nmol/mg) was not significantly different from controls. In contrast to myo-inositol, sorbitol failed to change in either experimental group. Total polyols (i.e., myo-inositol+sorbitol) were significantly elevated in the salt-loaded rats (90.0±8.3 nmol/mg). Total polyols in the brain extracts of water-deprived rats (58.2t2.0) were similar to controls (66.1t5.1 nmol/mg).

TABLE 3

Brain Contents of Polyols in Control, Salt-Loaded, and Water-Deprived ($-H_2O$) Rats

| Polyol | Brain Contents (nmol/mg protein) | | |
|---|---|---|---|
| | Control | Salt-Loaded | $-H_2O$ |
| Myo-inositol | 65.7 ± 5.1 | 89.5 ± 8.3[1] | 57.8 ± 2.0 |
| Sorbitol | 0.40 ± 0.10 | 0.47 ± 0.07 | 0.39 ± 0.05 |
| Total Polyols | 66.1 ± 5.1 | 90.0 ± 8.3[3] | 58.2 ± 2.0 |

Contents of myo-inositol and sorbitol were measured in PCA extracts of brain with $^1H$ NMR spectroscopy (myo-inositol) or a biochemical assay (sorbitol). [1]$p < 0.02$, [2]$p < 0.05$.

Total amino acids, methylamines, and polyols: The sum of the brain contents of the major methylamines, polyols, and amino acids in the three groups of rats is shown in FIG. 13. The total of these solutes in the control rats averaged 282±22 nmol/mg whereas the salt-loaded rats contained 377±23 nmol/mg indicating that salt loading was associated with a net increase of 95 nmol/mg or 34% in the content of these solutes. Amino acids constituted the largest fraction (+58%) of this organic solute change exhibiting a net increase of 55 nmol/mg. The net change in polyols (24 nmol/mg) was 25% of the total change in these solutes and this was due entirely to an increase in myo-inositol. The increase in methylamines (16 nmol/mg) represented 17% of the total change. Three days of water deprivation did not produce an elevation in individual or total (257 nmol/mg) organic solutes.

D. DISCUSSION

In the present study, $^1H$ NMR spectroscopy and biochemical assays were used to identify and quantify the major organic solutes in brains of normal, salt-loaded, and water-deprived rats. Chronic salt loading (5 days) caused an increase in $P_{Na}$ and an increase in organic solute contents in brain. Three-day water-deprived rats had an elevated $P_{Na}$ compared to controls; however, the degree of hypernatremia was less than that in salt-loaded animals, and they failed to show a significant change in brain organic solutes. The organic solutes which accumulated in the brains of salt-loaded rats belonged to three chemical classes, amino acids, methylamines and polyols. In particular, myo-inositol, glutamine, glutamate, PCr+Cr and GPC were considerably higher in salt-loaded rats compared with controls. Interestingly, these three classes of solutes are known to be involved in cell volume regulation in numerous mammalian and nonmammalian systems, including the hypertonic renal IM (see Background).

Qualitatively, the brain $^1H$ NMR spectra were identical in all three groups of rats. The most prominent peaks visible in the $^1H$ NMR spectrum were identified as glutamate, myo-inositol, NAA, glutamine, PCr+Cr, GABA, and GPC, in decreasing order of content.

It is important to note that no new organic compounds were detected in extracts from either salt-loaded or water-deprived rats. Rather, adaptation to salt loading was associated with elevation in the amounts of individual amino acids, methylamines, and polyols which were also present in the brain of control and water-deprived animals.

The major amino acids in brain were elevated by 31% with salt loading (235 vs. 180 nmol/mg protein; Table 1) due to selective elevation of two amino acids, glutamine and glutamate. Brain glutamine content was 65% or 22.8 nmol/mg protein higher in saltloaded rats than in control rats. Glutamate, a stimulatory neurotransmitter, was elevated by 27%, or 21.4 nmol/mg protein. Brain NAA content, which is known to be very stable under various physiological and non-physiological conditions, was unchanged. Similarly, GABA, a known inhibitory neurotransmitter, was unchanged in the present study. Therefore, of the four major amino acids detected in brain, only glutamine and glutamate were significantly elevated with salt loading.

Other less abundant amino acids were also identified in the NMR spectra; however, these were not quantitated because they were generally present in unmeasurable quantities and/or had overlapping peaks. These amino acids included aspartate, alanine, glycine, serine, and taurine. With the exception of taurine, the contents of these amino acids are known to be low in the brain such that their combined contents account for only 11% of the total amino acids. Furthermore, these amino acids account for only 14% of the elevation in brain total amino acids with salt-loading. Although we were unable to measure the contribution of these amino acids to the osmolyte adaptation to hypernatremia, the apparent low quantities of these less abundant amino acids in both control and experimental rats suggests that, at most, they play only a minor osmoregulatory role.

Methylamines are known to play a prominent osmoregulatory role in marine vertebrates and invertebrates as well as bacteria. In the present study, brains of control, salt-loaded, and water-deprived rats all contained the same five methylamines: PCr+Cr, GPC, PCholine, betaine, and choline, in decreasing order of content. Total brain content of these methylamines was elevated by 16 nmol/mg protein, or 45% with salt loading. The methylamine accumulation with salt loading was very selective whereby PCr+Cr increased by 6.3 nmol/mg or 32%, GPC increased by 5.6 nmol/mg or 75%, and choline increased by 2.5 nmol/mg or 114%. In contrast, three-day water-deprived animals showed no change compared to controls. To our knowledge, changes in GPC have not previously been documented in the brain; however, GPC accumulates in the renal IM in water-deprived animals (see Example I), in cultured renal epithelial cells exposed to hyperosmolar medium (Nakamishi et al. (1988), supra), and in some tumors (Daly, P. F. et al., *FASEB J.* 2:2596–2604 (1988)). Betaine was unchanged in the brain in the two experimental groups, a finding which suggested it was not performing an osmoregulatory role. This was a notable difference from its described role as an osmolyte in the renal IM. The cellular basis for the 114% rise in choline is unknown but this may relate to its acting as a precursor for GPC inside the cell.

Total polyols (myo-inositol + sorbitol) were elevated by 36% in brain extracts of salt-loaded rats (90.0 vs. 66.1 nmol/mg protein in controls) related entirely to the accumulation of myo-inositol. There was no change in polyols noted in water-deprived rats. Myo-inositol was the second most abundant organic solute measured in the brain, was elevated 36% in salt-loaded rats, and accounted for 25% of the 95 nmol/mg protein increase in brain organic solutes observed with salt loading. In contrast, brain sorbitol content (0.4 nmol/mg protein) was less than 1% of the myo-inositol content and failed to respond to either salt loading or water deprivation. In a recent report, Lohr and coworkers (supra) observed similar polyol responses in brain extracts of salt-loaded, water-deprived animals: myo-inositol was elevated 53% and sorbitol was unchanged. Conversely, Prockop et al. (supra), studying hyperglycemia in the dog, found that both myoinositol and sorbitol were elevated in brain. These findings suggest brain is able to accumulate organic solutes in both salt-loading and hyperglycemia, but can utilize different solutes to achieve this endpoint. It is also notable that a previous study of polyols in the renal IM of water-deprived rats showed that when myo-inositol accumulated, sorbitol was unchanged. Therefore, polyols can behave as osmolytes in brain as well as in renal IM.

The failure of water-deprived rats to accumulate osmolytes was somewhat unexpected since previous studies of hyperosmolar states have suggested that hypernatremia is associated with formation of idiogenic osmoles in the brain. However, this hypothesis is based primarily, if not exclusively, on studies of salt-loaded animals. Formation of idiogenic osmoles in brain of animals submitted solely to water deprivation (without salt loading) has not, to our knowledge, been reported. Based on findings in the present study, it seems unlikely that changes in food intake or body weight were important since saltloaded rats exhibited similar changes. Furthermore, although the shorter period of hypernatremia (i.e., 3 days) may have been important, 3 days is sufficient for detectable, if not maximal, accumulation of brain idiogenic osmoles with salt loading, and for accumulation of osmolytes in the renal IM of water-deprived rats. The degree of hypernatremia could have been an important determinant of osmolyte accumulation since the $P_{Na}$ was significantly higher in salt-loaded rats (165 meq/l) than in water-deprived rats (151 meq/l). In conclusion, using $^1H$ NMR spectroscopy, a number of specific amino acids, methylamines, and polyols were shown to exist and accumulate in brain extracts of salt-loaded rats. No accumulation of organic solutes was observed in a 3-day water deprivation protocol. The major brain organic osmolytes which accumulated in salt loading were glutamine, myo-inositol, glutamate, PCr+Cr, and GPC. Furthermore, the previously recognized role of amino acids, methylamines, and polyols in osmoregulation of other organs and other species suggests that these organic solutes accumulate to protect brain cells from the deleterious effects of cellular dehydration and/or accumulation of inorganic ions.

EXAMPLE III

Methylamines and Polyols in Kidney, Urinary Bladder, Urine, Liver, Brain, and Plasma The purpose of the present study was to use $^1H$ nuclear magnetic resonance (NMR) spectroscopy to identify specific methylamines and polyols in several tissues of normal rats.

A. MATERIALS AND METHODS

Male Sprague-Dawley rats were used, as describe in Example 11. Perchloric acid extracts of renal IM, urinary bladder, liver, and brain were prepared as described in Examples I and II. Urine and plasma were prepared as described in Example IV, and extracted essentially as described in Examples I and II. NMR spectroscopy was performed as described in Examples I and II.

B. RESULTS

FIG. 14 is a typical $^1H$ NMR spectrum of normal rat renal IM which shows characteristic osmolyte peaks including methylamines, polyols, and lactate. In particular, methyl protons of both GPC and betaine are evident at 3.23 and 3.27 ppm, respectively. A companion GPC resonance is evident at 4.32 ppm whereas a companion betaine resonance is apparent at 3.91 ppm. Peaks characteristic of myoinositol (4.06, 3.61, and 3.65 ppm) and sorbitol (3.85 ppm) can be detected. Upfield from the methylamines and polyols are a variety of smaller peaks including resonances characteristic of lactate. Since $NH_3$ protons can freely exchange with the deuterium in $D_2$, there is no signal from urea.

FIG. 15a is a typical $^1H$ NMR spectrum of a urinary bladder and FIG. 15b provides an expanded view of the region from 2.9 to 3.4 ppm which is known to contain methylamines. These spectra show distinct differences in methylamine content of the bladder and the IM. Unlike the IM, the bladder has multiple resonances in the region of 3.0 ppm, most of which were unidentified. This spectrum also indicates that neither GPC (3.23 ppm) nor betaine (3.27 ppm) was the most prominent compound in this region of the spectrum. Characteristic resonances for myo-inositol, but not sorbitol, were also detected in the spectra.

A typical $^1$H NMR spectrum of rat urine (FIG. 16) indicates the presence of several methylamines including betaine, GPC and choline. Neither myo-inositol nor sorbitol was apparent but other unidentified organic solutes were detected.

A typical $^1$H NMR spectrum of liver is shown in FIG. 17. Numerous organic solutes were present in this extract; however, due to extensive overlapping of peaks in the 3.3–4.5 ppm region, it was not possible to identify most of the compounds. Characteristic GPC and betaine methylamine peaks were discernible at 3.23 and 3.27 ppm.

A typical $^1$H NMR spectrum of a brain extract is shown in FIG. 18. The largest peaks represent phosphocreatine and creatine (PCr+Cr) and N-acetyl aspartate (NAA). The major classes of compounds which are apparent in this spectrum included amino acids, methylamines, and polyols. Major amino acids which were detected included glutamine, glutamate, γ-aminobutyric acid (GABA), and NAA. Other amino acids which were present but were relatively less abundant included taurine (TAU), alanine, and serine. Methylamines included GPC and betaine; polyols included myo-inositol.

FIG. 19 is a typical $^1$H NMR spectrum of a PCA extract of plasma which shows only the methylamine region (2.9–3.3 ppm). Several methylamines including betaine, GPC, choline, and PCr+Cr were detected. Neither myo-inositol nor sorbitol was detected.

C. DISCUSSION

The present investigation confirmed the presence of significant glutamine and glutamate in the brain of normal animals. In addition, we observed a variety of methylamines including GPC, betaine, phosphorylcholine, and choline. Several strong resonances representing myo-inositol were also observed in the brain spectra suggesting a role for this polyol in osmoregulation in the brain.

Analysis of plasma showed that several methylamines, including GPC, choline and PCr+Cr, circulate in the blood and offer a potential source of osmolytes for delivery to any organ in the body.

In conclusion, this investigation showed that solutes which are known to act as organic osmolytes in the renal IM, including methylamines, polyols and amino acids, are also present in a variety of extra-renal locations.

EXAMPLE IV

Methylamine and Polyol Responses to Salt Loading in Renal IM

This study examined the responses of IM methylamines, polyols, and total osmolytes in a diuretic state, salt loading. Using a model of salt loading modified from Arieff et al. (1977, supra), we tested the hypothesis that IM methylamines, polyols, and total osmolytes would respond uniformly, and in a parallel fashion, to a decrease in urine osmolality ($U_{osmol}$). The results indicated that salt loading promoted a 42% decrease in $U_{osmol}$ but the total pool of methylamines and polyols was unchanged. In fact, betaine and sorbitol were elevated with salt loading, indicating a dissociation in their levels from $U_{osmol}$ and demonstrating that $U_{osmol}$ was not the predominant stimulus for accumulation of these solutes. Finally, GPC was directly correlated with $U_{osmol}$, and this was the only organic osmolyte demonstrated to have this association.

A. MATERIALS AND METHODS

Animals were male Sprague-Dawley rats, as described in Example II. Tissue extracts were prepared as described in Examples I and II. Plasma sodium concentration was measured in blood collected from the tail at the beginning of the experiment and from trunk blood collected at the time of death. Sequential, 24 hour urine samples were collected under mineral oil for daily analyses of volume, sodium, and osmolality. Sodium concentrations were measured by flame photometry (Instrumentation Laboratories), and osmolality was measured with a vapor pressure osmometer (Wescor, No. 5100, Logan, UT). Osmolytes were measured with $^1$H-NMR spectroscopy or by biochemical assays as described in Examples I and II. Statistical analyses were performed as described in Examples I and II.

B. RESULTS

Metabolic parameters. As shown in Table 4, salt loading resulted in a significant increase in plasma sodium concentration (i.e., hypernatremia) from $144\pm3$ to $163\pm4$ meq/l, whereas control rats exhibited no significant change in plasma sodium concentration from their initial level of $143\pm1$ meq/l. It is important to note that plasma sodium values in salt-loaded rats were determined in samples obtained 24 h after NaCl gavage and presumably reflect minimum or "trough" values. In addition, salt-loaded rats reduced their food intake by 81% and lost 22% of their body weight.

FIG. 20A–D show time-dependent changes in urine volume, sodium concentration, sodium excretion, and osmolality in salt-loaded and control animals. Control and salt-loaded (FIG. 20A) rats excreted $12.0\pm1.4$ and $12.6\pm1.2$ ml ($p>0.5$) of urine, respectively, on day 0. Though urine volume of controls did not change significantly throughout the protocol, the salt-loaded rats developed marked saline diuresis that resulted in a 4- to 5-fold increase in urine volume on days 1–5. Urine sodium concentration (FIG. 20B) of control rats was $155\pm24$ meq/l on day 0 and did not change significantly throughout the protocol. In contrast, urine sodium concentration in salt-loaded rats rose significantly from $186\pm18$ meq/l on day 0 ($p<0.5$ vs. control) to $426\pm15$ meq/l on day 2 ($p<0.001$), and plateaued at this level throughout the remainder of the protocol. Urine sodium excretion (FIG. 20C) in control rats and salt-loaded rats was similar on day 0 ($1.79\pm0.20$ and $2.20\pm0.22$ meq sodium/day, respectively, $p<0.5$). Sodium excretion in controls did not change significantly from the initial rate on any day throughout the protocol (final day $2.27\pm0.27$ meq sodium/day). In contrast, urine sodium excretion in salt-loaded rats increased some 15-fold to a maximum of $4.6\pm3.9$ meq sodium/day on day 2 and plateaued at about 30 meq sodium/day for the remainder of the protocol. Sodium excretion of salt-loaded rats at the end of the protocol (day 5) was $30.9\pm7.1$ meq/day, significantly higher than their level on day 0 ($p<0.01$) and nearly 13-fold higher than control rats on the final day ($p<0.01$).

TABLE 4

| | Metabolic Parameters | | | |
|---|---|---|---|---|
| | Control | | Salt-Loaded | |
| | Initial | Final | Initial | Final |
| Plasma Na+, meq/l | 143 ± 1 | 139 ± 3 | 144 ± 3 | 163 ± 4* |
| Body wt, g | 347 ± 8 | 369 ± 7** | 342 ± 3 | 263 ± 6* |
| Food intake, g/day | 27.2 ± 2.0 | 26.0 ± 2.0 | 24.3 ± 2.0 | 4.7 ± 2.0* |

Values are means ± SE. Plasma sodium concentration, body weight, and food intake were measured at the beginning (day 0) and end (day 4 for controls, day 5 for salt-loaded ) of eaxh protocol. The salt-loaded rats exhibited an increased plasma sodium concentration, decreased body weight, and decreased food intake. * p < 0.001 vs. initial: **p < 0.05 vs. initial.

Despite the significant rise in urine sodium concentration (FIG. 20B), salt-loaded rats exhibited a 34% fall in $U_{osmol}$, from 1,885±105 mosmol/kgH2O on day 0 to 1,246±115 mosmol/kgH2O (p<0.001) on day 5 (FIG. 20D). The control rats experienced a slight rise in urine osmolality from 1,849±62 to 2,147±95 mosmol/kgH2O (p<0.05). At the end of the protocols the control and salt-loaded groups of rats differed significantly in urine output, sodium concentration, sodium excretion, and osmolality. Furthermore, within 2 days the salt-loaded rats achieved a steady state in urinary excretion of volume, sodium, and osmolality.

FIG. 21 compares the IM contents of methylamines and polyols observed in control and salt-loaded rats. The IM methylamines, GPC and betaine, were both altered significantly with salt loading. GPC was 41% lower in salt-loaded rats (200±17 nmol/g wet wt). In striking contrast, betaine was 286% higher in salt-loaded rats (251±26 nmol/mg protein; 22.6±2.7 μmol/g wet wt) than in control rats (65.0±10.0 nmol/mg protein; 6.5±1.4 μmol/g wet wt). Because these methylamines changed in opposite directions with salt loading, the total methylamine pool (GPC+betaine) of the salt-loaded animals (451 ±25 nmol/mg protein; 43.6±3.5 μmol/g wet wt) was not significantly different from the methylamine pool of the control rats (406±32 nmol/mg protein; 39.2±4.1 μmol/g wet wt, FIG. 22).

IM sorbitol content in control rats was 129±7 nmol/mg protein (12.6±1.3 μmol/g wet wt) and it was 33% higher in salt-loaded rats at 171±6 nmol/mg protein (16.7±1.3 μmol/g wet wt). In contrast, the myo-inositol content of salt-loaded rats (276±40 nmol/mg protein; 26.9±4.4 μmol/g wet wt) was not significantly different from that of control rats (302±27 nmol/mg protein; 29.2±3.1 μmol/g wet wt). Total polyols (sorbitol+myo-inositol) in controls were 431 ±31 nmol/mg protein (41.7±4.0 μmol/g wet wt) vs. 447±45 nmol/mg protein in salt-loaded animals (43.6±5.5 μmol/g wet wt), demonstrating no significant change (FIG. 22).

FIG. 22 compares the total IM organic osmolyte contents (i.e., GPC+betaine+myo-inositol+sorbitol) in the two groups of rats. Control rats had a total of 837±nmol/mg protein (81.0±6.6 μmol/g wet wt) compared with 898±53 nmol/mg protein (87.1±8.1 μmol/g wet wt, p>0.5), in salt-loaded rats, demonstrating that chronic salt loading did not alter significantly the total organic osmolyte pool of the IM. Furthermore, neither total methylamines nor total polyols were significantly affected by salt loading (FIG. 22) in spite of the significant changes observed in GPC, betaine, and sorbitol (FIG. 21).

C. DISCUSSION

This study examined changes in IM methylamines and polyols, which occur in response to the saline diuresis associated with salt loading. Salt loading produced a fall in urine osmolality and marked increases in urine volume and sodium excretion. Specifically, urine osmolality in salt-loaded animals (1,246±115 mosmol/kg-H2O) was 42% less than in controls. Urine volume and sodium excretion were 427 and 1262% higher, respectively, in salt-loaded rats. Consequently, salt loading produced sustained saline diuresis and decreased urine osmolality.

The most striking finding in this study was that GPC was the only IM organic osmolyte that changed in parallel with urine osmolality. IM GPC content in salt-loaded rats was 41% lower than controls compared to $U_{osmol}$ which was 42% lower.

To address whether there was a direct relationship between GPC content and $U_{osmol}$ we compared the results of this study with those in Example I, above, with other data obtained in our laboratory using different rat strains and water states. FIG. 23 indicates that there is a direct and highly significant correlation (p<0.001) between IM GPC content and urine osmolality. The slope of the regression line is −0.137 nmol GPC.mg protein$^{-1}$. Analysis of all the individual data from the present study also showed a significant correlation (p<0.001) between GPC and $U_{osmol}$ and the slope of the regression line (0.151 nmol GPC-mg protein$^{-1}$-mosmol$^{-1}$, r=0.72) was comparable to that shown in FIG. 4.

In summary, significant changes in individual IM methylamines and polyols were induced with salt loading without a change in total osmolytes. Only GPC content was directly correlated with urine osmolality, and this correlation was confirmed in three separate studies in our laboratory. IM myo-inositol content was similar in control and salt-loaded rats, appearing not to participate in an osmoregulatory response. In addition, with salt loading, IM betaine and sorbitol levels were dissociated from urine osmolality but paralleled elevations in urine and plasma sodium, which might facilitate accumulation of these solutes. Urine osmolality, however, could not be implicated in the accumulation of betaine and sorbitol.

EXAMPLE V

Hypertonicity-Induced Myo-Inositol Accumulation In C6 Glimoa Cells: A Model of Brain Osmoregulation To characterize the mechanisms of neural cell organic osmolyte regulation, rat C6 glioma cells were cultured in a medium made hypertonic (440 mOsm) by addition of 90 mM NaCl. Partially confluent (30%) C6 cultures exposed to gradual increases in NaCl concentration (30 mM every other day) followed by 6 days of maintenance in 440 mOsm medium showed normal growth and survival.

$^1$H NMR revealed that the major organic osmolyte accumulated in C6 cells during exposure to hypertonic medium was myo-inositol. Enzymatic assays demonstrated that cell myo-inositol content increased significantly from 45±5 nmol/mg prot. (n=4) in control medium to 216 ±25 nmol/mg prot (n=4) in 440 mOsm medium. Total cellular myoinositol content increased rapidly from 78±11 nmol/mg protein in control medium to 243±24 nmol/mg protein (n=4) after 10 hrs of exposure to 440 mOsm medium and remained constant for an additional 62 hrs.

These results indicate that myo-inositol plays an important role in C6 cell volume regulation. C6 cells provide a useful model for understanding brain organic osmolyte regulation during disturbance in extracellular fluid osmolality.

To examine the mechanism responsible for myo-inositol accumulation by C6 glioma cells, myo-inositol transport studies were performed. The results indicated that C6 cells possess a phlorizininhibitable myo-inositol transport pathway which is responsible for accumulation of myo-inositol by these cells under hyperosmolar conditions.

Confluent C6 cells were treated for 4, 10, and 24 hours with control medium or hyperosmolar (+NaCl) medium. At each time point, radioactive myo-inositol uptake by the cells was measured as follows. Cells were washed twice with PBS of the appropriate osmolality and 3 ml of control or hyperosmolar medium containing $^3$H-inositol was added to each plate. After 1 minute the medium was rapidly removed and the cells were washed three times with ice-cold "stop" solution (0.1 M $MgCl_2$+0.1 mM phlorizin for control cells and 0.15 M $MgCl_2$+phlorizin for hyperosmolar cells). The cells were scraped from the dish in the presence of 1 ml perchloric acid. The $^3$H-inositol content of the PCA extract was determined by scintillation spectroscopy. Parallel experiments determined the $^3$H-inositol uptake in the presence of phlorizin, an inhibitor of $Na+$-inositol cotransport. The results indicated that the C6 cells possess an myo-inositol uptake mechanism which is inhibited 80 to 90% by phlorizin. The transport rate of cells under control conditions was 77±4 pmol/min/mg protein. Moreover, there was an up-regulation of the phlorizin-inhibitable myoinositol transport under hyperosmolar conditions (FIG. 24). The increase in myo-inositol transport corresponded exactly with the time course of myo-inositol accumulation by these cells. In addition, the uptake rate was sufficient to account for all of the myo-inositol accumulated by the cells under hyperosmolar conditions. In conclusion, C6 glioma cells, a model of brain glial cells, accumulate myo-inositol under hyperosmolar conditions by uptake from the extracellular environment.

EXAMPLE VI

Restoration of Brain Tissue Water Levels Under Hyperosmolar Conditions with Osmolytes The loss of water from brain tissue which accompanies hypernatremic conditions was modeled in a system of water loss from rabbit brain tissue slices induced by high salt. The ability of two organic osmolytes, myo-inositol and glutamine, to correct this dehydration was assessed.

Rabbits were anesthetized with ketamine plus ether and the cranium was surgically opened. Brain tissue was removed and placed in ice-cold serum. Brain tissue was sliced using a Stadie-Riggs tissue slicer. The slices (0.2 to 0.5 g wet weight) were placed in capped polycarbonate flasks containing the appropriate experimental medium, gassed with a mixture of 95% $O_2$ and 5% $CO_2$, and incubated in a shaking water bath at 37° C. The experimental medium was either rabbit serum, (Control), serum+100 mM NaCl (hyperosmolar), or serum+100 mM NaCl +myo-inositol (2 mM) and/or glutamine (2 mM). After 3 hours of incubation, the tissue was blotted with filter paper and wet weight was determined with an analytical balance. The tissue was dried for 18-24 hours at 100° C. and dry weight was then determined. The % Tissue Water was calculated as: [(wet wt. −dry wt.) / wet wt.]×100.

As shown in FIG. 25, brain slices incubated in serum contained 83.3% water, whereas the tissue water of slices exposed to hyperosmolar NaCl, to mimic hypernatremia, was reduced markedly, to 80.2%. This water loss was almost completely reversed by addition of 2 mM myo-inositol (82.6%), 2 mM glutamine (82.7%), or a mixture of myoinositol and glutamine (85%).

EXAMPLE VII

The Effect of Hyponatremia on Brain Organic Osmolytes

Sprague-Dawley rats were made hyponatremic as described previously (Verbalis, J. G. et al., *Kidney International* 34:351-360 (1988)). Briefly, rats were placed on a nutritionally balanced liquid diet (AIN-76, Bio-Serv, Frenchtown, NJ) formulated as follows: 258 g powered formula+520 ml of a solution of 14% dextrose. Each day the rats received 40 ml of the liquid diet. Control rats also had access to tap water ad lib. Subcutaneous osmotic minipumps were implanted to enable continuous infusion of DDAVP, a vasopressin analogue, to hyponatremic rats or infusion of saline to control rats. Plasma $Na^+$ concentrations were 142 and 102 meq/l in control and hyponatremic rats, respectively. At 0, 2, 7, and 14 days rats were sacrificed and the brains were rapidly removed, bisected, and weighed. One hemisphere was used to prepare a perchloric acid (PCA) extract for measurement of organic osmolytes as described previously (Heilig, C. W. et al *Am. J. Physiol.* 257:F1108-F1116 (1989). Neutralized PCA extracts were analyzed by high performance liquid chromatography (HPLC) as described previously (Wolff, S. D. et al., *Am. J. Physiol.* 256:F954-F956 (1989). At days 2, 7 and 14, the levels of myoinositol, glutamate, glutamine, glycerophosphorylcholine, taurine and creatine were lower in brains of hyponatremic rats than in control rat brains. (FIG. 26A-26F). These results indicate that as the serum sodium concentration decreases, brain organic osmolytes become depleted.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

What is claimed is:

1. A method of treating osmotic disturbance in an animal, which comprises administering enterally or parentally to said animal an effective amount of an organic osmolyte, wherein the organic osmolyte is a polyol.

2. The method of claim 1 wherein said polyol is myo-inositol or sorbitol.

3. The method of claim 1 wherein said polyol is myo-inositol.

4. A method of treating osmotic disturbance in an animal, which comprises administering enterally or parentally to said animal an effective amount of a precursor of a organic osmolyte, wherein the organic osmolyte is a polyol.

5. The method of claim 4 wherein said precursor is selected from the group consisting of glucose, a glucose polymer, and glycerol.

6. The method of claim 1 or 4 wherein said osmotic disturbance occurs substantially associated with acute hyponatremia, chrominc hyponatremia, brain myelinolysis including central pontine myelinolysis, diabetic ketoacidosis, alcoholism, acute hypernatremia, chronic hypernatremia, hyperglycemic hyperosmolar coma, or urema.

7. The method of claim 6 wherein said osmotic disturbance occurs substantially associated with acute hyponatrema.

8. The method of claim 6 wherein said osmotic disturbance occurs substantially associated with chronic hyponatremia.

9. The method of claim 6 wherein said osmotic disturbance occurs substantially associated with acute hypernatremia.

10. The method of claim 6 wherein said osmotic disturbance occurs substantially associated with chronic hypernatremia.

11. The method of claim 1 or 4 wherein said osmotic disturbance occurs substantially associated with dialysis.

12. The method of claim 11 wherein said dialysis results in dialysis disequilibrium syndrome.

13. The method of claim 11 wherein said dialysis results in accidental salt loading.

14. A method of preventing an osmotic disturbance substantially associated with physical activity comprising enterally administering to a subject prior to, during, or both prior to and during said physical activity an effective amount of an organic osmolyte or a precursor of an organic osmolyte, whereinsaid organic osmolyte or precursor is a polyol.

* * * * *